United States Patent [19]
Amara et al.

[11] Patent Number: 5,919,699
[45] Date of Patent: Jul. 6, 1999

[54] AMINO ACID TRANSPORTERS AND USES

[75] Inventors: Susan G. Amara; Jeffrey L. Arriza, both of Portland, Oreg.

[73] Assignee: State of Oregon, Portland, Oreg.

[21] Appl. No.: 08/546,661

[22] Filed: Oct. 23, 1995

Related U.S. Application Data

[62] Division of application No. 08/140,729, Oct. 20, 1993.
[51] Int. Cl.$^6$ .............. C12N 5/00; C12N 1/20; C12N 15/00; C07H 21/04
[52] U.S. Cl. ............ 435/325; 435/252.3; 435/320.1; 536/23.5; 536/24.3
[58] Field of Search .............. 435/6, 69.1, 240.2, 435/320.1, 252.3; 536/23.5, 24.3

[56] References Cited

U.S. PATENT DOCUMENTS

| | | | |
|---|---|---|---|
| 4,683,195 | 7/1987 | Mullis et al. | 435/6 |
| 5,424,185 | 6/1995 | Lam et al. | 435/6 |
| B1 4,683,202 | 11/1990 | Mullis | 435/91 |

OTHER PUBLICATIONS

Anderson et al. (1989) J. Biol. Chem. 264: 8222–8229.
Arriza et al. (1992) J. Neurosci. 12: 4045–4055.
Arriza et al. (1994) J. Neurosci. 14(9):5559–5569.
Bertling (1987) Bioscience Reports 7: 107–112.
Blakely et al. (1991) Anal. Biochem. 194: 302–308.
Bouvier et al. (1992) Nature 360: 471–474.
Bussolati et al. (1992) J. Biol. Chem. 267: 8330–8335.
Choi et al. (1987) Neurosci. 7: 357–358.
Chomczynski & Sacchi (1987) Anal. Biochem. 162: 156–159.
Christensen (1990) Physiol. Rev. 70: 43:77.
Christensen et al. (1967) J. Biol. Chem. 242: 5237–5246.
Eisenberg et al. (1984) J. Molec. Biol. 179: 125–142.
Engelke et al. (1992) J. Bacteriol. 171: 5551–5560.
Felgner et al. (1987) Proc. Natl. Aced. Sci. USA 84: 7413–7417.
Gluzman (1981) Cell 23: 175–182.
Guastella et al. (1992) Proc. Natl. Acad. Sci. USA 89: 7189–7193.
Kanai & Hediger (1992) Nature 360: 467–471.
Kanai et al. (1993) Trends in Neurosci. 16(9): 365–370.
Kanai et al. (1994) J. Biol. Chem. 269(32):20599–10606.
Kanner & Schuldiner (1987) CRC Crit. Rev. Biochem. 22: 1–38.
Kanner (1993) FEBS Lett. 325(1,2): 95–99.
Kavanaugh et al. (1992) J. Biol. Chem. 267: 22007–22009.
Kim et al. (1991) Nature 352: 725–728.
Kong et al. (1993) J. Biol. Chem. 268: 1509–1512.
Kozak (1987) Nucleic Acids Res 15: 8125–8132.
Maenz et al. (1992) J. Biol. Chem. 267: 1510–1516.
Makowske & Christensen (1982) J. Biol. Chem. 257: 14635–14638.
Nicholls & Attwell (1990) TIPS 11: 462–468.
Olney et al. (1990) Science 248: 596–599.
Pines et al. (1992) Nature 360: 464–467.
Saiki et al. (1988) Science 239: 487–491.
Sanger et al. (1977) Proc. Natl. Acad. Sci. USA 74: 5463.
Schloss et al. (1992) FEBS Lett. 307(1): 76–80.
Smith and Johnson (1988) Gene 67: 31–40.
Smithies et al. (1985) Nature 317: 230–234.
Stelzner et al. (1993) FASEB J. 7 (4/part 2): A575.
Storck et al. (1992) Proc. Natl. Acad. Sci. USA 89: 10955–10959.
Thomas & Capecchi (1987) Cell 51: 503–512.
Uhl (1992) Trends in Neurosci. 15(7): 265–268.
Wallace et al. (1990) J. Bacteriol. 172: 3214–3220.
Wang et al. (1991) Nature 352: 729–731.
Georgiou, G. (1988) AIChE J. 34(8): 1233–1248.
Kanai et al. (1993) FASEB J. 7(15): 1450–1459.
Shashidharan et al. (1993) Biochim. Biophys. Acta 1216: 161–164.

*Primary Examiner*—Robert A. Wax
*Assistant Examiner*—Lisa J. Hobbs
*Attorney, Agent, or Firm*—McDonnell, Boehnen, Hulbert & Berghoff

[57] ABSTRACT

The present invention relates to novel mammalian amino acid transporter proteins and the genes that encode such proteins. The invention is directed toward the isolation, characterization and pharmacological use of the human amino acid transporter proteins EAAT1, EAAT2, EAAT3 and ASCT1. The invention specifically provides isolated complementary DNA copies of mRNA corresponding to each of these transporter genes. Also provided are recombinant expression constructs capable of expressing each of the amino acid transporter genes of the invention in cultures of transformed prokaryotic and eukaryotic cells, as well as such cultures of transformed cells that synthesize the human amino acid transporter proteins encoded therein. The invention also provides methods for screening in vitro compounds having transport-modulating properties using preparations of transporter proteins from such cultures of cells transformed with recombinant expression constructs.

4 Claims, 42 Drawing Sheets

FIG. 1A

```
CACCTCTAGC TCGGAGCGGC GTGTAGCGCC                                                        54

ATG GAG AAG AGC AAC GAG ACC AAC                          102
                              Met Glu Lys Ser Asn Glu Thr Asn
                                1                  5

GGC TAC CTT GAC AGC GCT CAG GCG GGG GCC CCT GCA GCC GGA GCT        150
Gly Tyr Leu Asp Ser Ala Gln Ala Gly Ala Pro Ala Ser Gly Ala
 10                      15                  20

CCG GGG ACC GCG GCG GGA CGC GCA CGG TGC CGC CGC TTC CGG            198
Pro Gly Thr Ala Ala Gly Arg Ala Arg Cys Arg Arg Phe Arg
 25                  30              35              40

CGC CAA GCG CTG GTG CTG CTC ACC GTG TCC GGG GTG CTG GCG            246
Arg Gln Ala Leu Val Leu Leu Thr Val Ser Gly Val Leu Ala
             45                  50              55

GGC CTG GGC GCG GCA TTG CGC CCC GGG GAG ATG CTG AGC CTG            294
Gly Leu Gly Ala Ala Leu Arg Pro Gly Glu Met Leu Ser Leu
 65                  70              75              85
                                    80

ACC TAC CTG GCC TTC CCC GGC ATG ATG AGC CTC CTC CGC ATG            342
Thr Tyr Leu Ala Phe Pro Gly Met Met Ser Leu Leu Arg Met
         75              85

ATC ATC CTG CCG GTG GTC TGC AGC CTG GTG TCG GCC GCC TCG
Ile Ile Leu Pro Val Val Cys Ser Leu Val Ser Gly Ala Ser
 90              95          100
```

FIG. 1B

```
CTC GAT GCC AGC TGC CTC GGG CGT CTG GGC ATC CGT GTC GCC TAC                390
Leu Asp Ala Ser Cys Leu Gly Arg Leu Gly Ile Arg Val Ala Tyr
105             110             115             120

TTT GGC CTC ACC ACA CTG AGT CCA CTG GCG TCG GCC GTG GCC TTG GCG            438
Phe Gly Leu Thr Thr Leu Ser Pro Leu Ala Ser Ala Val Ala Leu Ala
            125             130             135

TTC ATC AAG CCA GGA TCC CCA GCG GGT CAG ACC CTT GCC GTG TCC AGC GAC        486
Phe Ile Lys Pro Gly Ser Pro Ala Gly Gln Thr Leu Ala Val Ser Asp
        140             145             150

CTG GGG GAC TCG GGG GGG CCT GTC CCC TTT CCC AAA TCC GAG ACG            534
Leu Gly Asp Ser Gly Gly Pro Val Pro Phe Pro Lys Ser Glu Thr
155             160             165

GAC TCT GAC CTC AAC AGA CTG CTT TAT AAA TCC AAT CTT ACC            582
Asp Ser Asp Leu Asn Arg Leu Leu Tyr Lys Ser Asn Leu Thr
170             175             180

GTT GCA CTT TTC CGT ACG GAT TAT ACC GAT TAT AAG ATC CCC GTG            630
Val Ala Leu Phe Arg Thr Asp Tyr Thr Asp Tyr Lys Ile Pro Val
185             190             195

AAC AGC TCT GGA GTA AAT CAT GAA CCC ATA GGC            678
Asn Ser Ser Gly Val Asn His Glu Pro Ile Gly
        205             210             215
```

FIG. 1C

```
                                                                                                                      726
GAG  ATA  GAA  GGG  ATG  AAC  ATT  TTA  GGA  TTG  GTC  CTG  TTT  GCT  CTG  GTG
Glu  Ile  Glu  Gly  Met  Asn  Ile  Leu  Gly  Leu  Val  Leu  Phe  Ala  Leu  Val
               220                      225                      230

774
TTA  CGA  GTG  GCC  TTA  AAA  CTA  TCC  GAA  GGA  TTT  GAA  GAC  CTC  ATC
Leu  Gly  Val  Ala  Leu  Lys  Leu  Ser  Glu  Gly  Phe  Glu  Asp  Leu  Ile
          235                 240                      245

822
CGT  TTC  AAT  TCC  CTC  AAC  AAA  CTA  GGC  TCC  ATG  GTG  GAA  GGA  GAC  CTC
Arg  Phe  Asn  Ser  Leu  Asn  Lys  Leu  Gly  Ser  Met  Val  Glu  Gly  Asp  Leu
     250                      255                      260

870
ATT  ATG  TGG  GTA  CCT  GTG  GGC  ATC  ATG  TTC  CCT  GTG  ATG  CTG  GTT  TGG
Ile  Met  Trp  Val  Pro  Val  Gly  Ile  Met  Phe  Leu  Val  Met  Leu  Val  Trp
265       270                           275                      280

918
ATC  GTG  GAA  ATG  AAA  TCT  GAC  ATC  ATC  GTG  CTG  ACC  AGC  CTG  GGA  AAA
Ile  Val  Glu  Met  Lys  Ser  Asp  Ile  Ile  Val  Leu  Thr  Ser  Leu  Gly  Lys
                    285                           290                  295

966
TAC  ATC  TTC  GGA  GCA  TCT  TTG  ATA  GGC  CAT  GTT  ATT  CAT  GGA  ATT  GTT
Tyr  Ile  Phe  Gly  Ala  Ser  Leu  Ile  Gly  His  Val  Ile  His  Gly  Ile  Val
                    300                      305                      310

1014
CTG  CCA  ATT  TAT  TTT  GTT  TTC  ACA  CGA  AAA  AAC  CCA  TTC  TTC  AGA  TTC
Leu  Pro  Ile  Tyr  Phe  Val  Phe  Thr  Arg  Lys  Asn  Pro  Phe  Phe  Arg  Phe
315                      320                      325
```

FIG. 1D

```
CTC  CTG  GGC  CTC  GCC  CCA  TTT  GCG  ACA  GCA  TTT  GCT  ACC  TGC  TCC                1062
Leu  Leu  Gly  Leu  Ala  Pro  Phe  Ala  Thr  Ala  Phe  Ala  Thr  Cys  Ser
     330                      335                      340

AGC  TCA  GCG  ACC  CTT  CCC  TCT  ATG  ATG  AAG  TGC  GAA  GAG  AAC  AAT                1110
Ser  Ser  Ala  Thr  Leu  Pro  Ser  Met  Met  Lys  Cys  Glu  Glu  Asn  Asn
345                           350                      355                     360

GGT  GTG  GAC  AAG  AGG  ATC  AGC  AGG  TTT  ATT  CCC  ATC  GGG  GCC  ACC                1158
Gly  Val  Asp  Lys  Arg  Ile  Ser  Arg  Phe  Ile  Pro  Ile  Gly  Ala  Thr
                    365                      370                           375

GTG  AAC  ATG  GAC  GGA  GCA  GCC  CTC  TTC  CAG  ATC  CTC  CCC  GCC  GTG                1206
Val  Asn  Met  Asp  Gly  Ala  Ala  Leu  Phe  Gln  Ile  Leu  Pro  Ala  Val
               380                      385                           390

ATT  GCG  CAA  CTC  AAC  ATA  GAG  TCC  CTC  GTT  GGA  GCA  CAG  GGC  ATT  TTC  ACC       1254
Ile  Ala  Gln  Leu  Asn  Ile  Glu  Ser  Leu  Val  Gly  Ala  Gln  Gly  Ile  Phe  Thr
          395                      400                      405

ATT  CTA  GTG  ACT  GCC  ACA  GCG  TCC  AGT  GTT  GGA  GCA  GCA  GGC  GTG  CCA            1302
Ile  Leu  Val  Thr  Ala  Thr  Ala  Ser  Ser  Val  Gly  Ala  Ala  Gly  Val  Pro
     410                      415                      420

GCT  GGA  GGG  GTC  CTC  ACC  ATT  GCC  ATC  CTG  GAG  GCC  ATT  GGG  CTG                1350
Ala  Gly  Gly  Val  Leu  Thr  Ile  Ala  Ile  Leu  Glu  Ala  Ile  Gly  Leu
425                      430                      435                           440
```

FIG. 1E

| CCT Pro | ACT Thr | CAT His | GAC Asp | CTG Leu 445 | CCT Pro | CTG Leu | ATC Ile | CTG Leu | GCT Ala 450 | GTG Val | GAC Asp | TGG Trp | ATT Ile | GTG Val 455 | GAC Asp | 1398 |
| --- | --- | --- | --- | --- | --- | --- | --- | --- | --- | --- | --- | --- | --- | --- | --- | --- |
| CGG Arg | ACC Thr | ACC Thr 460 | CTG Leu | GTG Val | GTG Val | AAT Asn | CTG Leu | GAG Glu 465 | GGG Gly | GAT Asp | GCC Ala | TGG Trp | CTG Leu | GGT Gly 470 | GCA Ala | GGC Gly | 1446 |
| ATT Ile | CTC Leu | CAC His 475 | CAC His | CTG Leu | AAT Asn | AAT Asn | CAG Gln | GCA Ala | ACA Thr | AAG Lys 480 | AAA Lys | GGC Gly 485 | GAG Glu | CAG Gln | GAA Glu | 1494 |
| CTT Leu | GCT Ala 490 | GAG Glu | GTG Val | AAA Lys | GAA Glu 495 | GAA Glu | GCC Ala | ATC Ile | CCC Pro | AAC Asn | TGC Cys 500 | AAG Lys | TCT Ser | GAG Glu | GAG Glu | 1542 |
| ACA Thr | TCG Ser | CCC Pro | CTG Leu | GTG Val 510 | CAG Gln | CAC His | CAG Gln | AAC Asn | CCC Pro 515 | GCT Ala | GGC Gly | CCC Pro | GTG Val | GCC Ala 520 | 1590 |
| AGT Ser | GCC Ala | CCA Pro | GAA Glu | CTG Leu 525 | GAA Glu | TCC Ser | AAG Lys | GAG Glu | TCG Ser 530 | GTT Val | CTG Leu | TGATGGGGCT | 1636 |
| GGGCTTTGGG | CTTGCCTGCC | AGCAGTGATG | TCCCACCCTG | TTCA | | | | | | | | | | | | 1680 |

FIG. 2A

```
AAAGAAGAGA CCCTCCTAGA AAAGTAAAAT                                              ATG ACT AAA AGC AAT GGA GAA GAG    54
                                                                             Met Thr Lys Ser Asn Gly Glu Glu
                                                                              1                5

CCC AAG ATG GGG GGC AGG ATG GAG TTC CAG CAG GGA CAG CAG GTC CTG AAA          102
Pro Lys Met Gly Gly Arg Met Glu Phe Gln Gln Gly Gln Gln Val Leu Arg Lys
     10              15              20

CGC ACA CTT TTG GCC AGG AAG AAA ATT ACA AAG GAG GTT                          150
Arg Thr Leu Leu Ala Arg Lys Lys Ile Thr Lys Glu Val
 25              30              35              40

GTT AAA AGT TAC CTG TTT CGG AAT GCT TTT GTG CTG CTC ACC                      198
Val Lys Ser Tyr Leu Phe Arg Asn Ala Phe Val Leu Leu Thr
             45              50              55

GCT GTC ATT GTG GGT ACA ATC CTT GGA TTT TTT ACC ACC TTC TCC CGA CCA TAC AGA  246
Ala Val Ile Val Gly Thr Ile Leu Gly Phe Phe Thr Thr Phe Ser Arg Pro Tyr Arg
         60              65              70

ATG AGC TAC CGG GAA GTC AAG TAC AAG GAG CTT GGG GAA CCA CCT GGG GAA CTT CTG  294
Met Ser Tyr Arg Glu Val Lys Tyr Lys Glu Leu Gly Glu Pro Pro Gly Glu Leu Leu
     75              80              85

ATG AGG ATG CAG TTA CAG ATG CTG GTC CCA CTT CTT ATC TCC AGT CTT              342
Met Arg Met Gln Leu Gln Met Leu Val Pro Leu Leu Ile Ser Ser Leu
     90              95             100
```

FIG. 2B

| GTC Val 105 | ACA Thr | GGA Gly | ATG Met | GCG Ala | CTA Leu | GAT Asp | AGT Ser | AAG Lys | GCA Ala 115 | TCA Ser | GGG Gly | AAG Lys | TGG Trp | GAA Glu 120 | 390 |
| TGC Cys | GGA Gly | GCT Ala | GTA Val | TAT Tyr | TAT Tyr | ATG Met | ACT Thr | ACC Thr 130 | ATT Ile | GCT Ala | GTG Val 135 | | | | 438 |
| ATT Ile | GGC Gly | ATA Ile | ATC Ile | ATT Ile | GTC Val | ATC Ile | ATC Ile | CAT His | ACC Thr | ATC Ile 145 | ATT Ile | GCT Ala | GGC Gly 150 | AAG Lys | 486 |
| GAA Glu | AAC Asn | ATG Met 155 | CAC His | AGA Arg | GGC Gly | AAA Lys 160 | ATT Ile | GTA Val | CGA Arg | ACA Thr 165 | GTG Val | CCT Pro | GGG Gly | GAT Asp | 534 |
| GCC Ala | TTC Phe 170 | CTG Leu | GAC Asp | TTG Leu | ATC Ile | AGG Arg 175 | ATG Met | TTA Leu | AAT Asn | CCA Pro 180 | GTG Val | AAT Asn | CTG Leu | GAA Glu | 582 |
| GCC Ala 185 | TGC Cys | TTT Phe | AAA Lys | GAG Gln | TTT Phe 190 | AAA Lys | TAT Tyr | GAG Glu 195 | AAG Lys | AGA Arg | AGC Ser | TTT Phe | AAA Lys 200 | | 630 |
| GTG Val | CCC Pro | ATC Ile | GAG Gln | GCC Ala 205 | AAC Asn | GAA Glu | CCT Leu | GTG Val 210 | ACG Thr | GGT Gly | GCT Ala | GTG Val | ATA Ile | AAC Asn 215 | 678 |

FIG. 2C

```
GTG TCT GAG GCC ATG GAG ACT CTT ACC CGA ATC ACA GAG CTG GTC         726
Val Ser Glu Ala Met Glu Thr Leu Thr Arg Ile Thr Glu Leu Val
            220             225             230

CCA GTT CCA GGA TCT GTG AAT GGA GTC AAT GCC CTG CTA GTT GTC         774
Pro Val Pro Gly Ser Val Asn Gly Val Asn Ala Leu Leu Val Val
        235             240             245

TTC TCC ATG TGC TTC GGT TTT GTG ATT GGA AAC ATG AAG CAG GGG         822
Phe Ser Met Cys Phe Gly Phe Val Ile Gly Asn Met Lys Gln Gly
    250             255             260

GAG GCC CTG AGA GAG TTC TTT GAT TCT CTT AAC GAA GCC ATC ATG AGA     870
Gln Ala Leu Arg Glu Phe Phe Asp Ser Leu Asn Glu Ala Ile Met Arg
265             270             275             280

CTG GTA GCA ATA ATG TGG TAT GCC GTG GGT ATT GGT ATT CTC CTG         918
Leu Val Ala Ile Ile Met Trp Tyr Ala Val Gly Ile Gly Ile Leu Leu
                285             290             295

ATT GCT GGG AAG ATT GAG ATG GAA GAC ATG GGT GGT ATT GGG GGG         966
Ile Ala Gly Lys Ile Ile Glu Met Glu Asp Met Gly Gly Ile Gly Gly
            300             305             310

CAG CTT GCC ATG TAC ACC GTG ACT GTC ATT GTT GGC TTA CTC ATT CAC    1014
Gln Leu Ala Met Tyr Thr Val Thr Val Ile Val Gly Leu Leu Ile His
        315             320             325
```

FIG. 2D

```
GCA  GTC  ATC  GTC  TTG  CCA  CTC  CTC  TAC  TTC  TTG  GTA  ACA  CGG  AAA  AAC           1062
Ala  Val  Ile  Val  Leu  Pro  Leu  Leu  Tyr  Phe  Leu  Val  Thr  Arg  Lys  Asn
     330                      335                      340

CCT  TGG  GTT  TTT  ATT  GGA  GGG  TTG  CTG  CAA  GCA  CTC  ATC  ACC  GCT  CTG           1110
Pro  Trp  Val  Phe  Ile  Gly  Gly  Leu  Leu  Gln  Ala  Leu  Ile  Thr  Ala  Leu
345                      350                      355                           360

GGG  ACC  TCT  TCA  AGT  TCT  GCC  CCC  CTA  ACC  GCA  CCC  ATC  TTC  AAG  TGC  CTG      1158
Gly  Thr  Ser  Ser  Ser  Ser  Ala  Pro  Leu  Thr  Ala  Pro  Ile  Phe  Lys  Cys  Leu
               365                           370                           375

GAA  AAC  GGC  AAT  GGC  GTG  GAC  AAG  CGC  CTA  CCC  GTC  AGA  TTC  CTC  CCC           1206
Glu  Asn  Gly  Asn  Gly  Val  Asp  Lys  Arg  Leu  Pro  Val  Arg  Phe  Leu  Pro
          380                      385                      390

GGA  GCC  ACC  ATT  GGG  GAT  ATG  AAC  AAA  AAC  ACT  GCC  TAT  CTG  GAG  TTG           1254
Gly  Ala  Thr  Ile  Gly  Asp  Met  Asn  Lys  Asn  Thr  Ala  Tyr  Leu  Glu  Leu
                    395                      400                      405

GCC  ATT  ATT  TTC  ATG  CAA  GTT  AAC  AAC  TTT  GAA  CTG  AAC  TTC  GGA              1302
Ala  Ile  Ile  Phe  Met  Gln  Val  Asn  Asn  Phe  Glu  Leu  Asn  Phe  Gly
410            415                      420

CAA  ATT  ATT  ACA  AGC  ATC  ACA  GCC  ACA  GCT  GCC  AGT  GGG  TTG  GGA  GCA           1350
Gln  Ile  Ile  Thr  Ser  Ile  Thr  Ala  Thr  Ala  Ala  Ser  Gly  Leu  Gly  Ala
425                      430                      435                           440
```

FIG. 2E

```
GCT GGA ATT CCT CAG GCG GGC CTG GTC ACT ATG GTC ATT GTG CTG ACA
Ala Gly Ile Pro Gln Ala Gly Leu Val Thr Met Val Ile Val Leu Thr      1398
                445                 450                 455

TCT GTC GGC CTG CTG CCC ACT GAC GAC GAT ATC ATC CTC ATC GCG GTG GAC
Ser Val Gly Leu Leu Pro Thr Asp Asp Ile Ile Leu Ile Ala Val Asp      1446
        460                 465                 470

TGG TTC GAT CGC CTC CGG ACC ACC CAC ACC GTA CTG GGA GAC TCC
Trp Phe Asp Arg Leu Arg Thr Thr His Thr Val Leu Gly Asp Ser          1494
475                 480                 485

CTG GGA GCT ATT GTG GAG CTG CAT TTG TCA CGA CAT GAA CTG AAG AAC
Leu Gly Ala Ile Val Glu Leu His Leu Ser Arg His Glu Leu Lys Asn      1542
    490                 495                 500

AGA GAT GTT ATG GGT AAC TCA GTG ATT GAG ATT GAA ATG AAG
Arg Asp Val Met Gly Asn Ser Val Ile Glu Ile Glu Met Lys             1590
505                 510                 515                 520

AAA CCA TAT CAA CTG CTG ATT GCA CAG GAC AAT GAA ACT GAG AAA CCC ATC
Lys Pro Tyr Gln Leu Leu Ile Ala Gln Asp Asn Glu Thr Glu Lys Pro Ile  1638
                525                 530                 535

GAC AGT GAA ACC AAG ATG TAGACTAACA TAAAGAAACA CTTT                   1680
Asp Ser Glu Thr Lys Met
                540
```

FIG. 3A

```
GATAGTGCTG AAGAGGAGG  GCGTTCCCAG  ACC                                            54

AAC AAT ATG CCC AAG CAG GTG GAA ATG GCA TCT ACG GAA GGT GCC              102
Asn Asn Met Pro Lys Gln Val Glu Met Ala Ser Thr Glu Gly Ala
         10              15             1           5

GGC TCA GAG GAA CCC AAG CAC CGG CAC CGA ATG CCA GAC AGT CAT CTT          150
Gly Ser Glu Glu Pro Lys His Arg His Arg Met Pro Asp Ser His Leu
     25          30              20

AAG CTG GGG AAG AAT CTG CTC CTG CTG CTG GGC CGC AGT CTG TGT GAC          198
Lys Leu Gly Lys Asn Leu Leu Leu Leu Leu Gly Arg Ser Leu Cys Asp
 40          45              35

CTG GGA GCA GTG TGT GGA GGG CTT CTT ACC ACG TTT GGT GTG GTC ATC          246
Leu Gly Ala Val Cys Gly Gly Leu Leu Thr Thr Phe Gly Val Val Ile
                 60                  50                         55

CCT GAT GTT ATG TTA ATA TTC CTT CGC CCA GGG TCT CCC ATC CTC ATG AGG      294
Pro Asp Val Met Leu Ile Phe Leu Arg Pro Gly Ser Pro Ile Leu Met Arg
         75          80              65                  70

ATG CTA AAA ATG CTC ATT GGT CTA AGC ATC TCC AGC TTA ATC ACA              342
Met Leu Lys Met Leu Ile Gly Leu Ser Ile Ser Ser Leu Ile Thr
         90              95              85          100
```

FIG. 3B

| | | | | | | | | | | | | | | | | |
|---|---|---|---|---|---|---|---|---|---|---|---|---|---|---|---|---|
| GGG | TTG | TCA | GGC | CTG | GAT | GCT | AAG | GCT | AGT | GGC | CGC | TTG | GGC | ACG | AGA | 390 |
| Gly | Leu | Ser | Gly | Leu | Asp | Ala | Lys | Ala | Ser | Gly | Arg | Leu | Gly | Thr | Arg | |
| | 105 | | | | | 110 | | | | | 115 | | | | | |
| GCC | ATG | GTG | TAT | TAC | ATG | TCC | ACG | ATC | ATT | GCT | GCA | GTA | CTG | GGG | | 438 |
| Ala | Met | Val | Tyr | Tyr | Met | Ser | Thr | Ile | Ile | Ala | Ala | Val | Leu | Gly | | |
| 120 | | | | | 125 | | | | 130 | | | | | 135 | | |
| GTC | ATT | CTG | GTC | TTG | GCT | ATC | CAT | CCA | GGC | AAT | CCC | AAG | CTC | AAG | | 486 |
| Val | Ile | Leu | Val | Leu | Ala | Ile | His | Pro | Gly | Asn | Pro | Lys | Leu | Lys | | |
| | | | | 140 | | | | | 145 | | | | | 150 | | |
| CAG | CTG | GGG | CCT | GAT | CAT | AAT | CAT | AAT | GAT | GAA | GTG | TCC | AGC | CTG | | 534 |
| Gln | Leu | Gly | Pro | Asp | His | Asn | His | Asn | Asp | Glu | Val | Ser | Ser | Leu | | |
| | | | 155 | | | | | | 160 | | | | | 165 | | |
| TTC | CTG | GAC | CTT | ATT | CGA | AAT | CCT | TTC | ACG | AAC | CTC | AGC | AAC | CTG | | 582 |
| Phe | Leu | Asp | Leu | Ile | Arg | Asn | Pro | Phe | Thr | Asn | Leu | Ser | Asn | Leu | | |
| | | 170 | | | | | 175 | | | | 180 | | | | | |
| TGC | TTT | CAA | CAG | ATT | CAA | ACA | GTG | ACG | AAG | AAA | GTC | GTT | GCA | CCA | | 630 |
| Cys | Phe | Gln | Gln | Ile | Gln | Thr | Val | Thr | Lys | Lys | Val | Val | Ala | Pro | | |
| | 185 | | | | | 190 | | | | | 195 | | | | | |
| CCG | GAC | GAG | GAG | AAC | GCA | ACC | AGC | GCT | GAA | GTC | TCT | CTG | TTG | | | 678 |
| Pro | Asp | Glu | Glu | Asn | Ala | Thr | Ser | Ala | Glu | Val | Ser | Leu | Leu | | | |
| 200 | | | | | 205 | | | | 210 | | | | 215 | | | |

FIG. 3C

| | | | | | | | | | | | | | | |
|---|---|---|---|---|---|---|---|---|---|---|---|---|---|---|
| AAC | GAG | ACT | GTG | ACT | GAG | CCG | GAG | ACT | AAG | ATG | GTT | ATC | AAG | |
| Asn | Glu | Thr | Val | Thr | Glu | Pro | Glu | Thr | Lys | Met | Val | Ile | Lys | 726 |
|  |  |  |  | 220 |  |  |  | 225 |  |  |  | 230 |  |  |
| AAG | GGC | CTG | GAG | TTC | AAG | GAT | GGG | ATG | AAC | GTC | TTA | GGT | CTG | ATA | GGG |
| Lys | Gly | Leu | Glu | Phe | Lys | Asp | Gly | Met | Asn | Val | Leu | Gly | Leu | Ile | Gly |
|  |  |  | 235 |  |  |  |  | 240 |  |  |  |  | 245 |  |  |
| TTT | ATT | GCT | TTT | GGC | ATC | GCT | ATG | GGG | AAG | ATG | GGA | GAT | CAG | GCC |
| Phe | Ile | Ala | Phe | Gly | Ile | Ala | Met | Gly | Lys | Met | Gly | Asp | Gln | Ala |
|  | 250 |  |  |  |  | 255 |  |  |  |  | 260 |  |  |  |
| AAG | CTG | ATG | GTG | GAT | TTC | AAC | ATT | TTG | AAT | GAG | ATT | GTA | ATG | AAG |
| Lys | Leu | Met | Val | Asp | Phe | Asn | Ile | Leu | Asn | Glu | Ile | Val | Met | Lys |
| 265 |  |  |  |  |  |  |  | 270 |  |  | 275 |  |  |  |
| GTG | ATC | ATG | TTC | TAC | TCT | CCC | CTG | GGT | ATC | GCC | TGC | CTG |
| Val | Ile | Met | Phe | Tyr | Ser | Pro | Leu | Gly | Ile | Ala | Cys | Leu |
|  |  | 285 |  |  |  |  | 290 |  |  |  |  | 295 |
| TGT | GGA | AAG | ATC | ATT | GCA | TGG | ATG | AAG | GAC | TTA | GAA | GTG | GTT | AGG |
| Cys | Gly | Lys | Ile | Ile | Ala | Trp | Met | Lys | Asp | Leu | Glu | Val | Val | Arg |
|  |  |  |  | 300 |  |  |  |  | 305 |  |  |  | 310 |  |
| CAA | CTG | GGG | ATG | TAC | ATG | GTA | ACA | GTG | ATA | ATC | GGC | CTC | ATC | CAC |
| Gln | Leu | Gly | Met | Tyr | Met | Val | Thr | Val | Ile | Ile | Gly | Leu | Ile | His |
|  |  |  | 315 |  |  |  | 320 |  |  |  |  |  | 325 |  |

| Codon | AA | Pos | Codon | AA | Pos | Codon | AA | Pos | Codon | AA | Pos | Codon | AA | Pos |
|---|---|---|---|---|---|---|---|---|---|---|---|---|---|---|

Row ending 1062:
GGG Gly | GGC Gly | ATC Ile 330 | TTT Phe | CTC Leu | CCC Pro | TTG Leu | ATT Ile 335 | TAC Tyr | TTT Phe | GTA Val | GTG Val | ACC Thr 340 | AGG Arg | AAA Lys | AAC Asn Row ending 1110:
CCC Pro | TTC Phe 345 | TCC Ser | CTT Leu | TTT Phe | GCT Ala | GGC Gly 350 | TTG Leu | ATT Ile | TTC Phe | CAA Gln | GCT Ala | TGG Trp 355 | ACT Thr | GCC Ala | CTG Leu Row ending 1158:
GGC Gly 360 | ACC Thr | GCT Ala | TCC Ser | AGT Ser | GCT Ala 365 | GGA Gly | ACT Thr | TTG Leu | CCT Pro | GTC Val 370 | ACC Thr | TTT Phe | TGC Cys | CTG Leu 375

Row ending 1206:
GAA Glu | AAT Asn | CTG Leu | GGG Gly | ATT Ile 380 | GAT Asp | ACT Thr | GGA Gly | AAG Lys | CGT Arg 385 | GTG Val | ACA Thr | AGA Arg | TTC Phe | CTT Leu 390 | TGC Cys | CCT Pro Row ending 1254:
GTT Val | GGA Gly | ACC Thr 395 | TTT Phe | ATT Ile | AAC Asn | GAT Asp | GGT Gly 400 | AAT Asn | ATG Met | TAT Tyr | CTT Leu | GTC Val 405 | GAA Glu | GCG Ala | GTG Val Row ending 1302:
GCC Ala | ATC Ile 410 | TTT Phe | ATA Ile | AAC Asn | CAA Gln | ATG Met 415 | GAT Asp | ACA Thr | GCC Ala | CCT Pro | GAT Asp | AGC Ser 420 | CTG Leu | GGA Gly | GGA Gly Row ending 1350:
CAG Gln | ATT Ile 425 | GTG Val | ACT Thr | GTA Val | AGC Ser | CTC Leu 430 | ACC Thr | CTG Leu | GCA Ala 435 | AGC Ser | GTC Val | GGC Gly | GCG Ala

FIG. 3E

| | | | | | | | | | | | | | | | | |
|---|---|---|---|---|---|---|---|---|---|---|---|---|---|---|---|---|
| GCC<br>Ala<br>440 | AGT<br>Ser | ATC<br>Ile | CCC<br>Pro | AGT<br>Ser | GCC<br>Ala<br>445 | GGG<br>Gly | CTG<br>Leu | GTC<br>Val | ACC<br>Thr | ATG<br>Met<br>450 | CTC<br>Leu | CTC<br>Leu | ATT<br>Ile | CTG<br>Leu | ACA<br>Thr<br>455 | 1398 |
| GCC<br>Ala | GTG<br>Val | GGC<br>Gly | CTG<br>Leu | CCA<br>Pro<br>460 | ACA<br>Thr | GAG<br>Glu | GAC<br>Asp | ATC<br>Ile | AGC<br>Ser<br>465 | TTG<br>Leu | CTC<br>Leu | GTG<br>Val | GCT<br>Ala | GAC<br>Asp<br>470 | | 1446 |
| TGG<br>Trp | CTG<br>Leu | CTG<br>Leu | GAC<br>Asp<br>475 | AGT<br>Ser | ATG<br>Met | AGA<br>Arg | ACT<br>Thr | TCA<br>Ser<br>480 | GTC<br>Val | AAT<br>Asn | TTG<br>Leu | GTG<br>Val | GCT<br>Ala | GGT<br>Gly<br>485 | | 1494 |
| TTT<br>Phe | GGG<br>Gly | GCT<br>Ala<br>490 | ATA<br>Ile | GTC<br>Val | TAT<br>Tyr | CAC<br>His<br>495 | TCA<br>Ser | CTC<br>Leu | AAG<br>Lys | TCT<br>Ser | GAG<br>Glu<br>500 | GTT<br>Val | GTG<br>Val | GAC<br>Asp | TCT<br>Ser | 1542 |
| ATT<br>Ile | GAC<br>Asp<br>505 | TCC<br>Ser | GAG<br>Gln | CAT<br>His | CGA<br>Arg | GTG<br>Val<br>510 | CAT<br>His | GAA<br>Glu | CTC<br>Leu | ATT<br>Ile | GAA<br>Glu<br>515 | ATG<br>Met | CTG<br>Leu | ACC<br>Thr | AAG<br>Lys | 1590 |
| CAA<br>Gln<br>520 | TCC<br>Ser | ATT<br>Ile | TAT<br>Tyr | GAT<br>Asp | GAC<br>Asp<br>525 | GAC<br>Asp | ATG<br>Met | AAG<br>Lys | AAC<br>Asn | CAC<br>His<br>530 | AGG<br>Arg | AGC<br>Ser | GAA<br>Glu | AAC<br>Asn<br>535 | ATT<br>Ile | 1638 |
| CAA<br>Gln | TGT<br>Cys | GTC<br>Val | TAT<br>Tyr<br>540 | GCT<br>Ala | GCA<br>Ala | CAC<br>His | AAC<br>Asn | TCT<br>Ser<br>545 | GTC<br>Val | ATA<br>Ile | GAT<br>Asp | GAA<br>Glu | TGC<br>Cys<br>550 | AAG<br>Lys | | 1686 |

FIG. 3F

```
GTA ACT CTG GCA GCC AAT GGA AAG TCA GCC GAC TGC AGT GTT GAG GAA
Val Thr Leu Ala Ala Asn Gly Lys Ser Ala Asp Cys Ser Val Glu Glu
        555                     560                     565            1734

GAA CCT TGG AAA CGT GAG AAA TAAGGATATG AGTCTCAGCA AATTCTTGAA
Glu Pro Trp Lys Arg Glu Lys
        570                                                             1785

TAAACTCCCC AGCGT                                                        1800
```

FIG. 4A

```
ATAGCGGGCGA CAGCC ATG GGG AAA CCG GCG AGG AAA GGA TGC CCG AGT TGG          51
                  Met Gly Lys Pro Ala Arg Lys Gly Cys Pro Ser Trp
                   1               5                  10

AAG CGC TTC CTG AAG AAT AAC TGG GTG TTG CTG TCC ACC GTG GCC GCG            99
Lys Arg Phe Leu Lys Asn Asn Trp Val Leu Leu Ser Thr Val Ala Ala
             15                  20                  25

GTG GTG CTA GGC ATT ACC GGA GTC TTG CTT GTT CGA GAA CAC AGC AAC           147
Val Val Leu Gly Ile Thr Gly Val Leu Leu Val Arg Glu His Ser Asn
         30                  35                  40

CTC ACT TCA ACT GAG CTA AAA TAC TTC GCT TTT CCT GGA GAA ATT CTA           195
Leu Thr Ser Thr Glu Leu Lys Tyr Phe Ala Phe Pro Gly Glu Ile Leu
     45                  50                  55              60

ATG GGG ATG CTG AAA CTC ATC ATT TTG CCA TTA CCA ATA TCC AGC ATG           243
Met Gly Met Leu Lys Leu Ile Ile Leu Pro Leu Pro Ile Ser Ser Met
                 65                  70                  75

ATT ACA GGT GTT GCT CTG GCA GAT TCC AAC GTA TCC GGA AAA ATT GGT           291
Ile Thr Gly Val Ala Leu Ala Asp Ser Asn Val Ser Gly Lys Ile Gly
         80                  85                  90

CTG CGC GCT GTG GTG TAT TAT TTC TGT ACC ACC CTC ATT GCT GTT ATT           339
Leu Arg Ala Val Val Tyr Tyr Phe Cys Thr Thr Leu Ile Ala Val Ile
         95                  100                 105
```

FIG. 4B

```
CTA GGT ATT GTG CTG GTG AGC ATC AAG CCT GTC ACC CAG AAA       387
Leu Gly Ile Val Leu Val Ser Ile Lys Pro Val Thr Gln Lys
    110             115             120             125

GTG GGT GAA ATT GCG AGG GTG ACA GGC AGC ACC ATG CCT GGT GTG   435
Val Gly Glu Ile Ala Arg Val Thr Gly Ser Thr Met Pro Gly Val
125             130             135             140

GAT GCC ATG TTA GAT GCG CTC ATC AAT ATG AAT ATG AGG TTC CTC GAG GTC 483
Asp Ala Met Leu Asp Ala Leu Ile Asn Met Asn Met Arg Phe Pro Glu Val
                145             150             155

CAG GCA TGT TTT TTA CAG CTC ATT AAA ACT AAA CTT AAG CGT TTC GAG GTG GAG AAT GTC 531
Gln Ala Cys Phe Leu Gln Leu Ile Lys Thr Lys Leu Lys Arg Phe Glu Val Glu Asn Val
                160             165             170             175

CCC AGC GAT CCA GAG ATT GCA AAC ATG ACA GAA GAA TCC TTC TCA GAG 579
Pro Ser Asp Pro Glu Ile Ala Asn Met Thr Glu Glu Ser Phe Ser Glu
                    175             180             185

ATG ACT GCA ATT GGC GAT CTG TTG AAA AAA TAC TAT AAA TTG GAA GAA 627
Met Thr Ala Ile Gly Asp Leu Leu Lys Lys Tyr Tyr Lys Leu Glu Glu
190             195             200

GGC GAT TCA TCC GGC ATA GTC CTG GGC ATT GTC ATT GTC 675
Gly Asp Ser Ser Gly Ile Val Leu Gly Ile Val Ile Val
205         210             215             220

CTT GTC TTT GGA CTT ATT AAA AAA GGA ATG AAG GGA CAA ATT 723
Leu Val Phe Gly Leu Ile Lys Lys Gly Met Lys Gly Gln Ile
225             230             235
```

FIG. 4C

```
CTG GTG GAT TTC TTC AAT GCT TTG AGT GAT GCA ACC ATG AAA ATC GTT    771
Leu Val Asp Phe Phe Asn Ala Leu Ser Asp Ala Thr Met Lys Ile Val
                240             245             250

CAG ATC ATG TGT TAT ATG CCA CTA GGT ATT TTG TTC CTG ATT GCT        819
Gln Ile Met Cys Tyr Met Pro Leu Gly Ile Leu Phe Leu Ile Ala
    255             260             265

GGG AAG ATC ATA GAA GTT GAA GAC TGG GAA ATA ATT TTC CGC AAG GGC    867
Gly Lys Ile Ile Glu Val Glu Asp Trp Glu Ile Ile Phe Arg Lys Gly
270             275             280

CTT TAC ATG ACA GTC CTG ACT GGG CTT GCA ATC CAC TCC AAG CTG GTA    915
Leu Tyr Met Thr Val Leu Thr Gly Leu Ala Ile His Ser Lys Leu Val
285             290             295             300

ATT CTC ATG TAT TAT TTC ATA GTC GTA CTC CTC AAC CCT TTC ATC CGA    963
Ile Leu Met Tyr Tyr Phe Ile Val Val Leu Leu Asn Pro Phe Ile Arg
305             310             315

TTT GCC ATG GGA GCC CAG GCT CTC CTC ACA CGA AAG GCT CTG ATG TCT    1011
Phe Ala Met Gly Ala Gln Ala Leu Leu Thr Arg Lys Ala Leu Met Ser
320             325             330

TCC AGT TCA GCA ACA CTG CCT GTC ACC TTC CGC TGT GCT GAA AAT        1059
Ser Ser Ser Ala Thr Leu Pro Val Thr Phe Arg Cys Ala Leu Glu Asn
335             340             345
```

FIG. 4D

```
AAC CAG GTG GAC AAG AGG ATC ACT CGA TTC CTG TTA CCC GTT GGT GCA      1107
Asn Gln Val Asp Lys Arg Ile Thr Arg Phe Val Leu Pro Val Gly Ala
    350             355             360

ACA ATC AAC ATG GAT GGG ACC GCG CTC TAT GAA GCA GTG GCA GCG GTG      1155
Thr Ile Asn Met Asp Gly Thr Ala Leu Tyr Glu Ala Val Ala Ala Val
365             370             375                         380

TTT ATT GCA CAG TTG AAT GAC CTG TTG GGC ATT GGG CAG GCA ATC ATC      1203
Phe Ile Ala Gln Leu Asn Asp Leu Leu Gly Ile Gly Gln Ala Ile Ile
                385             390                     395

ACC ATC AGT ACG ATC GCC AGC GGA ATT GCT TCT GCC GCT CAG GGG GCT      1251
Thr Ile Ser Thr Ile Ala Ser Gly Ile Ala Ser Ala Ala Gln Gly Ala
                400                 405                         410

CCC CAG GCT GCC ATG TCT GCC CTG ATT AGT GAC GCC GGC GTG CTG GGC      1299
Pro Gln Ala Ala Met Ser Ala Leu Ile Ser Asp Ala Gly Val Leu Gly
        415             420             425

CTG GCC ATG ACC GAT GTC ACC GTG GTG GCT CTG TGG CTC GGT GGC CTG      1347
Leu Ala Met Thr Asp Val Thr Val Val Ala Leu Trp Leu Gly Gly Leu
430                             435             440

GAC CGG TTC ACC ATG AGG GTC AAC GTC GGT CTT GAT GCT TGG TTT GGG ACT  1395
Asp Arg Phe Thr Met Arg Val Asn Val Gly Leu Asp Ala Trp Phe Gly Thr
445             450             455                             460
```

FIG. 4E

```
GGC ATT GTG GAA AAG CTC TCC AAG AAG GAG CTG GAG ATG GAT GTT    1443
Gly Ile Val Glu Lys Leu Ser Lys Lys Glu Leu Glu Met Asp Val
                465             470                 475

TCA TCT GAA GTC AAC ATT GTG AAT CCC TTT GCC TTG GAA TCC ATC    1491
Ser Ser Glu Val Asn Ile Val Asn Pro Phe Ala Leu Glu Ser Ile
            480                 485                 490

CTT GAC AAC GAA GAC TCA GAC ACC AAG AAG TCT TAT GTC AAT GGA GGC 1539
Leu Asp Asn Glu Asp Ser Asp Thr Lys Lys Ser Tyr Val Asn Gly Gly
            495                 500             Thr 505

TTT GCA GTA GAC AAG TCT GAC ACC ATC TCA TTC ACC GAG TCA CAG    1587
Phe Ala Val Asp Lys Ser Asp Thr Ile Ser Phe Thr Gln Ser Gln
510                 515                 520

TTC TAGGGCCCCT GGCTGCAGAT GACTGGAAAC AAGGAAGGAC ATTTCGTGAG     1640
Phe
525

AGTCATCTCA AACACGGCTT AAGGAAAAGA GAAA                          1674
```

FIG. 5A

```
ASCT1                    MEKSNETNGLYDSAQAGPAAGPGAPGTAAGRARRCARFLRRQALVLL..TVSGVLAGAGLGAAIR.GL
GLAST1  MTKSNGEEPRMGSRMTRFQQGVRKRTLLAKKKVQNITKEDVKSYLFRNAFVLL..TVSAVIVGTILGFALRPY.
GLT1                     MASTEGANNMPKQVEVRMHDSHLSSEEPKHRNLGMRMCDKLGKNLLLSLTVFGVILGAVCGGLIRLAA
EAAC1                                                   MGKPARKGCDSKRFLKNNWLLLS.TVVAVVLGIVIGIVLVREYS

ASCT1   66   SLSRTQVTYLAFPGEMLLRMLRVIILPLVVCSLVSQAASLDASCLQRLGGIRVAYFGL.TTLSASALAVALAFI
GLAST1  72   KMSYREVKYFSFPGELLMRMLQVLVLPLISSLVTGMAALDSKASGKMGM.RAVVYMTTTIAVVIGIIIVII
GLT1    69   PIHPDVVMLIAFPGDILMRMLKVLILPLIISSLITGLSGLDAKASGRLGT.RAMVIYMSTTIAAVLGVIIVLA
EAAC1   43   NLSTLDKFYFAFPGEILMRMLKLVIIPLIVSSMITGVAAIDSNVSGKIGL.RAVLYFCTTLLAVILGIVLVS

ASCT1   130  IKPGSGAQTLQSSDLGLEDSGPPVPKETVDSFIDLARNLFPSNLVAAFRTYATDYKVV.......TONSSS
GLAST1  145  IHPGKGT.KENMYREGKIVQYTA.......ADAFLDLIRNMFPPNLVEACFKQFKTSYEKRSFKVPIQANETLLG
GLT1    142  IHPGNPKLKKQLGPGKKNDEVSS.......LDAFLDLIRNLFPENLVQACFQQIQTVTKKVLVAPPS.EEANTTK
EAAC1   116  IKPGVTQKVDEIDRTGSTPEVST.......VDAMLDLIRNMFPENLVQACFQQYKTTREEV..TASDDTGKNGTE

ASCT1   205  GNVTHEKIPIGTEI..........EGMNIIGLVLFALVLGVALKKLGSEGEDLIRFENSLNEATVLVSW
GLAST1  212  AVINNVSEAMETLTRIREEMVPVPGSVN.GVNALGIVVESMCFGFVIGNMKEQGGALREFFDSLNEAIVRLVAV
GLT1    209  AVISLINETMNEAPEETKIVIKKGLEFKDGMNVLGLIGFIAEGIAMGKMGVAGGADGGVLOMSERDCHEVSDM
EAAC1   182  ESVTAVMTTAVSENRTKEYRVVGLYS..DGINVLGLIVFCLVFGLVIGKMGEKGGIIVDFFNALSDATVKIVQI

ASCT1   265  IMWYVPVGIMFLVGSRIVEMKDIIVLVTSLGKYIFASILGHVIHGGIVLPLIYFVETRKNPERFLLGLLAPFAT
GLAST1  285  IMWYAPLGIIFLIAGKILEMEDMGVIGGQLAMYTVTVIGLIHAVIILPLIYFLVTRKNPWVFIGGLLQALIT
GLT1    283  DHVVFPAGIACLICGKIIAIKDLEVVAROLGMYMITVVGLIIHGGIFLPLIYFVVTRKNPESEFAGIFQAWIT
EAAC1   254  IMCYMPLGILFLIAGKIIEVEDWEIF.RKLGLYMVTVLSGLAIHSIVILPLIYFIVRKNPERFAMGMTQALLT

ASCT1   339  AFATCSSSATLPSMMKCIEENNGVDKRISRFILPIGATVNMDGAAIFQCVAAVFIAGLNNIELNAGQIFGILVT
GLAST1  350  ALGTSSSSATLPITFKCLEENNGVDKRITRFVLPVGATINMDGTALYEALAAIFIAGVNFDLNFGQIITSIT
GLT1    357  ALGTASSAGTLPVTFRCLEDNLGIDKRVTRFVLPVGATINMDGTALYEAVAAIFIAGMNGVILDGGOIVTVSLI
EAAC1   327  ALMISSSSATLPVTFRCAEEKNRVDKRITRFVLPVGATINMDGTALYEAVAAVFIAGLNDMDLSIGQIITISVT
```

FIG. 5B

```
413 ATASSVGAAGVPAGGVLTIATILEAIGLPTHDLPLILAVDWIVDRTTTVVNVEGDALGAGILHMLNQKATKKGE
433 ATAASIGAAGIPOAGIVTMVIVLTSVGLPTDDITLIIAVDWFLDRLRTTNVLGDSLGAGIVEHLSRHELKNRD
431 ATLASIGAASIPSAGLVTMLLILTAVGLPTEDISLLVAVDWLLDRMRTSVNVVGDSFGAGIVYHLSKSELDTID
401 ATAASIGAAGVPOAGLVTMVIVLSAVGLPAEDVTLIIAVDWLLIDRFRTVVNVLGDAFTGIVEKLSKKELEQMD

487 QELAEVKVEAIPNCKSEEETSPLVTHQNPAGPVASAPELESKESVL     532
507 VEMGNSVIEENEMKKPYQLIAQDNEPEKPVADSETKM            543
505 SQHRMHEDIEMTKTQSVYDDTKNHRESNSNQCVYAAHNSVVIDECKVTLAANGKSADCSVEEEPWKREK    573
475 VSSEVNIVNPFALESATLDNEDSDTKKSYINGGFAVDKSDTISFTQTSQF      524
```

FIG. 11

```
EAAT1         MTKSNGEEPKMGGRMERFQQGVRKRTLLAKKKVQNTKKQVKSYLFGNPFVLL..TVTAVIVGI.LGFIIRPY.
EAAT2              MASTEGANNMPKQVEVRMPDSHLGSEEPKHRMLGLRLCDKLGKNLLLTLTLVFGVTGAVCGGIIRLAS
EAAT3                                          MGKPARKGCPSWKRFLKNNWVLLS.TVAAVLGITTGVLVREHS
                                                              ─────1─────

EAAT1   72    RMSYREVKIFSPPGELIMRMLQMIVLPLITSSLVTGMAALDSKASGKMGMRAVVYMTTIAVIGIIVIII
EAAT2   69    PIMPDVVMLIAFFGDIIMRMLKMLILPLIISSLITGLSGLDAKASGRLGTRAMVYMSTIIAAVLGVILAI
EAAT3   44    NLSTLEKFYFAFPGEIIMRMLKLIIPLIISSMITGVAALDSNVSGKIGIRAVVYFGTTLIAVILGIVLVSI
                              ─────2─────                        ─────3─────

EAAT1   146   HPGKGT.KENMHREGKIVRVTAADAFLDLIRNMFPNLVEACFKQFKTGYEKRSFKVPIQANETLVGAVINNVS
EAAT2   143   HPGNPKLKKQLGPGKKNDEVSSLDAFLDLIRNLFPENLVQACFQQIQTVTKKVLVAPPPDEEANTSAEVSLN
EAAT3   118   KPGVTQKVGEIARTGSTPEVSTVDAMLDIRNMFPENLVQACFQQVKTKRFEV..KPPSDPFMNTEESFTAVM

EAAT1   219   EAMETLTRITFELVPVPGSVN.GVNALGLVVFESMCFGFVIGNMKEQGQAIREFFDSLNEAIMRLVAVIMWYAPE
EAAT2   217   ETVTEVPEETKMVIKKGLEFKDGMNVLGLIGFFIAFGIAMGKMGDQAKLMVDFFNILNEIVMKLVIMIMWYSPL
EAAT3   190   TTAISKNVTKFYKIVGMYS..DGINVLGLIVFCLVFGLVIGKMGEKGQILVDFFNALSDATMKIVQIIMCVMPL
                              ─────4─────                                      ─────5─────

EAAT1   292   GILFLIAGKIVEMEDMGVIGGQLAMYTVTIVGLLIHAVIVLPLLYFLVTRKNPWVFIGGLIQALITALGTSSS
EAAT2   291   GIACLICGKIIAIKDLEVVARQIGMYMVTVIIGLIIHGGIFLPLIYFVVTRKNPFSLFAGIFQAWITAIGTASS
EAAT3   261   GILFLIAGKIIEVEDWFIF.RKIGLYMATVLTGLAIHSIVILPLIYFIVIRKNPFRFAMGMAQALLTALMISSS
                                                      ─────6─────                    ─────7─────

EAAT1   366   SATIPITFKCLEENNGVDKRVTRFVLPVGATINMDGTALYEALAAIFIAQVNNFEINFGQIITISITATAASIG
EAAT2   385   AGTLPITFKCLEENLGIDKRVTRFVLPVGATINMDGTALYEALAAIFIAQMNGVVLDGGQIVTVSLTATLASVG
EAAT3   334   SATIPITFKCAEENNQVDKRITRFVLPVGATINMDGTALYEAVAAVFIAQLNDLDLGIGQITITSITATSASIG
                                                      ─────8─────
```

FIG. 11A

```
       ┌─9
440  AAGIPQAGLVTMVIVLTSVGLPTDDITLLIAVDWFLDRLRTTTNVLGDSLGAGIVEHLSRHELKNRDVEMGNSV
439  AASIPSAGLVTMLLIITAVGLPTEDISLLVAVDWLLIDRMRTSYNVVGDSFGAGIVYHISKSELDTIDSQMRVHE
408  AAGVPQAGIVTMVIVLSAVGLPAEDVTLIIAVDWLLDRFRIMVNVLGDAFGTGIVEKLSKKELEQMDVSSEVNI

514  IEENEMKKPYQLIAQDNLTEKPIDSETKM  542
513  DIEMTKTQSIYDDMKNHRESNSNQCVYAAHNSVIVDECKVTLAANGKSADCSVEEEPWKREK  574
482  VNPFALESTILDNEDSDTKKSYVNGGFAVDKSDTISFTQTSQF  525
```

AMINO ACID TRANSPORTERS AND USES

This is a divisional of application 08/140,729, filed Oct. 20, 1993.

This invention was made with government support under National Institute of Health giants DA07595 and DA03160. The government has certain rights to this invention.

BACKGROUND OF THE INVENTION

1. Field of the Invention

This invention relates to amino acid transporters from mammalian species and the genes corresponding to such transporters. Specifically, the invention relates to the isolation, cloning and sequencing of complementary DNA (cDNA) copies of messenger RNA (mRNA) encoding each of four novel human amino acid transporter genes. The invention also relates to the construction of recombinant expression constructs comprising such cDNAs from each of the four novel himan amino acid transporter genes of the invention, said recombinant expression constructs being capable of expressing amino acid transporter proteins in cultures of transformed prokaryotic and eukaryotic cells. Production of the transporter proteins in such cultures is also provided. The invention relates to the use of such cultures of such transformed cells to produce homogeneous compositions of each transporter protein. The invention also provides cultures of such cells producing transporter proteins for the characterization of novel and useful drugs. Antibodies against and epitopes of these transporter proteins are also provided by the invention.

2. Background of the Invention

The approximately 20 naturally-occurring amino acids are the basic building blocks for protein biosynthesis. Certain amino acids, such as glutamate and glycine, as well as amino acid derivatives such as γ-aminobutyric acid (GABA), epinephrine and norepinephrine, and histamine, are also used as signaling molecules in higher organisms such as man. For these reasons, specialized trans-membrane transporter proteins have evolved in all organisms to recover or scavenge extracellular amino acids (see Christensen, 1990, Physiol. Rev. 70: 43–77 for review).

These transporter proteins play a particularly important role in uptake of extracellular amino acids in the vertebrate brain (see Nicholls & Attwell, 1990, TiPS 11: 462–468). Amino acids that function as neurotransmitters must be scavenged from the synaptic cleft between neurons to enable continuous repetitive synaptic transmission. More importantly, it has been found that high extracellular concentrations of certain amino acids (including glutamate and cysteine) can cause neuronal cell death. High extracellular amino acid concentrations are associated with a number of pathological conditions, including ischemia, anoxia and hypoglycemia, as well as chronic illnesses such as Huntington's disease, Parkinson's disease, Alzheimer's disease, epilepsy and amyotrophic lateral sclerosis (ALS; see Pines et al., 1992, Nature 360: 464–467).

Glutamate is one example of such an amino acid. Glutamate is an excitatory neurotransmitter (i.e., excitatory neurons use glutamate as a neurotransmitter). When present in excess (>about 300 $\mu$M; Bouvier et al., 1992, Nature 360: 471–474; Nicholls & Attwell, ibid.; >5 $\mu$M for 5 min.; Choi et al., 1987, J. Neurosci. 7: 357–358), extracellular glutamate causes neuronal cell death. Glutamate transporters play a pivotal role in maintaining non-toxic extracellular concentrations of glutamate in the brain. During anoxic conditions (such as occur during ischemia), the amount of extracellular glutamate in the brain rises dramatically. This is in part due to the fact that, under anoxic conditions, glutamate transporters work in reverse, thereby increasing rather than decreasing the amount of extracellular glutamate found in the brain. The resultingly high extracellular concentration of glutamate causes neuron death, with extremely deleterious consequences for motor and other brain functions, resulting in stroke, anoxia and other instances of organic brain dysfunction.

This important role for amino acid transporters in maintaining brain homeostasis of extracellular amino acid concentrations has provided the impetus for the search for and development of compounds to modulate and control transporter function. However, conventional screening methods require the use of animal brain slices in binding assays as a first step. This is suboptimal for a number of reasons, including interference in the binding assay by non-specific binding of heterologous (i.e., non-transporter) cell surface proteins expressed by brain cells in such slices; differential binding by cells other than neuronal cells present in the brain slice, such as glial cells or blood cells; and the possibility that putative drug binding behavior in animal brain cells will differ from the binding behavior in human brain cells in subtle but critical ways. The ability to synthesize human transporter molecules in vitro would provide an efficient and economical means for rational drug design and rapid screening of potentially useful compounds.

Amino acid transporters are known in the art, and some of these proteins have been isolated biochemically and their corresponding genes have been recently cloned using genetic engineering means.

Christensen et al., 1967, J. Biol. Chem. 242: 5237–5246 report the discovery of a neutral amino acid transporter (termed the ACS transporter) in Erlich ascites tumor cells.

Makowske & Christensen, 1982, J. Biol. Chem. 257: 14635–14638 provide a biochemical characterization of hepatic amino acid transport.

Kanner & Schuldiner, 1987, CRC Crit. Rev. Biochem. 22: 1–38 provide a review of the biochemistry of neurotransmitters.

Olney et al., 1990, Science 2: 596–599 disclose that the amino acid cysteine is a neurotoxin when present in excess extracellularly.

Wallace et al., 1990, J. Bacteriol. 172: 3214–3220 report the cloning and sequencing of a glutamate/aspartate transporter gene termed gltP from *Escherichia coli* strain K12.

Kim et al., 1991, Nature 352: 725–728 report the discovery that a cationic amino acid transporter is the cell surface target for infection by ecotropic retroviruses in mice.

Wang et al., 1991, Nature 352: 729–731 report the discovery that a cationic amino acid transporter is the cell surface target for infection by ecotropic retroviruses in mice.

Maenz et al., 1992, J. Biol. Chem. 267: 1510–1156 provide a biochemical characterization of amino acid transport in rabbit jejunal brush border membranes.

Bussolati et al., 1992, J. Biol. Chem. 267: 8330–8335 report that the ASC transporter acts in an electrochemically neutral manner so that sodium ion co-transport occurs without disrupting the normal membrane potential of the cells expressing the transporter.

Engelke et al., 1992, J. Bacteriol. 171: 5551–5560 report the cloning of a dicarboxylate carrier from *Rhizobium meliloti*.

Guastella et al., 1992, Proc. Natl. Acad. Sci. USA 89: 7189–7193 disclose the cloning of a sodium ion and chloride ion-dependent glycine transporter from a glioma cell line that is expressed in the rat forebrain and cerebellum.

Kavanaugh et al., 1992, J. Biol. Chem. 267:22007–22009 report that biochemical characterization of a rat brain GABA transporter expressed in vitro in *Xenopus laevis* oocytes.

Storck et al., 1992, Proc. Natl. Acad. Sci. USA 89: 10955–10959 disclose the cloning and sequencing of a sodium ion-dependent glutamate/aspartate transporter from rat brain termed GLAST1.

Bouvier et al., ibid., disclose the biochemical characterization of a glial cell-derived glutamate transporter.

Pines et al., ibid., report the cloning and sequencing of a glial cell glutamate transporter from rat brain termed GLT1.

Kanai & Hediger, 1992, Nature 36: 467–471 disclose the cloning and sequencing of a sodium ion-dependent, high affinity glutamate transporter from rabbit small intestine termed EAAC1.

Kong et al., 1993, J. Biol. Chem. 268: 1509–1512 report the cloning and sequencing of a sodium-ion dependent neutral amino acid transporter of the A type that is homologous to a sodium-ion dependent glucose transporter.

Nicholls & Attwell, ibid., review the role of amino acids and amino acid transporters in normal and pathological brain functions.

SUMMARY OF THE INVENTION

The present invention relates to the cloning, expression and functional characterization of mammalian amino acid transporter genes. The invention comprises nucleic acids, each nucleic acid having a nucleotide sequence of a novel amino acid transporter gene. The nucleic acids provided by the invention each comprise a complementary DNA (cDNA) copy of the corresponding mRNA transcribed in vivo from each of the amino acid transporter genes of the invention. Also provided are the deduced amino acid sequences of each the cognate proteins of the cDNAs provided by the invention.

This invention provides nucleic acids, nucleic acid hybridization probes, recombinant eukaryotic expression constructs capable of expressing the amino acid transporters of the invention in cultures of transformed cells, such cultures of transformed eukaryotic cells that synthesize the amino acid transporters of the invention, homogeneous compositions of each of the amino acid transporter proteins, and antibodies against and epitopes of each of the amino acid transporter proteins of the invention. Methods for characterizing these transporter proteins and methods for using these proteins in the development of agents having pharmacological uses related to these transporter proteins are also provided by the invention.

In a first aspect, the invention provides a nucleic acid having a nucleotide sequence encoding a human neutral amino acid transporter that is the ASCT1 transporter (SEQ ID No:2).

In this embodiment of the invention, the nucleotide sequence includes 1680 nucleotides of the human ASCT1 cDNA comprising 1596 nucleotides of coding sequence, 30 nucleotides of 5' untranslated sequence and 54 nucleotides of 3' untranslated sequence. In this embodiment of the invention, the nucleotide sequence of the ASCT1 transporter consists essentially of the nucleotide sequence depicted in FIG. 1 (SEQ ID No:2). The use of the term "consisting essentially of" herein is meant to encompass the disclosed sequence and includes allelic variations of this nucleotide sequence, either naturally occurring or the product of in vitro chemical or genetic modification. Each such variant will be understood to have essentially the same nucleotide sequence as the nucleotide sequence of the corresponding ASCT1 disclosed herein.

The corresponding ASCT1 protein molecule, having the deduced amino acid sequence consisting essentially of the sequence shown in FIG. 1 (SEQ ID No.:3), is also claimed as an aspect of the invention. The use of the term "consisting essentially of" herein is as described above. Similarly, the corresponding ASCT1 protein molecule, having the deduced amino acid sequence consisting essentially of the sequence shown in FIG. 1 (SEQ ID No.:3), is also claimed as an aspect of the invention. ASCT1 protein molecules provided by the invention are understood to have substantially the same biological properties as the ASCT1 protein molecule encoded by the nucleotide sequence described herein.

In another aspect, the invention comprises a homogeneous composition of the 55.9 kD mammalian ASCT1 transporter or derivative thereof, said size being understood to be the size of the protein before any post-translational modifications thereof. The amino acid sequence of the ASCT1 transporter or derivative thereof preferably consists essentially of the amino acid sequence of the human ASCT1 transporter protein shown in FIG. 1 (SEQ ID No:3).

In a second aspect, the invention provides a nucleic acid having a nucleotide sequence encoding a human excitatory amino acid transporter that is the EAAT1 transporter (SEQ ID No:4). In this embodiment of the invention, the nucleotide sequence includes 1680 nucleotides of the human EAAT1 cDNA comprising 1626 nucleotides of coding sequence, 30 nucleotides of 5' untranslated sequence and 24 nucleotides of 3' untranslated sequence. In this embodiment of the invention, the nucleotide sequence of the EAAT1 transporter consists essentially of the nucleotide sequence depicted in FIG. 2 (SEQ ID No:4). The use of the term "consisting essentially of" herein is as described above.

In another aspect, the invention comprises a homogeneous composition of the 59.5 kilodalton (kD) mammalian EAAT1 transporter or derivative thereof, said size being understood to be the size of the protein before any post-translational modifications thereof. The amino acid sequence of the EAAT1 transporter or derivative thereof preferably consists essentially of the amino acid sequence of the human EAAT1 transporter protein shown in FIG. 2 (SEQ ID No:5). EAAT1 protein molecules provided by the invention are understood to have substantially the same biological properties as the EAAT1 protein molecule encoded by the nucleotide sequence described herein.

In a third aspect, the invention provides a nucleic acid having a nucleotide sequence encoding a human excitatory amino acid transporter that is the EAAT2 transporter (SEQ ID No:6). In this embodiment of the invention, the nucleotide sequence includes 1800 nucleotides of the human EAAT2 cDNA comprising 1722 nucleotides of coding sequence, 33 nucleotides of 5' untranslated sequence and 45 nucleotides of 3' untranslated sequence. In this embodiment of the invention, the nucleotide sequence of the EAAT2 transporter consists essentially of the nucleotide sequence depicted in FIG. 3 (SEQ ID No:6). The use of the term "consisting essentially of" herein is as described above.

The corresponding EAAT2 protein molecule, having the deduced amino acid sequence consisting essentially of the sequence shown in FIG. 3 (SEQ ID No.:7), is also claimed as an aspect of the invention. EAAT2 protein molecules provided by the invention are understood to have substantially the same biological properties as the EAAT2 protein molecule encoded by the nucleotide sequence described herein.

In another aspect, the invention comprises a homogeneous composition of the 62.1 kD mammalian EAAT2 transporter or derivative thereof, said size being understood to be the size of the protein before any post-translational modifications thereof. The amino acid sequence of the EAAT2 transporter or derivative thereof preferably consists essentially of the amino acid sequence of the human EAAT2 transporter protein shown in FIG. 3 (SEQ ID No:7).

In yet another aspect, the invention provides a nucleic acid having a nucleotide sequence encoding a human excitatory amino acid transporter that is the EAAT3 transporter (SEQ ID No:8). In this embodiment of the invention, the nucleotide sequence includes 1674 nucleotides of the human EAAT3 CDNA comprising 1575 nucleotides of coding sequence, 15 nucleotides of 5' untranslated sequence and 84 nucleotides of 3' untranslated sequence. In this embodiment of the invention, the nucleotide sequence of the EAAT3 transporter consists essentially of the nucleotide sequence depicted in FIG. 4 (SEQ ID No:8). The use of the term "consisting essentially of" herein is as described above.

The corresponding EAAT3 protein molecule, having the deduced amino acid sequence consisting essentially of the sequence shown in FIG. 4 (SEQ ID No.:9), is also claimed as an aspect of the invention. EAAT3 protein molecules provided by the invention are understood to have substantially the same biological properties as the EAAT3 protein molecule encoded by the nucleotide sequence described herein.

In another aspect, the invention comprises a homogeneous composition of the 57.2 kD mammalian EAAT3 transporter or derivative thereof, said size being understood to be the size of the protein before any post-translational modifications thereof. The amino acid sequence of the EAAT3 transporter or derivative thereof preferably consists essentially of the amino acid sequence of the human EAAT3 transporter protein shown in FIG. 4 (SEQ ID No:9).

This invention provides both nucleotide and amino acid probes derived from the sequences herein provided. The invention includes probes isolated from either cDNA or genomic DNA, as well as probes made synthetically with the sequence information derived therefrom. The invention specifically includes but is not limited to oligonucleotide, nick-translated, random primed, or in vitro amplified probes made using CDNA or genomic clone embodying the invention, and oligonucleotide and other synthetic probes synthesized chemically using the nucleotide sequence information of cDNA or genomic clone embodiments of the invention.

It is a further object of this invention to provide such nucleic acid hybridization probes to determine the pattern, amount and extent of expression of these transporter genes in various tissues of mammals, including humans. It is also an object of the present invention to provide nucleic acid hybridization probes derived from the sequences of the amino acid transporter genes of the invention to be used for the detection and diagnosis of genetic diseases. It is an object of this invention to provide nucleic acid hybridization probes derived from the DNA sequences of the amino acid transporter genes herein disclosed to be used for the detection of novel related receptor genes.

The present invention also includes synthetic peptides made using the nucleotide sequence information comprising the cDNA embodiments of the invention. The invention includes either naturally occurring or synthetic peptides which may be used as antigens for the production of amino acid transporter-specific antibodies, or used for competitors of amino acid transporter molecules for amino acid, agonist, antagonist or drug binding, or to be used for the production of inhibitors of the binding of agonists or antagonists or analogues thereof to such amino acid transporter molecules.

The present invention also provides antibodies against and epitopes of the mammalian amino acid transporter molecules of the invention. It is an object of the present invention to provide antibodies that are immunologically reactive to the amino acid transporters of the invention. It is a particular object to provide monoclonal antibodies against these amino acid transporters, must preferably the human excitatory and neutral amino acid transporters as herein disclosed. Hybridoma cell lines producing such antibodies are also objects of the invention. It is envisioned at such hybridoma cell lines may be produced as the result of fusion between a non-immunoglobulin producing mouse myeloma cell line and spleen cells derived from a mouse immunized with a cell line which expresses antigens or epitopes of an amino acid transporter of the invention. The present invention also provides hybridoma cell lines that produces such antibodies, and can be injected into a living mouse to provide an ascites fluid from the mouse that is comprised of such antibodies. It is a further object of the invention to provide immunologically-active epitopes of the amino acid transporters of the invention. Chimeric antibodies immunologically reactive against the amino acid transporter proteins of the invention are also within the scope of this invention.

The present invention provides recombinant expression constructs comprising a nucleic acid encoding an amino acid transporter of the invention wherein the construct is capable of expressing the encoded amino acid transporter in cultures of cells transformed with the construct. Preferred embodiments of such constructs comprise the human EAAT1 cDNA (SEQ ID No.:4), the human EAAT2 cDNA (SEQ ID No.:6), the human EAAT3 cDNA (SEQ ID No.:8), and human ASCT1 cDNA (SEQ ID No.:2), each construct being capable of expressing the amino acid transporter encoded therein in cells transformed with the construct.

The invention also provides cultures cells transformed with the recombinant expression constructs of the invention, each such cultures being capable of and in fact expressing the amino acid transporter encoded in the transforming construct.

The present invention also includes within its scope protein preparations of prokaryotic and eukaryotic cell membranes containing at least one of the amino acid transporter proteins of the invention, derived from cultures of prokaryotic or eukaryotic cells, respectively, transformed with the recombinant expression constructs of the invention. In a preferred embodiment, each preparation of such cell membranes comprises one species of the amino acid transporter proteins of the invention.

The invention also provides methods for screening compounds for their ability to inhibit, facilitate or modulate the biochemical activity of the amino acid transporter molecules of the invention, for use in the in vitro screening of novel agonist and antagonist compounds. In preferred embodiments, cells transformed with a recombinant expression construct of the invention are contacted with such a compound, and the effect of the compound on the transport of the appropriate amino acid is assayed. Additional preferred embodiments comprise quantitative analyses of such effects.

The present invention is also useful for the detection of analogues, agonists or antagonists, known or unknown, of the amino acid transporters of the invention, either naturally occurring or embodied as a drug. In preferred embodiments, such analogues, agonists or antagonists may be detected in blood, saliva, semen, cerebrospinal fluid, plasma, lymph, or any other bodily fluid.

Specific preferred embodiments of the present invention will become evident from the following more detailed description of certain preferred embodiments and the claims.

DESCRIPTION OF THE DRAWINGS

FIGS. 1A through 1E illustrates the nucleotide (SEQ ID No.:2) and amino acid (SEQ ID No.:3) sequences of the human ASCT1 neutral amino acid transporter.

FIGS. 2A through 2E illustrates the nucleotide (SEQ ID No.:4) and amino acid (SEQ ID No.:5) sequences of the human EAAT1 excitatory amino acid transporter.

FIGS. 3A through 3F illustrates the nucleotide (SEQ ID No.:6) and amino acid (SEQ ID No.:7) sequences of the human EAAT2 excitatory amino acid transporter.

FIGS. 4A through 4E illustrates the nucleotide (SEQ ID No.:8) and amino acid (SEQ ID No.:9) sequences of the human EAAT3 excitatory amino acid transporter.

FIGS. 5A and 5B presents an amino acid sequence comparison between human ASCT1, GLAST1, GLT1 and EAAC1.

FIGS. 11 and 11A illustrates the degree of predicted amino acid sequence homology between the novel human glutamate transporters EAAT1, EAAT2 and EAAT3; overbars indicate nine regions of hydrophobicity determined using the algorithm of Eisenberg et al., and potential sites of N-linked glycosylation are shown by the circled asparagine (N) residues.

DETAILED DESCRIPTION OF THE PREFERRED EMBODIMENTS

Figure 6A:
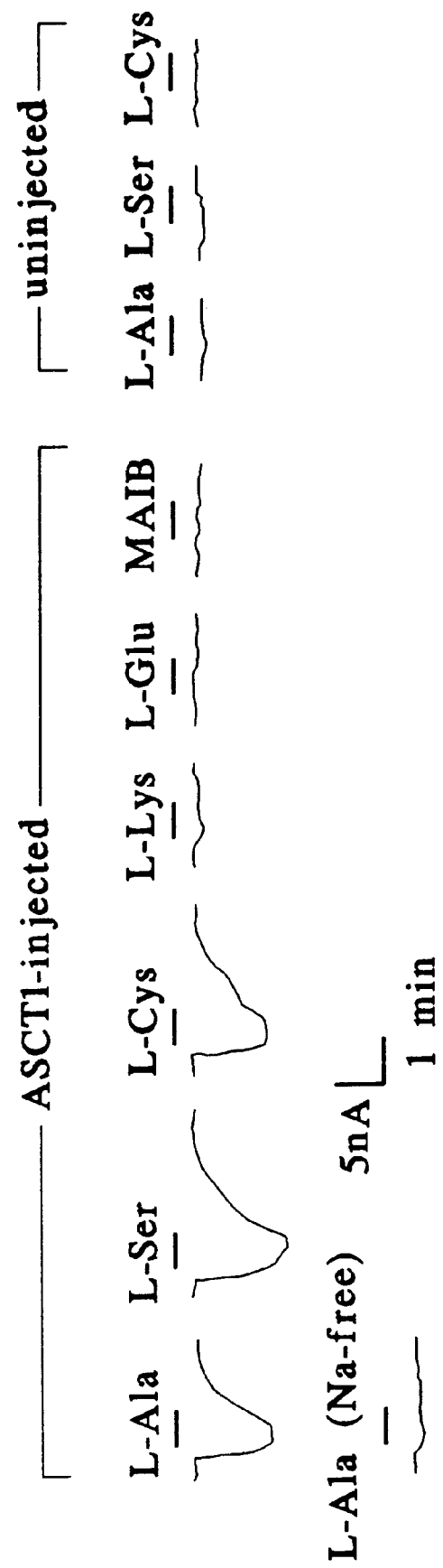
FIGS. 6A through 6C illustrates transmembrane electrochemical currents in Xenopus laevis oocytes microinjected with RNA encoding ASCT1 and contacted with the indicated amino acids (FIG. 6A); the amino acid concentration dependence of such electrochemical currents (FIG. 6B); and a plot of normalized current vs. amino acid concentration illustrating the kinetic parameters of amino acid transport (FIG. 6C).

The term "human amino acid transporter EAAT1" as used herein refers to proteins consisting essentially of, and having substantially the same biological activity as, the protein encoded by the nucleic acid depicted in FIGS. 2A through 2E (SEQ ID No.:4). This definition is intended to encompass natural allelic variations in the EAAT1 sequence. Cloned nucleic acid provided by the present invention may encode EAAT1 protein of any species of origin, including, for example, mouse, rat, rabbit, cat, and human, but preferably the nucleic acid provided by the invention encodes EAAT1 receptors of mammalian, most preferably human, origin.

The term "human amino acid transporter EAAT2 " as used herein refers to proteins consisting essentially of, and having substantially the same biological activity as, the protein encoded by the nucleic acid depicted in FIGS. 3A through 3F (SEQ ID No.:6). This definition is intended to encompass natural allelic variations in the EAAT2 sequence. Cloned nucleic acid provided by the present invention may encode EAAT2 protein of any species of origin, including, for example, mouse, rat, rabbit, cat, and human, but preferably the nucleic acid provided by the invention encodes EAAT2 receptors of mammalian, most preferably human, origin.

The term "human amino acid transporter EAAT3" as used herein refers to proteins consisting essentially of, and having substantially the same biological activity as, the protein encoded by the nucleic acid depicted in FIGS. 4A through 4E (SEQ ID No.:8). This definition is intended, to encompass natural allelic variations in the EAAT3 sequence. Cloned nucleic acid provided by the present invention may encode EAAT3 protein of any species of origin, including, for example, mouse, rat, rabbit, cat, and human, but preferably the nucleic acid provided by the invention encodes EAAT3 receptors of mammalian, most preferably human, origin.

The term "human amino acid transporter ASCT1" as used herein refers to proteins consisting essentially of, and having substantially the same biological activity as, the protein encoded by the nucleic acid depicted in FIGS. 1A through 1E (SEQ ID No.:2). This definition is intended to encompass natural allelic variations in the ASCT1 sequence. Cloned nucleic acid provided by the present invention may encode ASCT1 protein of any species of origin, including, for example, mouse, rat, rabbit, cat, and human, but preferably the nucleic acid provided by the invention encodes ASCT1 receptors of mammalian, most preferably human, origin.

Each of the nucleic acid hybridization probes provided by the invention comprise DNA or RNA consisting essentially of the nucleotide sequence of one of the amino acid transporters, depicted in FIGS. 1A through 1E, FIGS. 2A through 2E, FIGS. 3A through 3F and FIGS. 4A through 4E (SEQ ID Nos.:2,4,6,8), or any portion thereof effective in nucleic acid hybridization. Mixtures of such nucleic acid hybridization probes are also within the scope of this embodiment of the invention. Nucleic acid probes as provided herein are useful for detecting amino acid transporter gene expression in cells and tissues using techniques well-known in the art, including but not limited to Northern blot hybridization, in situ hybridization and Southern hybridization to reverse transcriptase—polymerase chain reaction product DNAs. The probes provided by the present invention, including oligonucleotides probes derived therefrom, are useful are also useful for Southern hybridization of mammalian, preferably human, genomic DNA for screening for restriction fragment length polymorphism (RFLP) associated with certain genetic disorders.

The production of proteins such as these amino acid transporter molecules from cloned genes by genetic engineering means is well known in this art. The discussion which follows is accordingly intended as an overview of this field, and is not intended to reflect the full state of the art.

DNA encoding an amino acid transporter may be obtained, in view of the instant disclosure, by chemical synthesis, by screening reverse transcripts of mRNA from appropriate cells or cell line cultures, by screening genomic libraries from appropriate cells, or by combinations of these procedures, as illustrated below. Screening of mRNA or genomic DNA may be carried out with oligonucleotide probes generated from the nucleic acid sequence information from each of the amino acid transporters disclosed herein. Probes may be labeled with a detectable group such as a fluorescent group, a radioactive atom or a chemiluminescent group in accordance with know procedures and used in conventional hybridization assays, as described in greater detail in the Examples below. In the alternative, amino acid transporter-derived nucleic acid sequences may be obtained by use of the polymerase chain reaction (PCR) procedure, using PCR oligonucleotide primers corresponding to nucleic acid sequence information derived from an amino acid transporter as provided herein. See U.S. Pat. Nos. 4,683,195 to Mullis et al. and 4,683,202 to Mullis.

Each of the amino acid transporter proteins may be synthesized in host cells transformed with a recombinant expression construct comprising a nucleic acid encoding the particular amino acid transporter cDNA. Such recombinant expression constructs can also be comprised of a vector that is a replicable DNA construct. Vectors are used herein either to amplify DNA encoding an amino acid transporter and/or to express DNA encoding an amino acid transporter gene. For the purposes of this invention, a recombinant expression construct is a replicable DNA construct in which a nucleic acid encoding an amino acid transporter is operably linked to suitable control sequences capable of effecting the expression of the amino acid transporter in a suitable host.

The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants. See, Sambrook et al., 1990, *Molecular Cloning: A Laboratory Manual* (Cold Spring Harbor Press: New York).

Vectors useful for practicing the present invention include plasmids, viruses (including phage), retroviruses, and integartable DNA fragments (i.e., fragments integratable into the host genome by homologous recombination). The vector replicates and functions independently of the host genome, or may, in some instances, integrate into the genome itself. Suitable vectors will contain replicon and control sequences which are derived from species compatible with the intended expression host. A preferred vector is pCMV5 (Andersson et al., 1989, J. Biol. Chem. 622: 8222–8229). Transformed host cells are cells which have been transformed or transfected with recombinant expression constructs made using recombinant DNA techniques and comprising nucleic acid encoding an amino acid transporter protein. Preferred host cells are COS-7 cells (Gluzman, 1981, Cell 23: 175–182). Transformed host cells may express the amino acid transporter protein, but host cells transformed for purposes of cloning or amplifying nucleic acid hybridization probe DNA need not express the transporter. When expressed, each of the amino acid transporters of the invention will typically be located in the host cell membrane. See, Sambrook et al., ibid.

Cultures of cells derived from multicellular organisms are a desirable host for recombinant amino acid transporter protein synthesis. In principal, any higher eukaryotic cell culture is useful, whether from vertebrate or invertebrate culture. However, mammalian cells are preferred, as illustrated in the Examples. Propagation of such cells in cell culture has become a routine procedure. See *Tissue Culture*, Academic Press, Kruse & Patterson, editors (1973). Examples of useful host cell lines are human 293 cells, VERO and HeLa cells, Chinese hamster ovary (CHO) cell lines, and W1138, BHK, COS-7, CV, and MDCK cell lines. COS-7 cells are preferred.

The invention provides homogeneous compositions of each of the human EAAT1, EAAT2, EAAT3 and ASCT1 amino acid transporter proteins produced by transformed eukaryotic cells as provided herein. Each such homogeneous composition is intended to be comprised of the corresponding amino acid transporter protein that comprises at least 90% of the protein in such a homogenous composition. The invention also provides membrane preparation from cells expressing each of the amino acid transporter proteins as the result of transformation with a recombinant expression construct, as described herein.

Amino acid transporter proteins made from cloned genes in accordance with the present invention may be used for screening amino acid analogues, or agonist or antagonists of amino acid transport, or for determining the amount of such agonists or antagonists in a solution of interest (e.g., blood plasma or serum). For example, host cells may be transformed with a recombinant expression construct of the present invention, an amino acid transporter expressed in those host cells, and the cells or membranes thereof used to screen compounds for their effect on amino acid transport activity. By selection of host cells that do not ordinarily express a; particular amino acid transporter, pure preparations of membranes containing the transporter can be obtained. The recombinant expression constructs of the present invention are useful in molecular biology to transform cells which do not ordinarily express a particular amino acid transporter to thereafter express this receptor. Such cells are useful as intermediates for making cell membrane preparations useful for transporter activity assays, which are in turn useful for drug screening. The recombinant expression constructs of the present invention may also be useful in gene therapy. Cloned genes of the present invention, or fragments thereof, may also be used in gene therapy carried out homologous recombination or site-directed mutagenesis. See generally Thomas & Capecchi, 1987, Cell 51: 503–512; Bertling, 1987, Bioscience Reports 7: 107–112; Smithies et al., 1985, Nature 3: 230–234.

Oligonucleotides of the present invention are useful as diagnostic tools for probing amino acid transporter gene expression in tissues of humans and other animals. For example, tissues are probed in situ with oligonucleotide probes carrying detectable groups by conventional autoradiographic techniques, to investigate native expression of this receptor or pathological conditions relating thereto. Further, chromosomes can be probed to investigate the presence or absence of the corresponding amino acid transporter gene, and potential pathological conditions related thereto.

The invention also provides antibodies that are immunologically reactive to the amino acid transporter proteins or epitopes thereof provided by the invention. The antibodies provided by the invention may be raised, using methods well known in the art, in animals by inoculation with cells that express an amino acid transporter or epitopes thereof, cell membranes from such cells, whether crude membrane preparations or membranes purified using methods well known in the art, or purified preparations of proteins, including fusion proteins, particularly fusion proteins comprising epitopes of the amino acid transporter proteins of the invention fused to heterologous proteins and expressed using genetic engineering means in bacterial, yeast or eukaryotic cells, said proteins being isolated from such cells to varying degrees of homogeneity using conventional biochemical means. Synthetic peptides made using established synthetic means in vitro and optionally conjugated with heterologous sequences of amino acids, are also encompassed in these methods to produce the antibodies of the invention. Animals that are used for such inoculations include individuals from species comprising cows, sheep, pigs, mice, rats, rabbits, hamsters, goats and primates. Preferred animals for inoculation are rodents (including mice, rats, hamsters) and rabbits. The most preferred animal is the mouse.

Cells that can be used for such inoculations, or for any of the other means used in the invention, include any cell line which naturally expresses one of the amino acid transporters provided by the invention, or any cell or cell line that expresses one of the amino acid transporters of the invention, or any epitope thereof, as a result of molecular or genetic engineering, or that has been treated to increase the expression of an endogenous or heterologous amino acid transporter protein by physical, biochemical or genetic means. Preferred cells are *E. coli* and insect SF9 cells, most preferably *E. coli* cells, that have been transformed with a recombinant expression construct of the invention encoding an amino acid transporter protein, and that express the transporter therefrom.

The present invention also provides monoclonal antibodies that are immunologically reactive with an epitope derived from an amino acid transporter of the invention, or fragment thereof, present on the surface of such cells, preferably *E. coli* cells. Such antibodies are made using methods and techniques well known to those of skill in the art. Monoclonal antibodies provided by the present invention are produced by hybridoma cell lines, that are also provided by the invention and that are made by methods well known in the art.

Hybridoma cell lines are made by fusing individual cells of a myeloma cell line with spleen cells derived from animals immunized with cells expressing an amino acid transporter of the invention, as described above. The myeloma cell lines used in the invention include lines derived from myelomas of mice, rats, hamsters, primates and humans. Preferred myeloma cell lines are from mouse, and the most preferred mouse myeloma cell line is P3X63-Ag8.653. The animals from whom spleens are obtained after immunization are rats, mice and hamsters, preferably mice, most preferably Balb/c mice. Spleen cells and myeloma cells are fused using a number of methods well known in the art, including but not limited to incubation with inactivated Sendai virus and incubation in the presence of polyethylene glycol (PEG). The most preferred method for cell fusion is incubation in the presence of a solution of 45% (w/v) PEG-1450. Monoclonal antibodies produced by hybridoma cell lines can be harvested from cell culture supernatant fluids from in vitro cell growth; alternatively, hybridoma cells can be injected subcutaneously and/or into the peritoneal cavity of an animal, most preferably a mouse, and the monoclonal antibodies obtained from blood and/or ascites fluid.

Monoclonal antibodies provided by the present invention are also produced by recombinant genetic methods well known to those of skill in the art, and the present invention encompasses antibodies made by such methods that are immunologically reactive with an epitope of an amino acid transporter of the invention. The present invention also encompasses fragments, including but not limited to F(ab) and F(ab)$_2$ fragments, of such antibody. Fragments are produced by any number of methods, including but not limited to proteolytic cleavage, chemical synthesis or preparation of such fragments by means of genetic engineering technology. The present invention also encompasses single-chain antibodies that are immunologically reactive with an epitope of an amino acid transporter, made by methods known to those of skill in the art.

The present invention also encompasses an epitope of an amino acid transporter of the invention, comprised of sequences and/or a conformation of sequences present in the transporter molecule. This epitope may be naturally occurring, or may be the result of proteolytic cleavage of a transporter molecule and isolation of an epitope-containing peptide or may be obtained by synthesis of an epitope-containing peptide using methods well known to those skilled in the art. The present invention also encompasses epitope peptides produced as a result of genetic engineering technology and synthesized by genetically engineered prokaryotic or eukaryotic cells.

The invention also includes chimeric antibodies, comprised of light chain and heavy chain peptides immunologically reactive to an amino acid transporter-derived epitope. The chimeric antibodies embodied in the present invention include those that are derived from naturally occurring antibodies as well as chimeric antibodies made by means of genetic engineering technology well known to those of skill in the art.

The Examples which follow are illustrative of specific embodiments of the invention, and various uses thereof. They set forth for explanatory purposes only, and are not to be taken as limiting the invention.

EXAMPLE 1

Isolation of a Human Neutral Amino Acid Transporter cDNA

In order to clone a novel human neutral amino acid transporter, a cDNA library was prepared from human motor cortex mRNA using standard techniques [see Sambrook et al., 1990, *Molecular Cloning: A Laboratory Manual* (Cold Spring Harbor Press: New York)]. Briefly, total RNA was isolated using the method of Chomczynski & Sacchi (1987, Anal. Biochem. 162: 156–159), wherein the tissue is disrupted and solubilized in a solution containing guanidinium isothiocyanate and the RNA purified by phenol/chloroform extractions. Total cellular RNA thus isolated was then enriched for poly (A$^+$) mRNA by oligo (dT) chromatography. A mixture of oligo (dT)-primed and random-primed mRNA was converted to cDNA; using the Superscript Choice System (Bethesda Research Labs, Gaithersburg, Md.). cDNA was ligated into the cloning vector λZAPII (Strategene, La Jolla, Calif.), packaged into phage beads using commercially-available packaging extracts (Strategene) and used to infect *E. coli*. Lawns of infected bacterial cells were used to make plaque lifts for hybridization using standard conditions (see Sambrook, et al., ibid.).

This CDNA library was hybridized with a $^{32}$P-labeled oligonucleotide having the following sequence:

5'-CTG(A/G)GC(A/G)ATGAA(A/G)ATGGCAGCCAGGGC(C/T)TCATACAGGGCTGTGCC-(A/G)TCCATGTT(A/G)ATG-GT(A/G)GC-3' (SEQ ID NO:1).

(This oligonucleotide was obtained commercially from Oligos, Etc., Wilsonville, Oreg.). This oligonucleotide was chosen on the basis of shared homology between a cloned rat glutamate transporter gene (GLAST1) and the bacterial glutamate transporter gene gltP (see Storck et al, ibid. and Wallace et al., ibid.), which suggested an important and conserved structural motif. Hybridization was performed at 50° C. in a solution containing 0.5M Na$_2$HPO$_4$ (pH 7.15)/7% sodium dodecyl sulfate (SDS) and the filters were washed at 60 20 C. in 2X SSPE [0.36M NaCl/20 mM sodium phosphate (pH 7.7)/2 mM ethylenediamine tetraacetic acid (EDTA)] and 1% SDS. Hybridizing clones were identified by autoradiography at −70° C. using tungsten-containing intensifying screens (DuPont-NEN, Wilmington, Del.).

More than 20 positively-hybridizing clones were detected in screening experiments using the above-described primer. One of these clones was excised from the cloning vector in vitro by superinfection with a defective filamentous phage that recognizes and excises cloned insert sequences along with adjacent modified phage replication-form sequences (termed pBluescript SK and available from Strategene). This clone contained a 2.7 kilobase (kb) insert, which was sequenced using the dideoxy-chain termination method of Sanger et al. (1977, Proc. Natl. Acad. Sci. USA 74: 5463), using Sequenase 2.0, a modified form of bacteriophage T7 DNA polymerase (U.S. Biochemical Corp., Cleveland, Ohio). The nucleotide sequence of the portion of this clone containing an open reading frame (encoding the ASCT1 gene) is shown in FIGS. 1A through 1E.

This ASCT1 clone (SEQ ID No.:2) was found to be comprised of about 180 bp of 5' untranslated region, about 900 bp of 3' untranslated region and an open reading frame of 1596 bp encoding the ASCT1 transporter protein (comprising 532 amino acids). The initiator methionine codon was found to be the first methionine codon 3' to an in-frame stop codon and embedded within the consensus sequence for eukaryotic translation initiation (see Kozak, 1987, Nucleic Acids Res 15: 8125–8132). The ASCT1 amino acid sequence (SEQ ID No.:3; also shown in FIGS. 1A through 1E) was found to exhibit similarity to other known glutamate transporter subtypes (an amino acid sequence comparison is shown in FIGS. 5A through 5B). An amino acid comparison between glutamate transporters from rat (GLAST1 and GLT-1) and rabbit (EAAC1) showed 39%, 34% and 39% sequence identity (respectively) between these amino acid transporter proteins (shown in FIGS. 5A and 5B by shaded boxes). This degree of sequence identity is comparable to the sequence identity between these glutamate subtypes themselves. Both the amino and carboxyl termini were found to be divergent between these transporter proteins, and diversity was also found in the extracellular domains of these putative protein sequences, which contain conserved potential N-glycosylation sites (shown in FIGS. 5A and 5B by open boxes). It was noted that a highly conserved sequence (comprising the amino acids —LYEA—) in the glutamate transporters was replaced by the unrelated amino acid sequence —IFQC— in the ASCT1 sequence (at positions 385–387 of the ASCT1 amino acid sequence shown in FIGS. 5A and 5B). 6–10 putative transmembrane domains were found using the algorithm of Eisenberg et al. (1984, J. Molec. Biol. 179: 125–142). On the basis of these data ASCT1 was determined to encode a related but distinct and novel member of the amino acid transporter family.

EXAMPLE 2

Isolation of Human Excitatory Amino Acid Transporter cDNA

The remaining (>20) positively-hybridizing clones from the human motor cortex cDNA library detected by hybridization with the primer described in Example 1 (SEQ ID No.:1) were isolated and the corresponding plasmids obtained by in vivo excision after superinfection with defective phage as described in Example 1 above. These resulting plasmids were isolated and purified using conventional techniques (see Sambrook et al., ibid.). Four classes of clones were distinguished based on differential hybridization experiments using each clone as a hybridization probe against a panel of the remaining clones one after another, where conditions of hybridization stringency were varied to distinguish between each of the classes.

Representative clones from each class were sequenced as described in Example 1. One class of clones represented the ASCT1 cDNA sequences described in Example 1. The other three classes were found to encode novel proteins having amino acid sequences homologous to but distinct from the human ASCT1 sequence. Clone GT5 was determined to contain a 4.0 kb insert encoding a protein having a predicted amino acid sequence (termed EAAT1; SEQ ID No.:4) homologous to but distinct from the rat GLAST1 cDNA clone of Storck et al. (ibid.). Clone GT13 was determined to contain a 2.5 kb insert comprising an open reading fame corresponding to a full-length coding sequence for a novel human transporter gene termed EAAT2 (SEQ ID No.:6). Clone GT11 was found to contain a partial sequence of another novel human transporter termed EAAT3. The EAAT3 clone was used to re-screen the cDNA library described in Example 1. The result of these re-screening experiments was the isolation of Clone GT11B containing a full-length open reading frame encoding EAAT3 (SEQ ID No.:8).

FIGS. 11 and 11A shows the results of alignment of the predicted amino acid sequences of the three novel glutamate transporters of the invention. Nine regions of Eisenberg algorithm predicted hydrophobicity are denoted by overlining, and potential sites of N-linked glycosylation (consensus sequence N-X-S/T, where X is any amino acid) are indicated by the circles asparagine (N) residues. EAAT1 shares 47% (253/542) amino acid sequence identity with EAAT2 and 46% (262/574) sequence identity with EAAT3, whereas the EAAT2 sequence is 45% (259/574) identical to the predicted EAAT3 sequence. Cross-species comparisons of the predicted amino acid sequences of these novel human glutamate transporters revealed the following relationships: EAAT1 was found to be 96% homologous with the rat GLAST1 sequence (Storck et al., ibid.); EAAT2 was found to be 90% homologous with the rat GLT1 sequence (Pines et al., 1992, ibid.); and EAAT3 was found to be 93% homologous with the, rabbit EAAC1 sequence (Kanai & Hefter, 1992, ibid.). These results indicate that EAAT1, EAAT2 and EAAT3 are related but distinct members of the glutamate transporter family of amino acid transporters.

EXAMPLE 3

Functional Expression of the ASCT1 Amino Acid Transporter Gene in Xenopus Oocytes The sequence similarity between ASCT1 and the glutamate transporters GLAST1, EAAC1 and GLT-1 suggested that the protein encoded by ASCT1 was an amino acid transporter. The ability of the ASCT1 gene product to transport amino acids, and the identity of which amino acids might be transported by this gene product, was assayed in Xenopus laevis oocytes following microinjection of in vitro synthesized ASCT1 RNA.

Briefly, the coding sequence of the ASCT1 cDNA was isolated with unique flanking restriction sites using a PCR-based assay. In this assay, each of the complementary primers used for PCR amplification of the coding sequence contained a sequence encoding a unique restriction enzyme recognition site at the 5' terminus of each PCR primer. For ASCT1, the sense primer contained a KpnI recognition sequence (GGTAC C), and the antisense primer contained an XbaI recognition sequence ( CTAGA) at their respective 5' termini. Each of the PCR primers used for amplifying ASCT1 sequences had the following sequence:

ASCT1 sense primer:

5'-CGCGGGTACCGCCATGGAGAAGAGC AAC-3' (SEQ ID NO:10);

ASCT1 antisense primer:

5'-CGCGTCTAGATCACAGAACCGACTCC TTG-3' (SEQ ID NO: 11).

PCR amplification was performed for 30 cycles, each cycle comprising 1 minute at 94° C., 30 seconds at 55° C. and 2 minutes at 72° C. Following the PCR, the product of the amplification reaction was purified using standard techniques (Saiki et al., 1988, Science 239: 487–491). The DNA then digested with the restriction enzymes KpnI and XbaI and the cloned into the polylinker of an oocyte transcription vector (pOTV; see Wang et al., 1991, Nature 352: 729–731) that had been digested with KpnI and XbaI. Synthetic RNA was then transcribed in vitro from this clone using the method of Kavanaugh et al. (1992, J. Biol. Chem. 267: 22007–22009) employing bacteriophage T7 RNA polymerase (New England Biolabs, Beverly, Mass.). 20–50 nL of ASC1 RNA (at a concentration of about 400 $\mu$g/mL) was injected into defolliculated stage V–VI Xenopus oocytes excised from female *Xenopus laevis* anesthetized by immersion in 3-aminobenzoic acid for 60 min. Excised oocytes were treated with collagenase II (Sigma Chemical Co., St. Louis, Mo.) in calcium-free Barth's saline solution [comprising 88 mM NaCl, 1 mM KCl, 2.4 mM NaHCO$_3$, 0.82 mM MgSO$_4$, 7.5 mM Tris-HCl (pH 7.6), 50U/mL Nystatin (Sigma) and 0.1 mg/mL gentamycin (Sigma)] for 60 min., and then incubated overnight at 15° C. in 50% Leibowitz's L-15 media (Grand Island Biological Co. (GIBCO), Long Island, N.Y.). After overnight incubation the oocytes were mechanically defolliculated and then were injected with ASCT-1 RNA and incubated at 19° C. for 48 h (see Kim et al., 1991, Nature 352: 725–728 for further details of Xenopus oocyte preparation and microinjection).

Amino acid transport in such oocytes was assayed using [$^3$H] alanine, [$^3$H] serine or[$^{35}$S] cysteine (obtained from New England Nuclear, Boston, Mass.). Briefly, microinjected oocyte were patch-clamped at –60 mV using a Dagan TEV-200 clamp amplifier with an Axon Instruments (Foster City, Calif.) TL-1 A/D interface controlled by pCLAMP software (Axon Instruments) (see Kavanaugh et al., 1992, J. Biol. Chem. 267: 22007–22009 for a detailed review of this methodology) and continuously superfused with ND-96 buffer (consisting of 96 mM NaCl/2 mM KCl/1.8 mM CaCl$_2$/1 mM MgCl$_2$/5 mM HEPES, pH 7.5). For transport measurements, this solution was changed to a solution containing varying concentrations of the radiolabeled amino acids in ND-96 buffer.

Figure 6B:
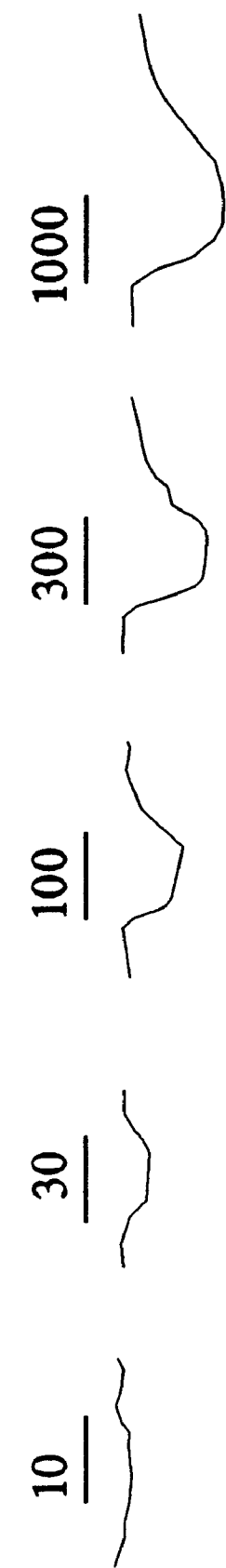
Figure 6C:
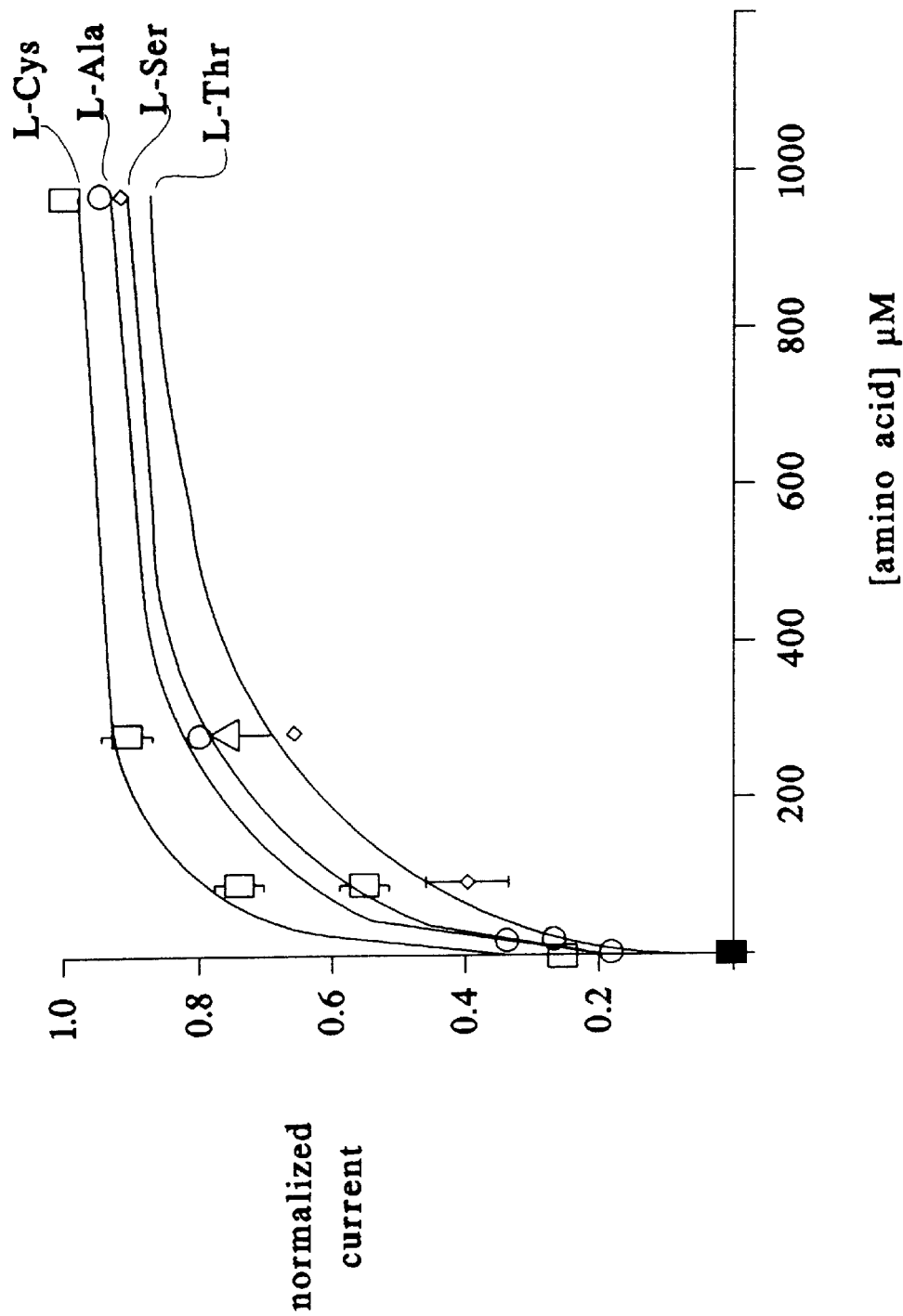

Three types of experiments were performed, the results of each being shown in FIGS. 6A through 6C. As shown in FIG. 6A, when such oocytes were contacted with ND-96 buffer containing L-alanine, L-serine or L-cysteine, a hyperpolarization of the cell plasma membrane was produced as the result of inward currents of Na$^+$ion, as has been associated with other known amino acid transporters (see Nicholls, ibid.). In contrast, the amino acids L-lysine, L-glutamine, proline, glycine, methionine, arginine, glutamine, asparagine, and leucine, and the amino acid analogues N-methylalanine, had no effect at much higher concentrations (i.e., about 1 mM). Another amino acid analogue, 2-methylaminoisobutyric acid (MAIB), which is known to be specific for the amino acid transporter type A (Christensen et al., 1967, J. Biol. Chem. 242: 5237–5246), also had no effect at concentrations of 1 mM. Further, in competition experiments, contacting such oocytes with a solution containing MAIB at a concentration of 10 mM had no effect on the rate of uptake of [$^3$H] alanine present at 100 $\mu$M. The response of the oocytes was also stereospecific (D-alanine was found to produce only 12±3% of the response produced by treatment of these oocytes with L-alanine) and Na$^+$ ion-specific (no response was detected when Na$^+$ ions were replaced by tris-hydroxyethylaminomethane buffer, shown in FIG. 6A). The rate of radiolabeled amino acid uptake (in pmol/min per oocyte, determined at an amino acid concentration of 100 $\mu$M) for the amino acids alanine, cysteine and serine are shown in Table I.

The uptake currents measured in ASCT1-injected oocytes were found to be both dose-dependent and saturable. FIG. 6B, illustrates the dose-dependency of the electrochemical response of ASCT1-injected oocytes to L-alanine. The intensity of the response (equivalent to the amount of current flow into the cell) increased with the concentration of L-alanine from 10 $\mu$M to 1 mM. The saturability of this response is shown in FIG. 6C. In this Figure, the current, normalized to the maximum response obtained with L-alanine, is shown plotted against the extracellular amino acid concentration of each amino acid tested. For the L-stereoisomers of alanine, serine, cysteine and threonine, the inward current flux was found to saturate and reach a plateau at concentrations from 400–1000 $\mu$M. More detailed analyses of the kinetics of amino acid influx were performed by least squares linear regression analysis of induced inward current ([T]) plotted as a function of substrate amino acid concentration ([S]), using the equation shown in the legend of Table II. Data were averaged from all oocytes tested, and the results expressed as the mean±standard error are shown in Table II.

These results indicated that the cloned ASCT1 cDNA derived from human motor cortex mRNA encoded an amino acid transporter that was specific for Alanine, Serine, Cysteine (and Threonine) and that amino acid transport activity was accompanied by an inward current flow mediated by sodium ions. These results demonstrated that the novel amino acid transporter isolated herein was related to but distinct from other, known transporters, such as the so-called ASC amino acid transporters (Christensen et al., ibid.).

EXAMPLE 4

Functional Expression of the Glutamate Amino Acid Transporter Genes In Xenous Oocytes Similar series of experiments were performed using RNA synthesized in vitro from constructs containing each of the cloned glutamine transporter genes of the invention. In these experiments, each of the PCR primers used to amplify each of the glutamate transporter genes had the following sequence:

EAAT1 sense primer:

5'-CGCGGGTACCAATATGACTAAAAGC AATG-3' (SEQ ID NO:12);

EAAT1 antisense primer:

5'-CGCGTCTAGACTACATCTTGGTTTCA
CTG-3'   (SEQ ID NO:13);

EAAT2 sense primer:

5'-CGCGGGTACCACCATGGCATCTACGG
AAG-3'   (SEQ ID NO:14);

EAAT2 antisense primer:

5'-CGCGTCTAGATTATTTCTCACGTTTCC
AAG-3'   (SEQ ID NO:15)

EAAT3 sense pimer:

5'-CGCGGGTACCGCCATGGGGAAACCGG
CG-3'   (SEQ ID NO:16);

EAAT3 antisense primer:

5'-CGCGGGATCCCTAGAACTGTGAGGTC
TG-3'   (SEQ ID NO:17).

As can be determined by inspection of these sequences, each of the sense primers contained a KpnI recognition sequence (GGTAC C), and each of the antisense primers contained an XbaI recognition sequence (T CTAGA) at the 5' terminus of each primer for EAAT1 and EAAT2. For EAAT3, the sense primer contained a KpnI recognition sequence, and the antisense primer contained a BamHI recognition sequence (G GATCC) at the 5' terminus of each primer.

PCR amplification was performed for 30 cycles, each cycle comprising 1 minute at 94° C., 30 seconds at 50° C. and 2 minutes at 72° C.. Following the PCR, each of the PCR products was isolated and cloned into pOTV as described in Example 3, from which RNA encoding each glutamate transporter was- synthesized in vitro as described.

Figure 12A:
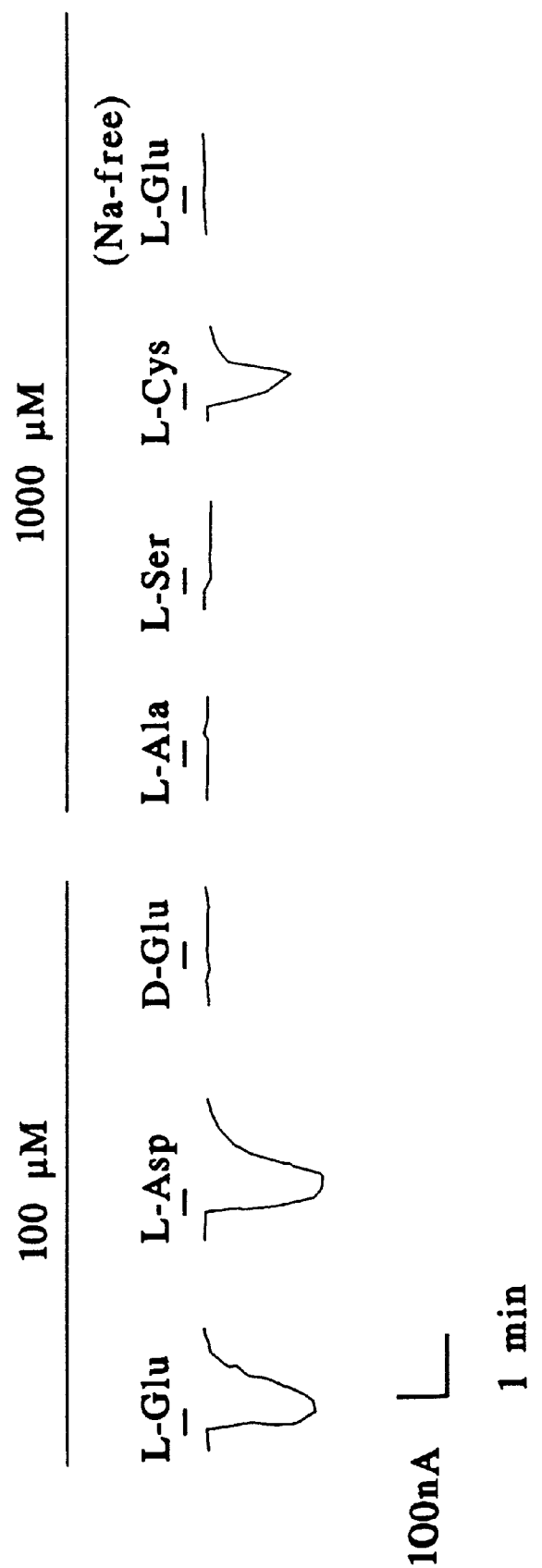
FIGS. 12A through 12C illustrate electrogenic uptake of various amino acids (FIG. 12A) and the concentration dependence of such uptake of L-glutamate (FIGS. 12B and 12C) in Xenopus laevis oocytes expressing the EAAT1 amino acid transporter.
Figure 12B:
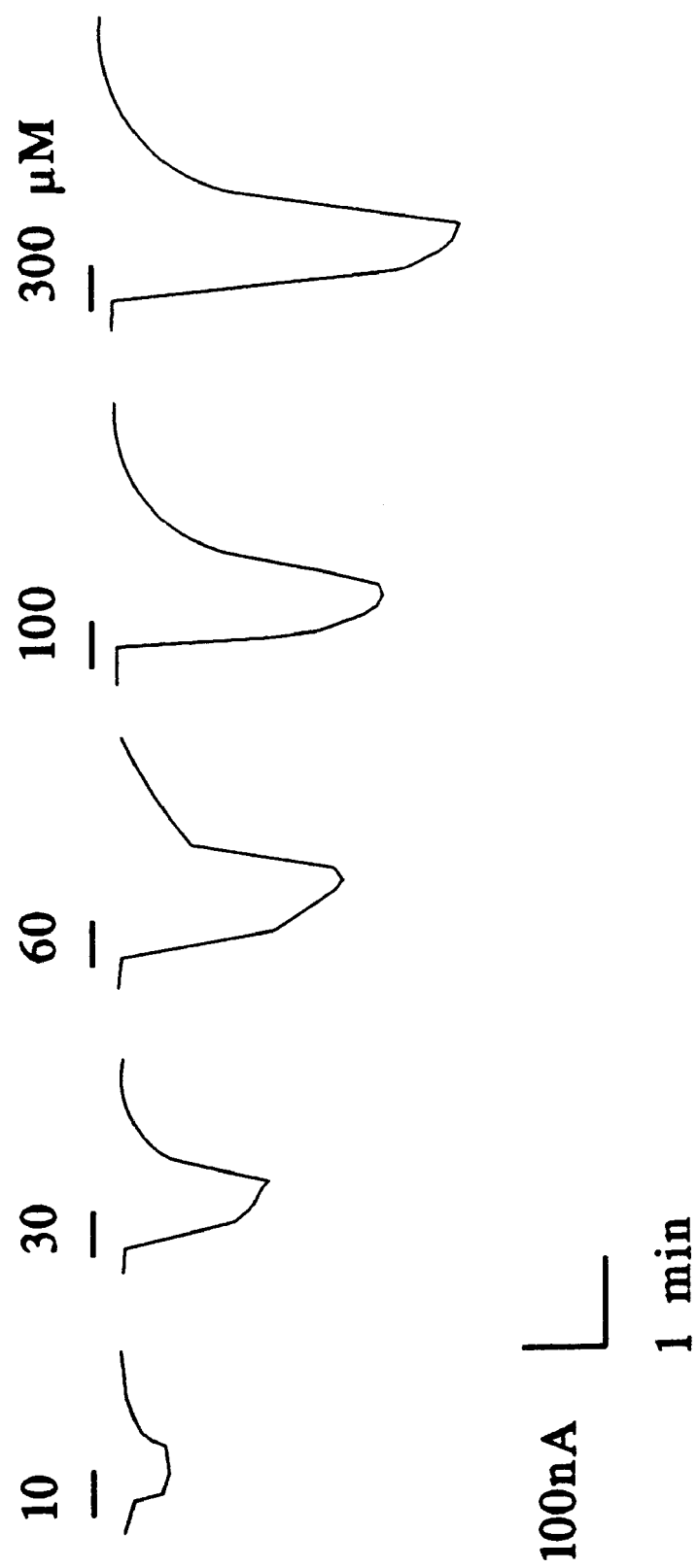
Figure 12C:
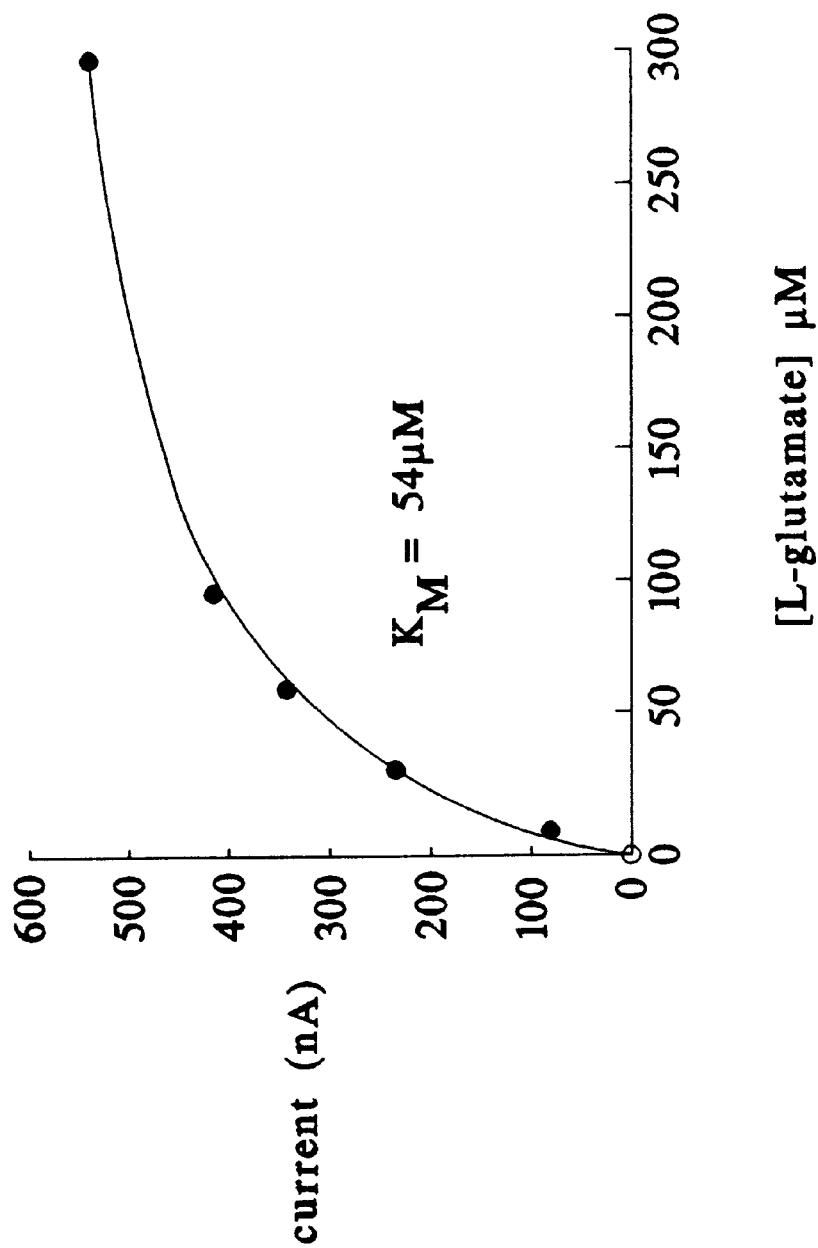

Such RNA preparations were each introduced into Xenopus oocytes as described in Example 3 to enable expression therein. Amino acid uptake experiments were performed on such oocytes expressing each of the glutamate transporters, also as described in Example 3. Results of such experiments are shown in FIG. 12A through 12C. FIG. 12A shows electrogenic uptake of various amino acids in EAAT1-expressing oocytes. Both L-glutamate and L-aspartate caused inward currents as high as several microamps when added to the incubation media (ND-96) at a concentration of 100 μM. In contrast, incubation of EAAT1-expressing oocytes with L-alanine and L-serine at ten-fold higher concentrations (i.e., 1000 μM) did not result in electrogenic uptake of these amino acids. Uptake was found to be stereospecific, since L-glutamate incubation did not result in the generation of an inward electric current, and sodium-ion specific, since electrogenic uptake of L-glutamate was abolished by incubation in sodium ion-free media (choline was used to replace sodium in these incubations).

These experiments also demonstrated the surprising result that cysteine, when present at high enough extracellular concentrations (i.e., 1000 μM) was capable of being electrogenically transported by the EAAT1 transporter. Cysteine had not previously been reported to be a glutamate transporter substrate; however, amino acid sequence analysis of the EAAT1 transporter showed structural similarities between EAAT1 and the ASCT1 transporter, which was demonstrated herein to transport cysteine (see Example 3). As will be discussed in detail below, the EAAT1 transporter displays a $K_m$ for glutamate of 54 μM; in contrast, the $K_m$ for cysteine was found to be 300 μM. The EAAT1 transporter thus displays a pattern of substrate specificity that is distinct from that of any known glutamate transporter.

FIG. 12B illustrates the results of biochemical analysis of substrate affinity of the EAAT1 transporter for glutamate, said results being plotted as current versus substrate concentration to yield an estimate of the $K_m$. These experiments were performed essentially as described for the ASCT1 transporter in Example 3. Patch-clamped oocytes expressing the EAAT1 transporter were incubated with varying extracellular concentrations of L-glutamate, and the magnitude of the resulting inward currents determined. From these experiments, the plotted relationship between the magnitude of the inward current and the extacellular L-glutamate concentration was determined, resulting in an estimate for $K_m$ equal to 54 μM for L-glutamate. These results were in good agreement with results obtained in COS-7 cells expressing the EAAT1 transporter, described hereinbelow (see Example 5).

EXAMPLE 5

Functional Expression of the Amino Acid Transporter Genes in COS-7 Cells

DNA fragments comprising the coding sequences of the novel glutamate transporter genes of the invention were excised from the pOTV constructs described in Example 3 and subcloned into the mammalian expression plasmid pCMV5 (Anderson et al., 1989, J. Biol. Chem. 264: 8222–8229). These mammalian expression constructs were used for transient expression assays of glutanate transporter protein function after transfection of each of these constructs into COS-7 cells (Gluzman, 1981, Cell 23: 175–182).

Each of the pCMV5 constructs corresponding to EAAT1, EAAT2 and EAAT3 were introduced into COS-7 cells by DEAE-dextran facilitated transfection (see Sambrook et al., ibid.). Two day following transfection, the transfected cells were washed three times in phosphate-buffered saline (PBS) and then incubated with a mixture of radiolabeled amino acid ($[^{31}H]$-L-glutamate or $[^{31}H]$-D-aspartate; Dupont-NEN) and non-radiolabeled amino acid for 10 min. After incubation, the cells were washed three times with ice-cold PBS, solubilized with a solution of 0.1% sodium dodecyl sulfate (SDS) and the amount of radioactivity associated with the cells determined using standard liquid scintillation counting methods. The results of these experiments showed that cells transfected with each of the glutamate transporter constructs accumulated significantly-higher (between 10 and 100-fold higher) amounts of radioactivity than did mock (i.e., pCMV5 plasmid) transfected COS-7 cells (which accumulation represented endogenous COS-7 cell uptake of radioactive glutamate). The course of radioactive glutamate uptake was found to be linear for at least 20 min in assays performed at room temperature.

Figure 7A:
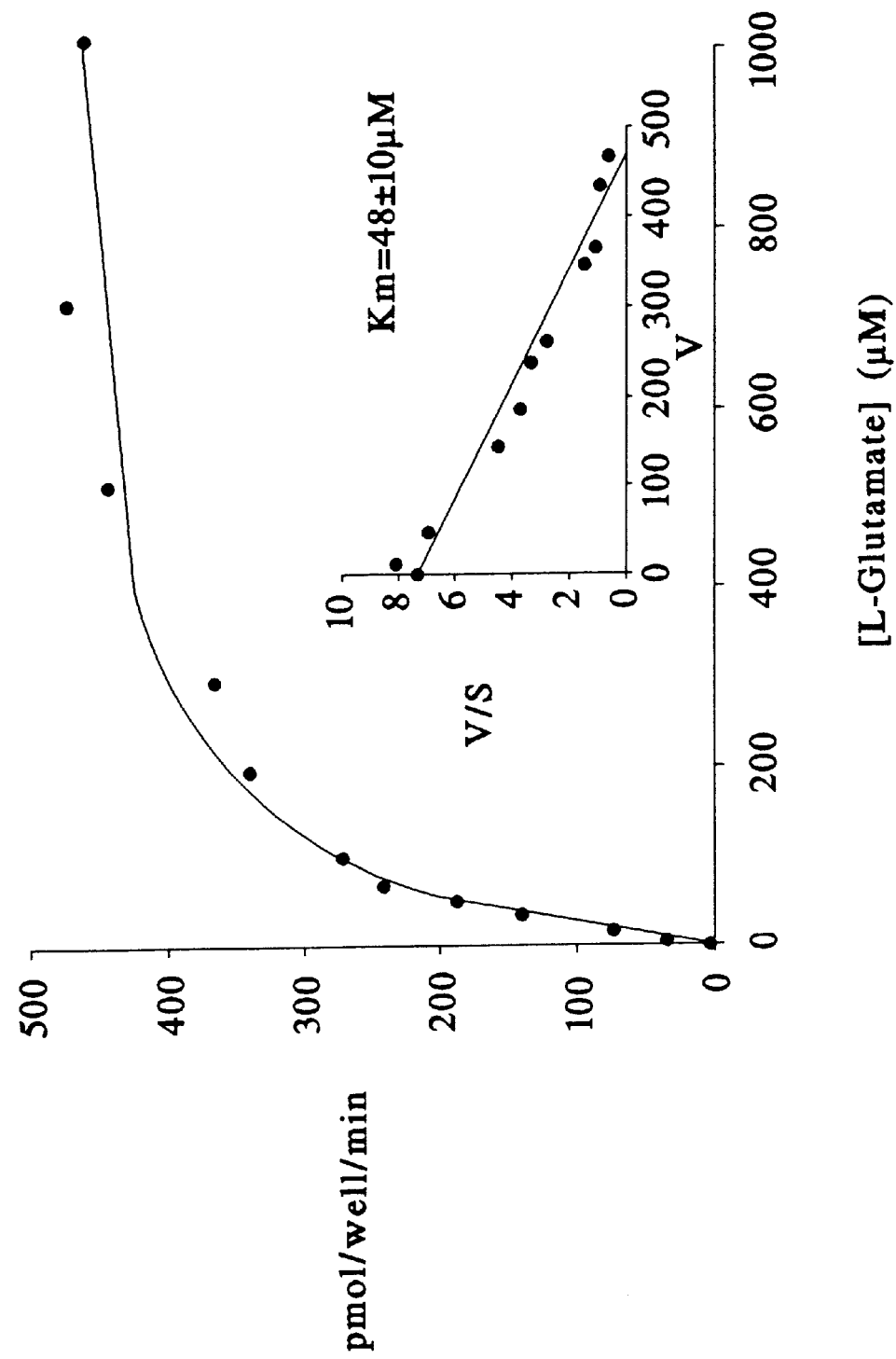
FIGS. 7A through 7F presents glutamate transporter kinetics of EAAT1 (FIGS. 7A and 7B), EAAT2 (FIGS. 7C and 7D) and EAAT3 (FIGS. 7E and 7F).
Figure 7B:
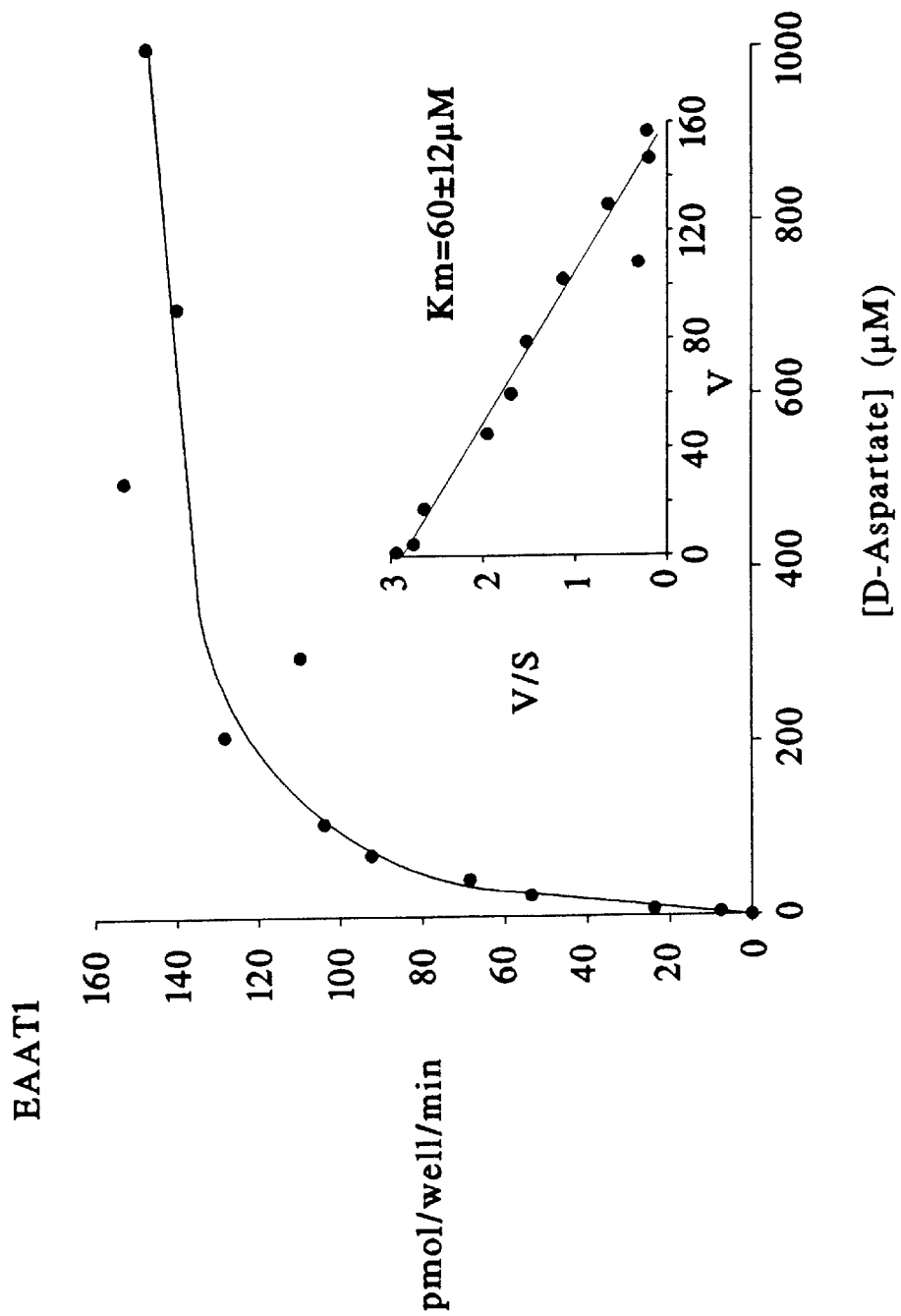
Figure 7C:
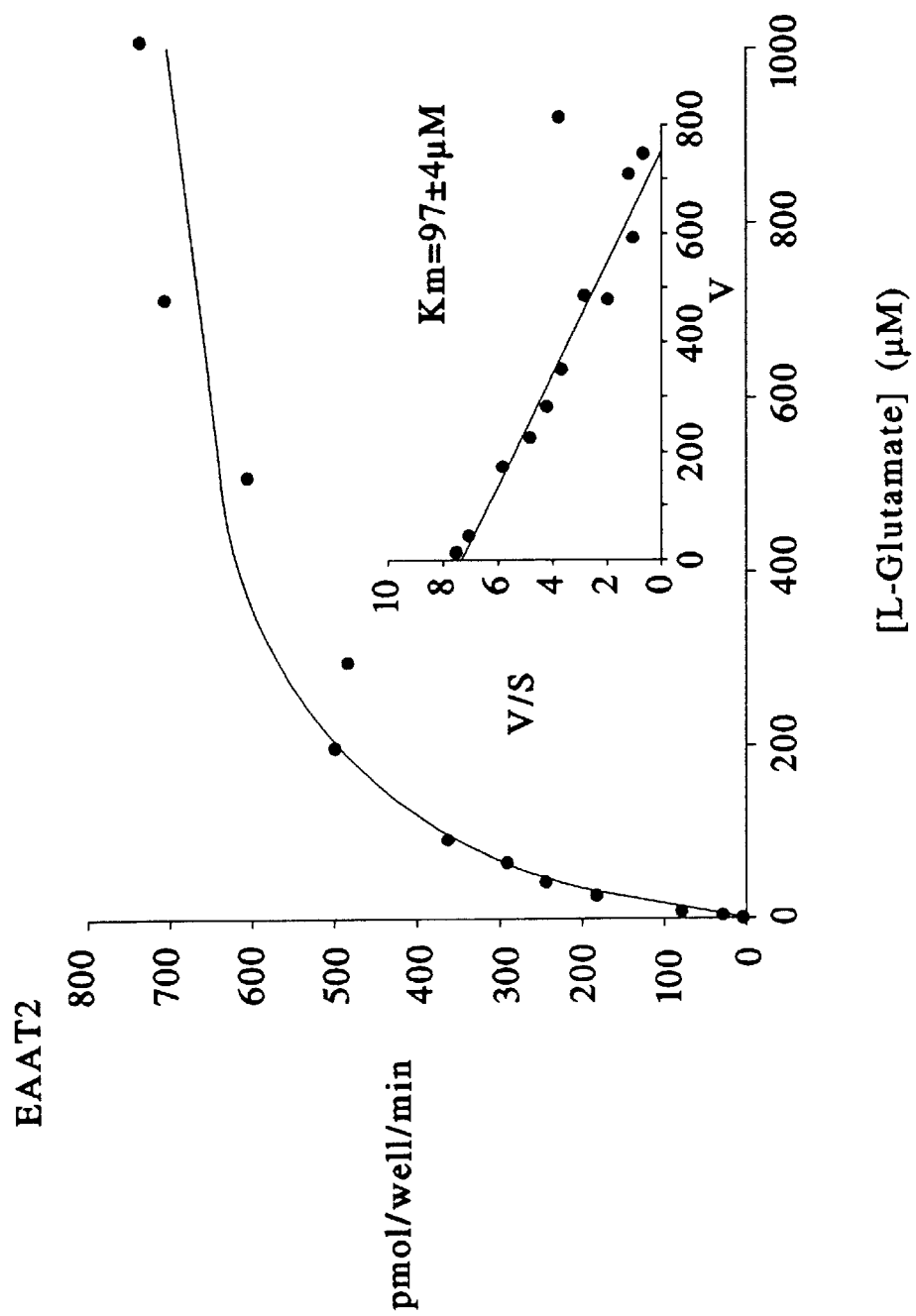
Figure 7D:
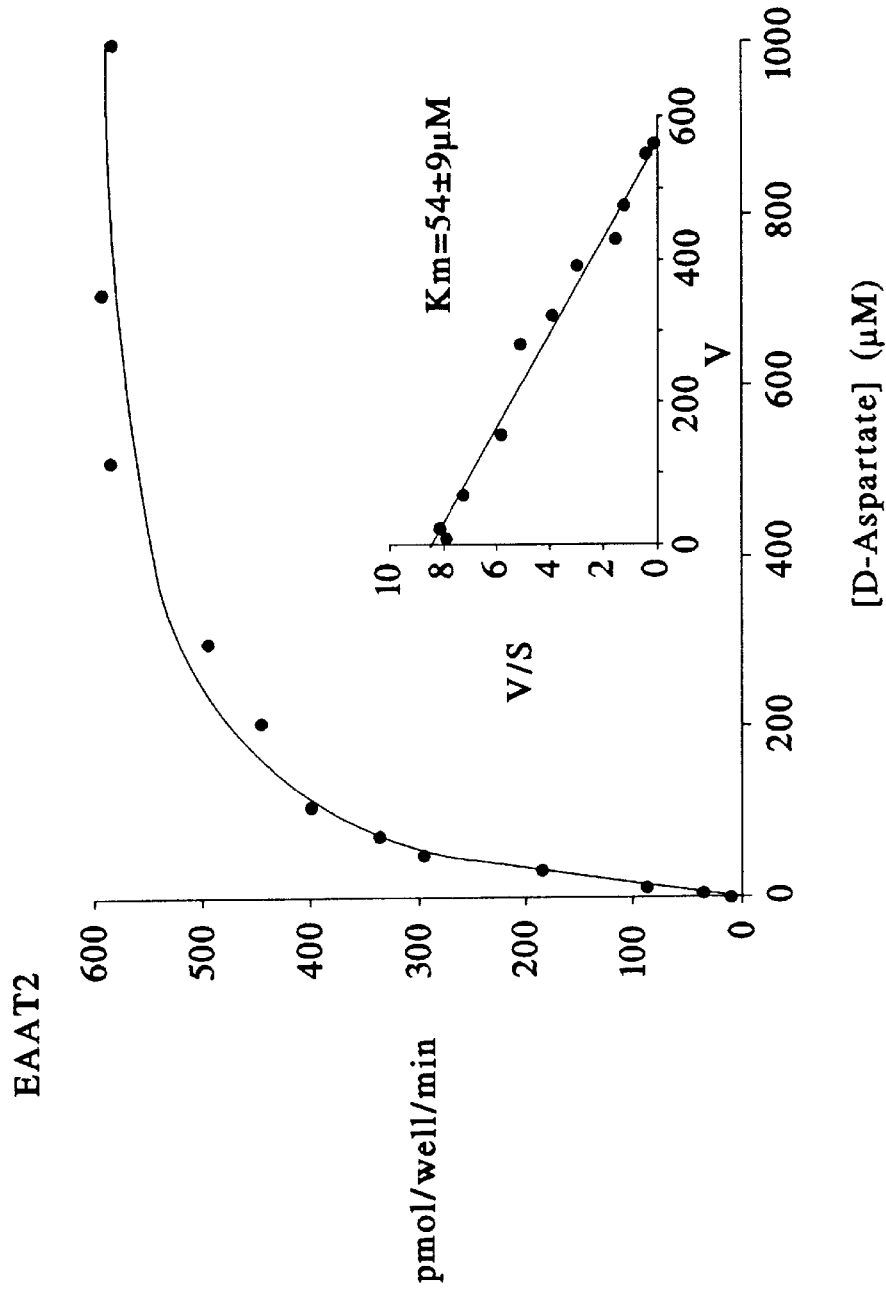
Figure 7E:
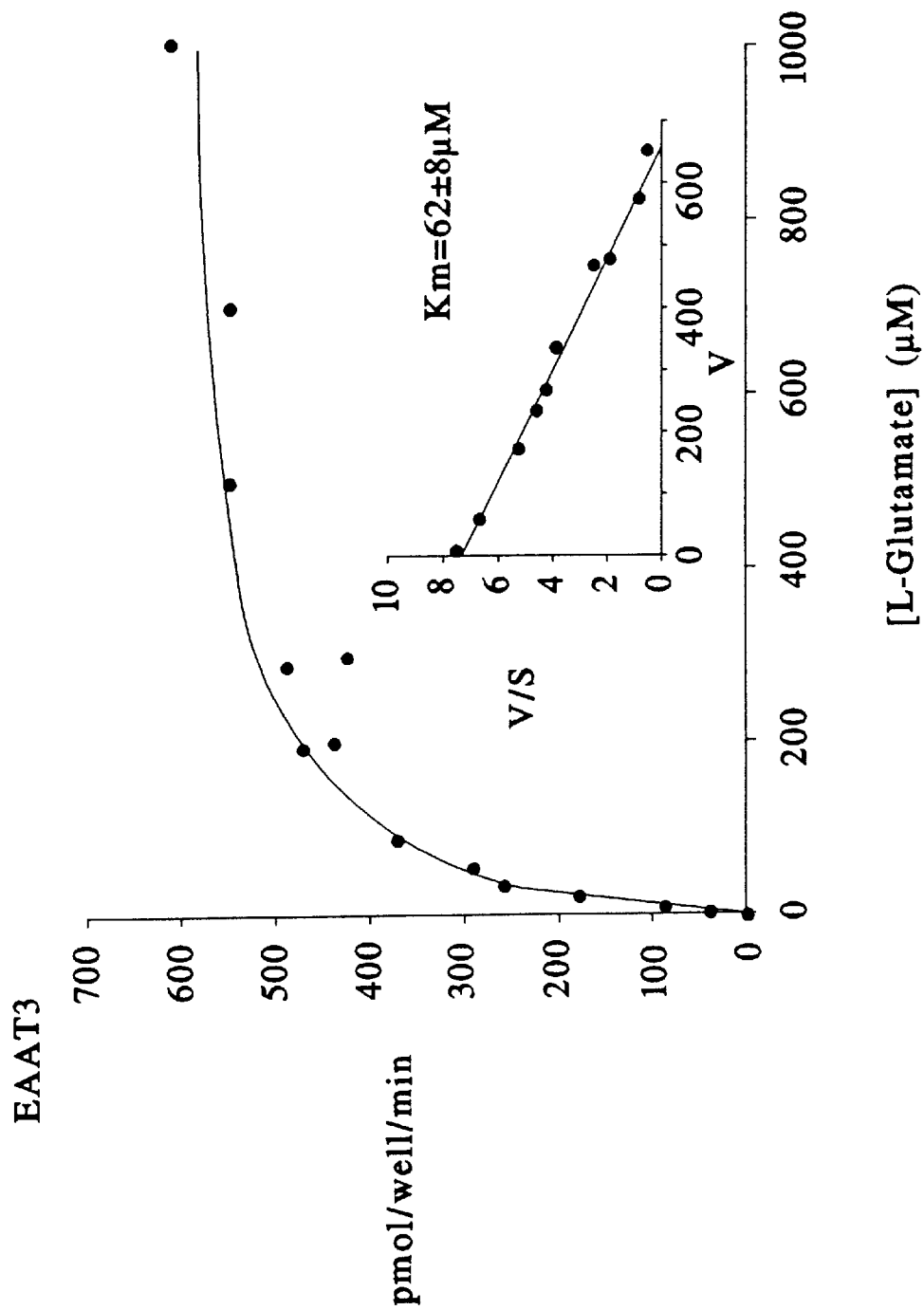
Figure 7F:
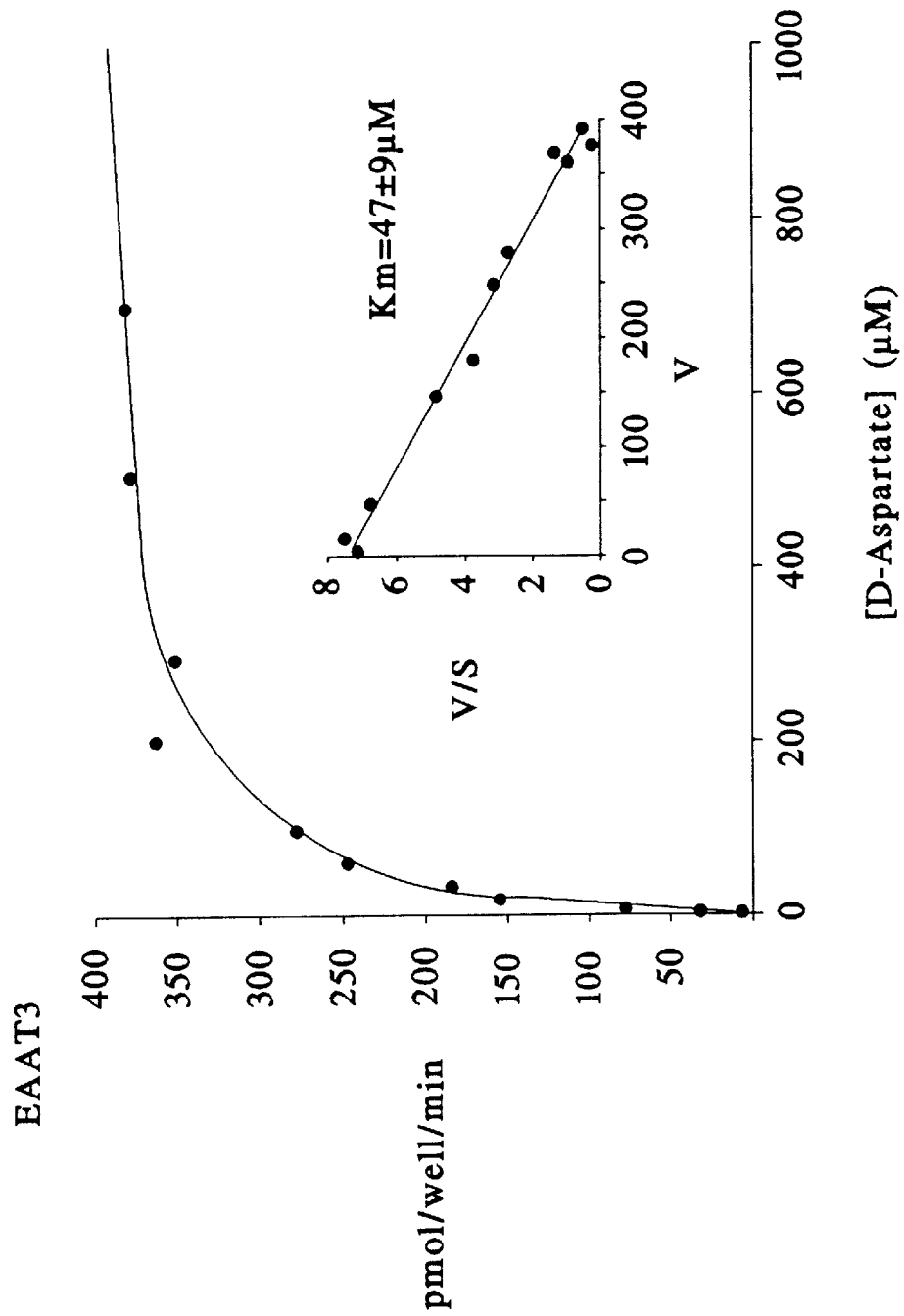

These results are shown in FIG. 7A through 7F. In the Figure, EAAT1 transporter kinetics of glutamate uptake are depicted in FIG. 7A and of aspartate are shown in FIG. 7B. Similarly, EAAT2 kinetics for glutamate and aspartate are shown in FIG. 7C and 7D, respectively. Finally, EAAT3 kinetics are shown in FIG. 7E (glutamate) and FIG. 7F (aspartate). Each data point was determined by incubating a COS cell culture transfected with the appropriate pCMV5-glutamate transporter clone with 100 mM of radiolabeled amino acid and increasing amounts of unlabeled amino acid. Results are plotted as uptake velocity (in pmol/cell culture/min) minus endogenous uptake versus total amino acid concentration, and each data point was performed in triplicate. The results show that both glutamate and aspartate uptake mediated by each of the three novel human glutamate transporters is saturable. Insets in each Panel depict Eadie-Hofstee plots of initial velocity data, from which $K_m$ values were determined. The $K_m$ values are shown as the mean±standard error based on at least three independent experiments. These results show that each of the three novel transporter proteins comprising the instant invention is functionally competent as an amino acid transporter when expressed in a culture of mammalian cells, and that each of the novel transporters encoded by the cDNA clones EAAT1, EAAT2 and EAAT3 displays a collection of biochemical properties consistent with their designation as human glutamate transporter proteins.

EXAMPLE 6

Inhibitor Potency Analyses Using COS-7 Cells Expressing Amino Acid Transporter Proteins COS-7 cell cultures transformed with pCMV5-human glutamate transporter constructs as described in Example 4 were used to characterize the pharmacological properties of each of these transporter proteins relative to a variety of known glutamate transporter inhibitors. These assays were performed essentially as described in Example 4, with the exception that varying amounts of each of a number of known inhibitor compounds were included in the incubations.

Figure 8A:
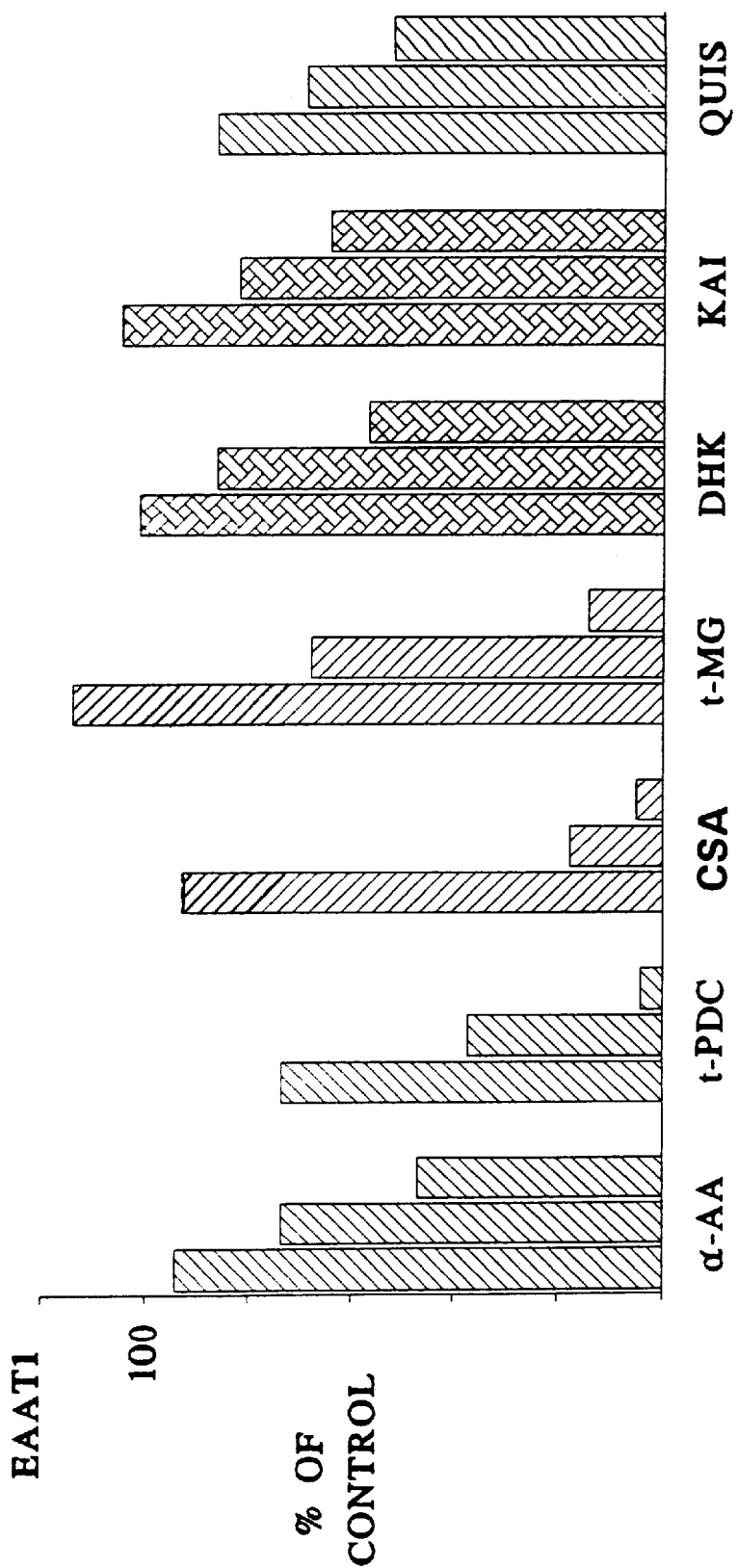
FIGS. 8A through 8C represents the pharmacological responsiveness of glutamate transport by the human excitatory amino acid transporters EAAT1, EAAT2 and EAAT3 when contacted with indicated competitors/inhibitors at 1 $\mu$M L-glutamate and inhibitor/competitor concentrations of 3 $\mu$M, 100 $\mu$M or 3 mM.
Figure 8B:
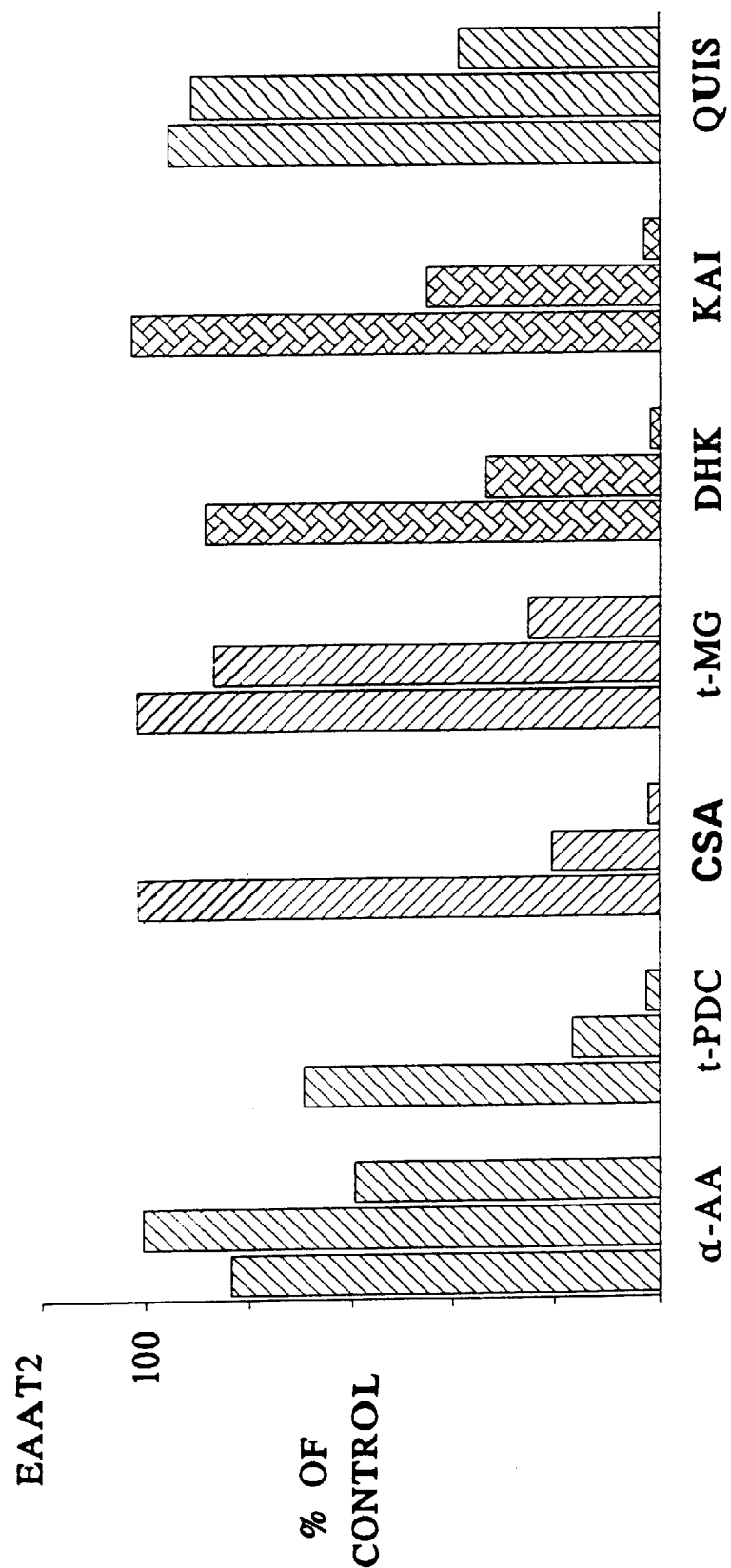
Figure 8C:
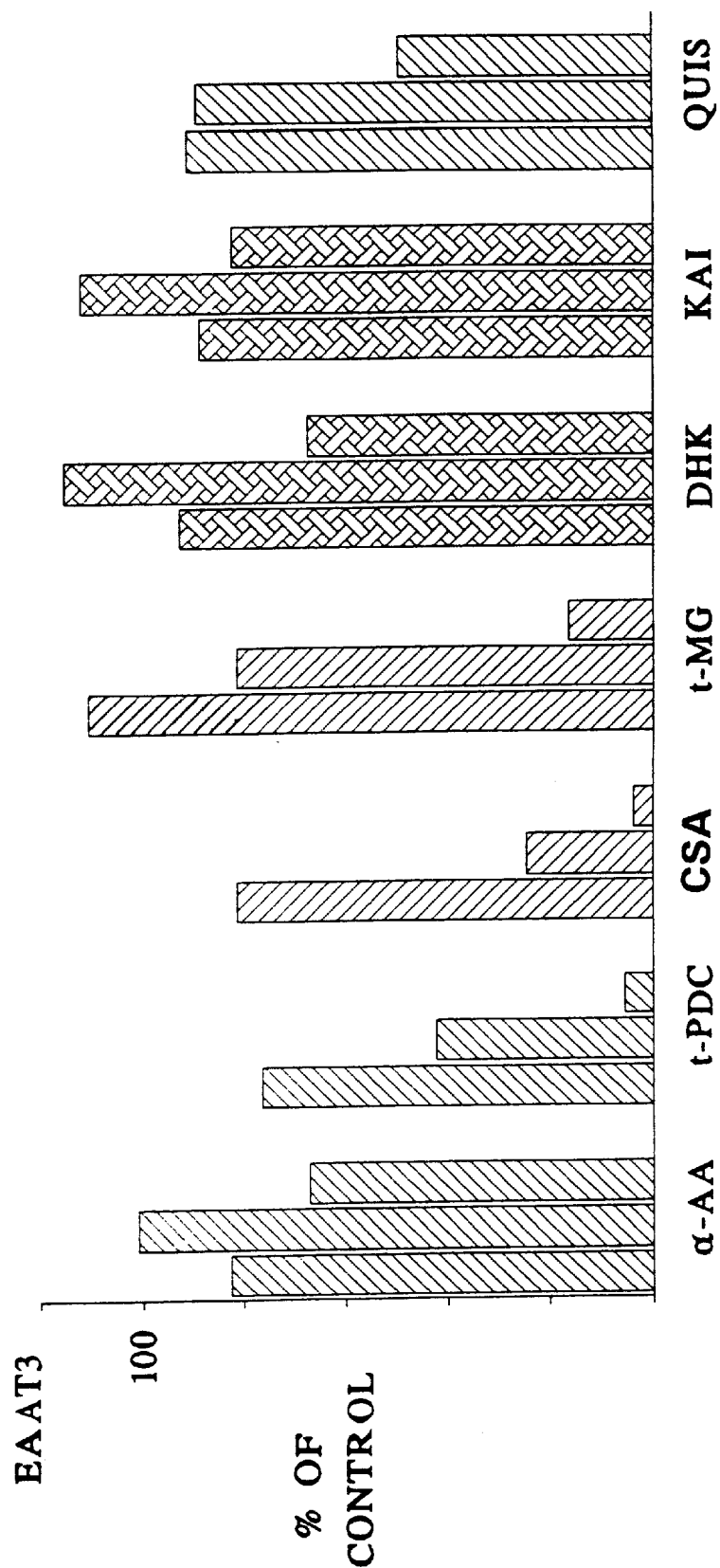

The results of these experiments are shown in FIGS. 8A through 8C. The data in FIG. 8A through 8C represent the pharmacological responsiveness of glutamate transport by the human excitatory amino acid transporters EAAT1, EAAT2 and EAAT3 when contacted with the following competitors/inhibitors: L-threo-β-hydroxyaspartate (THA); L-trans-pyrrolidine-2,4-dicarboxylate (PDC); L-serine-O-sulfate (SOS); dihydrokainate (DHK); and kainate (KAI). In these experiments, uptake of 1 µM of [$^3$H]-L-glutamate was determined in the presence of the indicated amounts of each of the inhibitors. As can be seen from the Figures, each of the glutamate transporter proteins of the invention displays a characteristic pattern of sensitivity to the inhibitors. Thus, the relative potency of inhibition of radiolabeled glutamate uptake was found to be as follows for the EAAT1 and EAAT3 transporter proteins:

THA<PDC<SOS<<DHK, KAI, whereas the inhibition pattern for EAAT2 was as follows:

PDC<THA<DHK<KAI<SOS.

These results, as well as results obtained from similar experiments performed with L-cysteate, L-cysteine sulfinic acid, β-glutamate and L-aspartate-β-hydroxymate, are shown in Table III. Even though the relative pattern of inhibition was the same for EAAT1 and EAAT3, the results shown in the Table support the finding that each of the glutamate transporters of the invention is uniquely characterized by its sensitivity to this panel of glutamate uptake inhibitors.

In addition, a number of reported inhibitors were found to be ineffective when tested with COS cell culture expressing each of the novel glutamate transporter proteins of the invention.

These include cis-1-aminocyclobutane-1,3-dicarboxylate, L-pyroglutamic acid, S-sulfo-L-cysteine, N-acetyl aspartylglutamate, N-methyl-Daspartate (NMDA) and quisqualate. α-aminoadipate, a classical inhibitor of glutamate uptake, exhibited only low potency when tested against all three EAAT subtypes. These results of functional assays support the conclusion arrived at from structural analysis (i.e., nucleic acid and amino acid sequence analyses) that the glutamate transporter cDNAs and proteins of the invention are novel mammalian transporter species.

EXAMPLE 7

Tissue Distribution of Amino Acid Transporter Expression

The tissue distribution of mRNA corresponding to expression of the amino acid transporters disclosed herein was determined in various tissues by Northern hybridization experiments (see Sambrook et al., ibid.). The results of these experiments are shown in FIGS. 9 and 10.

A panel of tissue samples was examined by Northern hybridization analysis performed under high stringency conditions as follows. A nylon filter containing 2 µg human peripheral tissue poly(A)$^+$ RNA was obtained from Cloneech Laboratories (Palo Alto, Calif.), and a similar filter was prepared containing human brain region RNA as follows. Total RNA was isolated from human brain region tissue obtained from the Oregon Brain Repository and 20 µg/region were size-fractionated by denaturing formaldehyde agarose gel electrophoresis (see Sambrook et al., ibid.). Fractionated RNA was then transferred to a nylon filter using the Northern blot/capillary-osmotic technique. Northern hybridization of both filters was performed individually with $^{32}$P-labeled amino acid transporter-specific probes for each transporter to be analyzed. Probes were derived from amino acid transporter coding sequences and labeled using $^{32}$P-labeled dCTP by the random primer method (Boehnger-Mannheim, Indianapolis Ind.). Filters were hybridized overnight at 42° C. individually with each radiolabeled probe (at a concentration of 10$^6$ cpm/mL) in a solution of 5X SSPE/ 50% formamide/7.5X Denhardt's solution (comprising 0.15 g/100 mL each of Ficoll, polyvinylpyrrolidone and bovine serum albumin)/2% SDS and 100 µg/mL denatured salmon-sperm DNA. Following hybridization, filters were washed twice for 30 min at room temperature in 2X SSPE/0.1% SDS and twice for 20 min at 20° C. in 0.1X SSPE/0.1% SDS. Hybridizing RNAs were visualized by autoradiography at −70° C. using intensifying screens. The filters were subsequently re-probed as described with a radiolabeled human β-actin probe (Clonetech) as a positive control.

Figure 9:
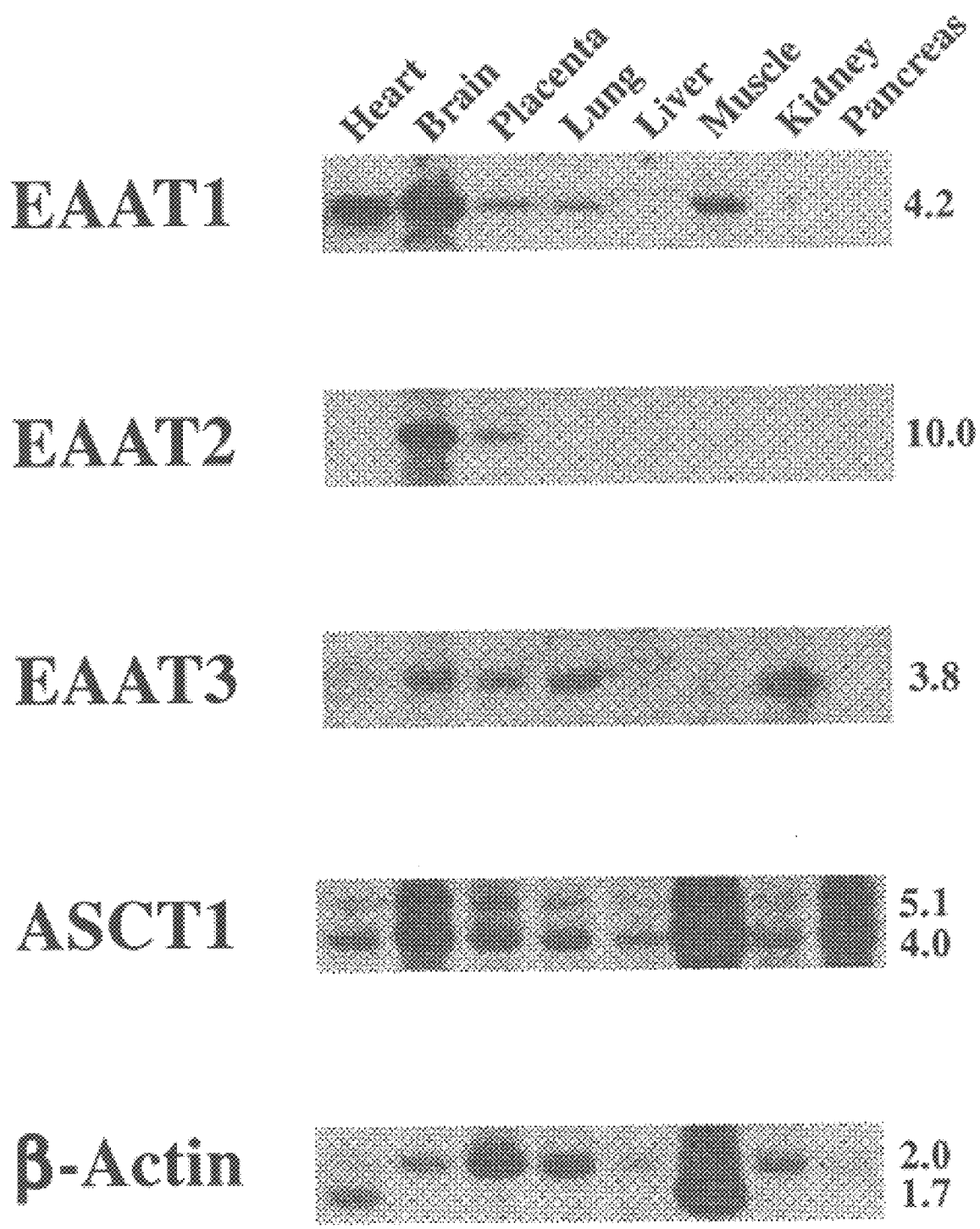
FIG. 9 shows the pattern of expression of EAAT1, EAAT2, EAAT3 and ASCT1 in human tissues; β-action is shown as a control for amount of RNA in each lane.
Figure 10:
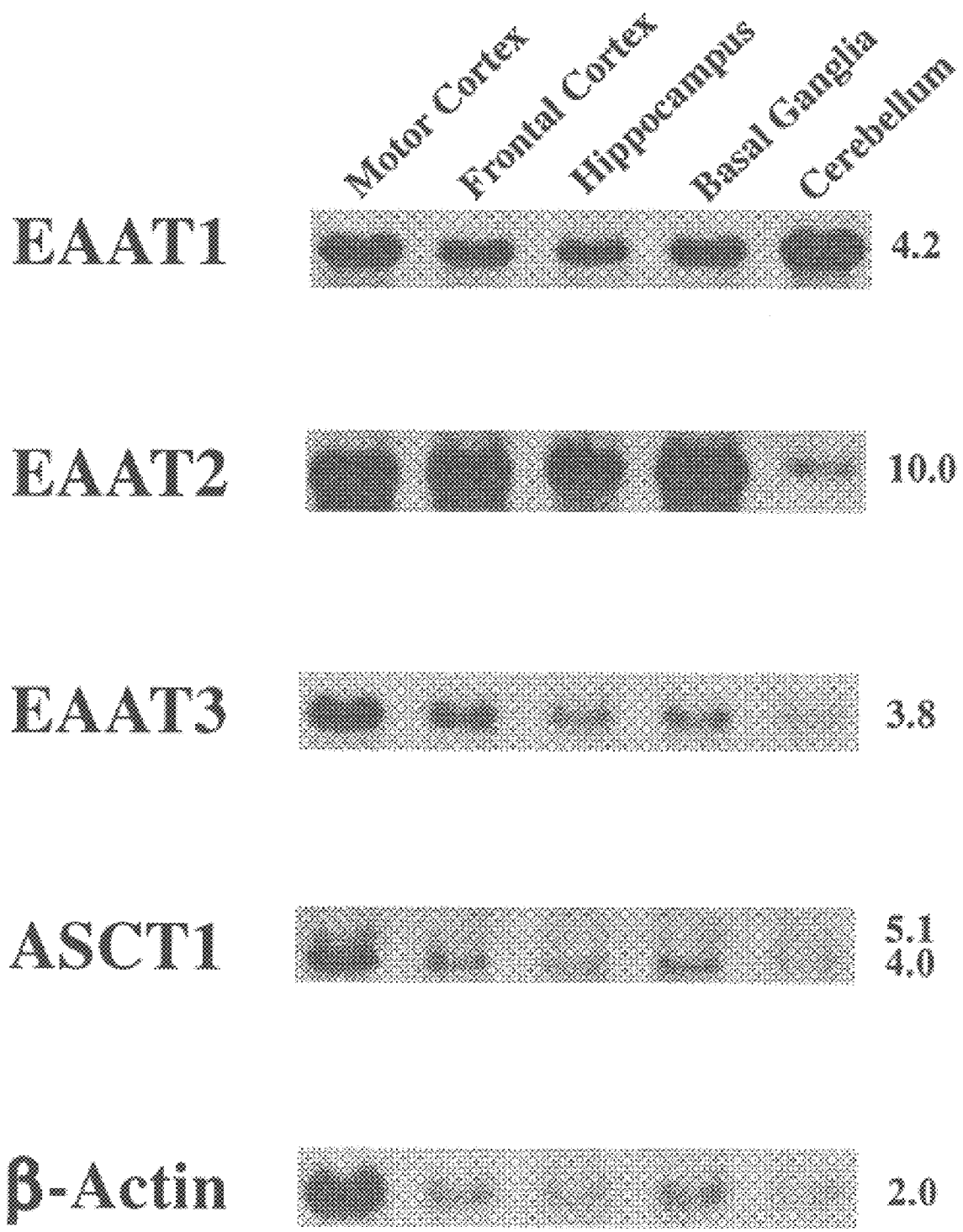
FIG. 10 shows the pattern of expression of EAAT1, EAAT2, EAAT3 and ASCT1 in human brain tissue; β-action is shown as a control for the amount of RNA in each lane.

The results of these experiments are shown in FIGS. 9 and 10. FIG. 9 illustrates expression of each of the amino acid transporters in human heart, brain, placenta, lung, liver, muscle, kidney and pancreas. The size (in kb) of the transcripts corresponding to expression of each transporter are displayed along the right-hand border of each panel. As is seen from these autoradiographs, EAAT1 is expressed predominantly in brain, heart and muscle, to a lesser extent in placenta and lung, weakly in liver, and at levels below the ability of this assay to detect in kidney and the pancreas (if at all). EAAT2 is expressed in brain, and to a lesser extent in placenta; expression was not detected in any other tissue tested. EAAT3 is expressed predominantly in the kidney, but significant expression was also detected in brain, placenta, and lung. ASCT1 is expressed in all tissues tested as at least one of three differently-sized transcripts, possibly corresponding to differential RNA processing during expression of this transporter (which result might be due in the alternative to the utilization of alternative polyadenylation sites found in the 3' untranslated region). These results demonstrate that the amino acid transporters disclosed herein are encoded by separate and distinct, albeit related, genes and that each transporter has a unique pattern of tissue-specific expression.

FIG. 10 shows the distribution of these amino acid transporter transcripts in different human brain regions. Varying expression levels were found for each of the amino acid transporters in all brain regions examined. These results support the conclusion that the amino acid transporters of the invention may play an important role in normal brain function, and that disruption of amino acid transport by these transporter may be important determinants in organic brain dysfunction, as a result of ischemia or anoxia.

EXAMPLE 8

Construction of Vaccinia Vinus-Recombinant Expression Constructs for Functional Expression of Amino Acid Transporters Using an alternative approach, the amino acid transporter proteins of the invention are expressed in human HeLa (vulval adenocarcinoma) cells via a vaccinia virus-based construct. In these experiments, each of the amino acid transporter cDNAs of the invention are excised from their respective pOTV-containing constructs and subcloned into a modified pBluescript (Strategene) vector wherein each of the amino acid transporter cDNAs described above is under the control of a bacteriophage T7 RNA polymerase promoter (as is described in Blakely et al., 1991, Anal. Biochem. 194: 302–308), termed pT7-AAT constructs. HeLa cells are first infected with a recombinant vaccinia virus, VTF-7, that expresses T7 RNA polymerase. Cells are incubated with virus at a concentration of about 10 plaque-forming unit/cell in serum-free Dulbecco's modified Eagle's medium at 37° C. for 30 min., and then the cells were transfected with each of the amino acid transporter constructs described above (i.e. the pT7-AAT constructs) using a lipofectin-mediated (Bethesda Research Labs, Gaithersburg, Md.) transfection protocol (see Felgner et al., 1987, Proc. Natl. Acad. Sci. USA 84: 7413–7417). Cells are then incubated for 12–24h before being assayed for amino acid transporter expression as described in Example 5.

EXAMPLE 9

Construction of Fusion Proteins-Recombinant Expression Constructs for Expression of Immunologically-Active Epitopes of Amino Acid Transporters The amino acid transporter proteins of the invention are expressed as fusion proteins in bacteria to produce immunologically-active epitopes. In these experiments, each of the amino acid transporter cDNAs of the invention are excised from their respective pOTV-containing constructs and subcloned into a pGEX-2T construct (Pharmacia, Piscataway, N.J.) whereby the coding sequences of the amino acid transporter cDNAs are translationally in-frame with sequences encoding glutathione-S-transferase (described in Arriza et al., 1992, J. Neurosci. 12: 4045–4055), termed PGST-AAT constructs. After introduction of the PGST-AAT constructs into bacterial cells (E. coli, strain D5α) using conventional techniques (see Sambrook et al., ibid.), fusion protein expression is induced with isopropyl-1-thio-β-D-galactopyranoside as described (Smith & Johnson, 1988, Gene 67: 31–40) and are purified using glutathione-Sepharose 4B (Pharmacia). Antibodies are then raised against each of the amino acid transporters of the invention by inoculation of rabbits with 300–500 µg of purified fusion protein in Freund's adjuvant (Grand Island Biological Co., Grand Island, N.Y.), said inoculation repeated approximately every 4 weeks. Sera are immunoaffinity-purified on columns of Affi-Gel 15 derivatized with purified fusion protein. After salt elution, such antibodies are neutralized, stabilized with bovine serum albumin at a final concentration of 1 mg/mL, dialyzed against PBS and assayed by immunoblotting using conventional techniques (Harlow & Lane, 1988, Antibodies: A Laboratory Manual, Cold Spring Harbor Laboratory Press, Cold Spring Harbor, N.Y.).

It should be understood that the foregoing disclosure emphasizes certain specific embodiments of the invention and that all modifications or alternatives equivalent thereto are within the spirit and scope of the invention as set forth in the appended claims.

TABLE I

| Amino Acid (1 mM)* | ASCT1 RNA-injected Oocytes** | Water-injected Oocytes** |
| --- | --- | --- |
| Alanine | 18 ± 2 | 0.6 ± 0.1 |
| Serine | 10 ± 5.1 | 0.4 ± 0.1 |
| Cysteine | 19.2 ± 5.9 | 1.0 ± 0.3 |

*n= 5
**pmol/min per oocyte:

TABLE II

| Amino Acid* | $K_m$ ($\mu$M) | $I_{max}$** |
| --- | --- | --- |
| Alanine | 71 ± 14 | (1.0) |
| Serine | 88 ± 11 | 1.2 ± 0.08 |
| Cysteine | 29 ± 6 | 1.0 ± 0.04 |
| Threonine | 137 ± 19 | 1.4 ± 0.03 |
| Valine | 390 ± 8 | 0.6 ± 0.11 |

NOTE: data is expressed as the mean of at least 5 determinations ± standard error.
*All amino acids were the L-stereoisomer
**$I_{max}$ was determined by least squares fit to the equation: $I = I_{max} \times ([S]/(K_m + [S]))$ where $I_{max}$ is the maximal current and $K_m$ is the transport constant

TABLE III

Glutamate uptake inhibition constants.

| | Ki (in $\mu$M) determined for each transporter[a] | | |
| --- | --- | --- | --- |
| Compound | EAAT1 | EAAT2 | EAAT3 |
| THA (L-threo-β-hydroxy-aspartate) | 32 ± 8 | 19 ± 6 | 25 ± 5 |
| PDC (L-trans-pyrrolidine-2,4-dicarboxylate) | 79 ± 7 | 8 ± 2 | 61 ± 14 |
| SOS (L-Serine-O-sulfate) | 107 ± 8 | 1157 ± 275 | 150 ± 52 |
| DHK (Dihydrokainate) | >1 mM | 23 ± 6 | >1 mM |
| KAI (Kainate) | >1 mM | 59 ± 18 | >1 mM |
| L-cysteate | 10 ± 3 | 10 ± 2 | 19 ± 9 |
| L-cysteine sulfinic acid | 14 ± 7 | 6 ± 1 | 17 ± 2 |
| β-glutamate | 297 ± 118 | 156 ± 37 | 307 ± 48 |
| L-aspartate-β-hydroxymate | 369 ± 70 | 184 ± 27 | 133 ± 34 |

[a]Under the assay conditions used ([S]<<Km), the Ki value does not differ significantly from the measured IC50.

What we claim is:

1. An isolated nucleic acid comprising a nucleotide sequence encoding a human excitatory amino acid transporter, wherein the nucleotide sequence of the nucleic acid comprises the sequence of the excitatory amino acid transporter EAAT1 (SEQ ID No.4).

2. A nucleic acid hybridization probe for the detection of mammalian excitatory amino acid transporter-encoding nucleic acid comprising the nucleotide sequence of claim 1.

3. A recombinant expression construct comprising a nucleic acid having a nucleotide sequence encoding a mammalian excitatory amino acid transporter, wherein the nucleotide sequence of the nucleic acid comprises the sequence of the human EAAT1 excitatory amino acid transporter (SEQ ID No.4), and wherein the construct expresses the EAAT1 excitatory amino acid transporter in a transformed culture of eukaryotic or prokaryotic cells.

4. A cell culture transformed with the recombinant expression construct of claim 3.

* * * * *

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
       (A) LENGTH: 63 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:1:

CTGRGCRATG AARATGGCAG CCAGGGCYTC ATACAGGGCT GTGCCRTCCA TGTTRATGGT    60

RGC    63

(2) INFORMATION FOR SEQ ID NO:2:

(i) SEQUENCE CHARACTERISTICS:
       (A) LENGTH: 1680 base pairs
       (B) TYPE: nucleic acid
       (C) STRANDEDNESS: single
       (D) TOPOLOGY: linear (ii) MOLECULE TYPE: cDNA (ix) FEATURE:
       (A) NAME/KEY: 5'UTR
       (B) LOCATION: 1..30

(ix) FEATURE:
       (A) NAME/KEY: CDS
       (B) LOCATION: 31..1626

(ix) FEATURE:
       (A) NAME/KEY: 3'UTR
       (B) LOCATION: 1626..1680

(xi) SEQUENCE DESCRIPTION: SEQ ID NO:2:

CACCTCTAGC TCGGAGCGGC GTGTAGCGCC ATG GAG AAG AGC AAC GAG ACC AAC    54
                                Met Glu Lys Ser Asn Glu Thr Asn
                                  1               5

GGC TAC CTT GAC AGC GCT CAG GCG GGG CCT GCG GCC GGG CCC GGA GCT    102
Gly Tyr Leu Asp Ser Ala Gln Ala Gly Pro Ala Ala Gly Pro Gly Ala
    10                  15                  20

CCG GGG ACC GCG GCG GGA CGC GCA CGG CGT TGC GCG CGC TTC CTG CGG    150
Pro Gly Thr Ala Ala Gly Arg Ala Arg Arg Cys Ala Arg Phe Leu Arg
25                  30                  35                  40

CGC CAA GCG CTG GTG CTG CTC ACC GTG TCC GGG GTG CTG GCG GGC GCG    198
Arg Gln Ala Leu Val Leu Leu Thr Val Ser Gly Val Leu Ala Gly Ala
                45                  50                  55

GGC CTG GGC GCG GCG TTG CGC GGG CTC AGC CTG AGC CGC ACG CAG GTC    246
Gly Leu Gly Ala Ala Leu Arg Gly Leu Ser Leu Ser Arg Thr Gln Val
            60                  65                  70

ACC TAC CTG GCC TTC CCC GGC GAG ATG CTG CTC CGC ATG CTG CGC ATG    294
Thr Tyr Leu Ala Phe Pro Gly Glu Met Leu Leu Arg Met Leu Arg Met
        75                  80                  85

ATC ATC CTG CCG CTG GTG GTC TGC AGC CTG GTG TCG GGC GCC GCC TCG    342
Ile Ile Leu Pro Leu Val Val Cys Ser Leu Val Ser Gly Ala Ala Ser
    90                  95                  100

CTC GAT GCC AGC TGC CTC GGG CGT CTG GGC GGC ATC CGT GTC GCC TAC    390
Leu Asp Ala Ser Cys Leu Gly Arg Leu Gly Gly Ile Arg Val Ala Tyr
105                 110                 115                 120

```
TTT GGC CTC ACC ACA CTG AGT GCC TCG GCG CTC GCC GTG GCC TTG GCG      438
Phe Gly Leu Thr Thr Leu Ser Ala Ser Ala Leu Ala Val Ala Leu Ala
                125                 130                 135

TTC ATC ATC AAG CCA GGA TCC GGT GCG CAG ACC CTT CAG TCC AGC GAC      486
Phe Ile Ile Lys Pro Gly Ser Gly Ala Gln Thr Leu Gln Ser Ser Asp
            140                 145                 150

CTG GGG CTG GAG GAC TCG GGG CCT CCT CCT GTC CCC AAA GAG ACG GTG      534
Leu Gly Leu Glu Asp Ser Gly Pro Pro Pro Val Pro Lys Glu Thr Val
                155                 160                 165

GAC TCT TTC CTC GAC CTG GCC AGA AAC CTG TTT CCC TCC AAT CTT GTG      582
Asp Ser Phe Leu Asp Leu Ala Arg Asn Leu Phe Pro Ser Asn Leu Val
        170                 175                 180

GTT GCA GCT TTC CGT ACG TAT GCA ACC GAT TAT AAA GTC GTG ACC CAG      630
Val Ala Ala Phe Arg Thr Tyr Ala Thr Asp Tyr Lys Val Val Thr Gln
185                 190                 195                 200

AAC AGC AGC TCT GGA AAT GTA ACC CAT GAA AAG ATC CCC ATA GGC ACT      678
Asn Ser Ser Ser Gly Asn Val Thr His Glu Lys Ile Pro Ile Gly Thr
                205                 210                 215

GAG ATA GAA GGG ATG AAC ATT TTA GGA TTG GTC CTG TTT GCT CTG GTG      726
Glu Ile Glu Gly Met Asn Ile Leu Gly Leu Val Leu Phe Ala Leu Val
            220                 225                 230

TTA GGA GTG GCC TTA AAG AAA CTA GGC TCC GAA GGA GAA GAC CTC ATC      774
Leu Gly Val Ala Leu Lys Lys Leu Gly Ser Glu Gly Glu Asp Leu Ile
                235                 240                 245

CGT TTC TTC AAT TCC CTC AAC GAG GCG ACG ATG GTG CTG GTG TCC TGG      822
Arg Phe Phe Asn Ser Leu Asn Glu Ala Thr Met Val Leu Val Ser Trp
        250                 255                 260

ATT ATG TGG TAC GTA CCT GTG GGC ATC ATG TTC CTT GTT GGA AGC AAG      870
Ile Met Trp Tyr Val Pro Val Gly Ile Met Phe Leu Val Gly Ser Lys
265                 270                 275                 280

ATC GTG GAA ATG AAA GAC ATC ATC GTG CTG GTG ACC AGC CTG GGG AAA      918
Ile Val Glu Met Lys Asp Ile Ile Val Leu Val Thr Ser Leu Gly Lys
                285                 290                 295

TAC ATC TTC GCA TCT ATA TTG GGC CAT GTT ATT CAT GGA GGA ATT GTT      966
Tyr Ile Phe Ala Ser Ile Leu Gly His Val Ile His Gly Gly Ile Val
            300                 305                 310

CTG CCA CTT ATT TAT TTT GTT TTC ACA CGA AAA AAC CCA TTC AGA TTC     1014
Leu Pro Leu Ile Tyr Phe Val Phe Thr Arg Lys Asn Pro Phe Arg Phe
                315                 320                 325

CTC CTG GGC CTC CTC GCC CCA TTT GCG ACA GCA TTT GCT ACC TGC TCC     1062
Leu Leu Gly Leu Leu Ala Pro Phe Ala Thr Ala Phe Ala Thr Cys Ser
        330                 335                 340

AGC TCA GCG ACC CTT CCC TCT ATG ATG AAG TGC ATT GAA GAG AAC AAT     1110
Ser Ser Ala Thr Leu Pro Ser Met Met Lys Cys Ile Glu Glu Asn Asn
345                 350                 355                 360

GGT GTG GAC AAG AGG ATC AGC AGG TTT ATT CTC CCC ATC GGG GCC ACC     1158
Gly Val Asp Lys Arg Ile Ser Arg Phe Ile Leu Pro Ile Gly Ala Thr
                365                 370                 375

GTG AAC ATG GAC GGA GCA GCC ATC TTC CAG TGT GTG GCC GCG GTG TTC     1206
Val Asn Met Asp Gly Ala Ala Ile Phe Gln Cys Val Ala Ala Val Phe
            380                 385                 390

ATT GCG CAA CTC AAC AAC ATA GAG CTC AAC GCA GGA CAG ATT TTC ACC     1254
Ile Ala Gln Leu Asn Asn Ile Glu Leu Asn Ala Gly Gln Ile Phe Thr
                395                 400                 405

ATT CTA GTG ACT GCC ACA GCG TCC AGT GTT GGA GCA GCA GGC GTG CCA     1302
Ile Leu Val Thr Ala Thr Ala Ser Ser Val Gly Ala Ala Gly Val Pro
        410                 415                 420

GCT GGA GGG GTC CTC ACC ATT GCC ATT ATC CTG GAG GCC ATT GGG CTG     1350
Ala Gly Gly Val Leu Thr Ile Ala Ile Ile Leu Glu Ala Ile Gly Leu
425                 430                 435                 440
```

```
CCT ACT CAT GAC CTG CCT CTG ATC CTG GCT GTG GAC TGG ATT GTG GAC    1398
Pro Thr His Asp Leu Pro Leu Ile Leu Ala Val Asp Trp Ile Val Asp
            445                 450                 455

CGG ACC ACC ACG GTG GTG AAT GTG GAG GGG GAT GCC CTG GGT GCA GGC    1446
Arg Thr Thr Thr Val Val Asn Val Glu Gly Asp Ala Leu Gly Ala Gly
            460                 465                 470

ATT CTC CAC CAC CTG AAT CAG AAG GCA ACA AAG AAA GGC GAG CAG GAA    1494
Ile Leu His His Leu Asn Gln Lys Ala Thr Lys Lys Gly Glu Gln Glu
            475                 480                 485

CTT GCT GAG GTG AAA GTG GAA GCC ATC CCC AAC TGC AAG TCT GAG GAG    1542
Leu Ala Glu Val Lys Val Glu Ala Ile Pro Asn Cys Lys Ser Glu Glu
            490                 495                 500

GAG ACA TCG CCC CTG GTG ACA CAC CAG AAC CCC GCT GGC CCC GTG GCC    1590
Glu Thr Ser Pro Leu Val Thr His Gln Asn Pro Ala Gly Pro Val Ala
505                 510                 515                 520

AGT GCC CCA GAA CTG GAA TCC AAG GAG TCG GTT CTG TGATGGGGCT         1636
Ser Ala Pro Glu Leu Glu Ser Lys Glu Ser Val Leu
            525                 530

GGGCTTTGGG CTTGCCTGCC AGCAGTGATG TCCCACCCTG TTCA                   1680

(2) INFORMATION FOR SEQ ID NO:3:

(i) SEQUENCE CHARACTERISTICS:
        (A) LENGTH: 532 amino acids
        (B) TYPE: amino acid
        (D) TOPOLOGY: linear (ii) MOLECULE TYPE: protein (xi) SEQUENCE DESCRIPTION: SEQ ID NO:3:

Met Glu Lys Ser Asn Glu Thr Asn Gly Tyr Leu Asp Ser Ala Gln Ala
 1               5                  10                  15

Gly Pro Ala Ala Gly Pro Gly Ala Pro Gly Thr Ala Ala Gly Arg Ala
                20                  25                  30

Arg Arg Cys Ala Arg Phe Leu Arg Arg Gln Ala Leu Val Leu Leu Thr
            35                  40                  45

Val Ser Gly Val Leu Ala Gly Ala Gly Leu Gly Ala Ala Leu Arg Gly
        50                  55                  60

Leu Ser Leu Ser Arg Thr Gln Val Thr Tyr Leu Ala Phe Pro Gly Glu
65                  70                  75                  80

Met Leu Leu Arg Met Leu Arg Met Ile Ile Leu Pro Leu Val Val Cys
                85                  90                  95

Ser Leu Val Ser Gly Ala Ala Ser Leu Asp Ala Ser Cys Leu Gly Arg
                100                 105                 110

Leu Gly Gly Ile Arg Val Ala Tyr Phe Gly Leu Thr Thr Leu Ser Ala
            115                 120                 125

Ser Ala Leu Ala Val Ala Leu Ala Phe Ile Ile Lys Pro Gly Ser Gly
        130                 135                 140

Ala Gln Thr Leu Gln Ser Ser Asp Leu Gly Leu Glu Asp Ser Gly Pro
145                 150                 155                 160

Pro Pro Val Pro Lys Glu Thr Val Asp Ser Phe Leu Asp Leu Ala Arg
                165                 170                 175

Asn Leu Phe Pro Ser Asn Leu Val Val Ala Ala Phe Arg Thr Tyr Ala
                180                 185                 190

Thr Asp Tyr Lys Val Val Thr Gln Asn Ser Ser Ser Gly Asn Val Thr
            195                 200                 205

His Glu Lys Ile Pro Ile Gly Thr Glu Ile Glu Gly Met Asn Ile Leu
        210                 215                 220
```

Gly Leu Val Leu Phe Ala Leu Val Leu Gly Val Ala Leu Lys Lys Leu
225                 230                 235                 240

Gly Ser Glu Gly Glu Asp Leu Ile Arg Phe Phe Asn Ser Leu Asn Glu
            245                 250                 255

Ala Thr Met Val Leu Val Ser Trp Ile Met Trp Tyr Val Pro Val Gly
            260                 265                 270

Ile Met Phe Leu Val Gly Ser Lys Ile Val Glu Met Lys Asp Ile Ile
            275                 280                 285

Val Leu Val Thr Ser Leu Gly Lys Tyr Ile Phe Ala Ser Ile Leu Gly
            290                 295                 300

His Val Ile His Gly Gly Ile Val Leu Pro Leu Ile Tyr Phe Val Phe
305                 310                 315                 320

Thr Arg Lys Asn Pro Phe Arg Phe Leu Leu Gly Leu Leu Ala Pro Phe
            325                 330                 335

Ala Thr Ala Phe Ala Thr Cys Ser Ser Ser Ala Thr Leu Pro Ser Met
            340                 345                 350

Met Lys Cys Ile Glu Glu Asn Asn Gly Val Asp Lys Arg Ile Ser Arg
            355                 360                 365

Phe Ile Leu Pro Ile Gly Ala Thr Val Asn Met Asp Gly Ala Ala Ile
370                 375                 380

Phe Gln Cys Val Ala Ala Val Phe Ile Ala Gln Leu Asn Asn Ile Glu
385                 390                 395                 400

Leu Asn Ala Gly Gln Ile Phe Thr Ile Leu Val Thr Ala Thr Ala Ser
            405                 410                 415

Ser Val Gly Ala Ala Gly Val Pro Ala Gly Gly Val Leu Thr Ile Ala
            420                 425                 430

Ile Ile Leu Glu Ala Ile Gly Leu Pro Thr His Asp Leu Pro Leu Ile
            435                 440                 445

Leu Ala Val Asp Trp Ile Val Asp Arg Thr Thr Thr Val Val Asn Val
            450                 455                 460

Glu Gly Asp Ala Leu Gly Ala Gly Ile Leu His His Leu Asn Gln Lys
465                 470                 475                 480

Ala Thr Lys Lys Gly Glu Gln Glu Leu Ala Glu Val Lys Val Glu Ala
            485                 490                 495

Ile Pro Asn Cys Lys Ser Glu Glu Thr Ser Pro Leu Val Thr His
            500                 505                 510

Gln Asn Pro Ala Gly Pro Val Ser Ala Pro Glu Leu Glu Ser Lys
            515                 520                 525

Glu Ser Val Leu
530

(2) INFORMATION FOR SEQ ID NO:4:

(i) SEQUENCE CHARACTERISTICS:
        (A) LENGTH: 1680 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: 5'UTR
        (B) LOCATION: 1..30

(ix) FEATURE:
        (A) NAME/KEY: CDS
        (B) LOCATION: 31..1656

(ix) FEATURE:
    (A) NAME/KEY: 3'UTR
    (B) LOCATION: 1657..1680

(xi) SEQUENCE DESCRIPTION: SEQ ID NO:4:

```
AAAGAAGAGA CCCTCCTAGA AAAGTAAAAT ATG ACT AAA AGC AAT GGA GAA GAG      54
                                 Met Thr Lys Ser Asn Gly Glu Glu
                                  1               5

CCC AAG ATG GGG GGC AGG ATG GAG AGA TTC CAG CAG GGA GTC CGT AAA     102
Pro Lys Met Gly Gly Arg Met Glu Arg Phe Gln Gln Gly Val Arg Lys
     10              15                  20

CGC ACA CTT TTG GCC AAG AAG AAA GTG CAG AAC ATT ACA AAG GAG GTT     150
Arg Thr Leu Leu Ala Lys Lys Lys Val Gln Asn Ile Thr Lys Glu Val
 25              30                  35                      40

GTT AAA AGT TAC CTG TTT CGG AAT GCT TTT GTG CTG CTC ACA GTC ACC     198
Val Lys Ser Tyr Leu Phe Arg Asn Ala Phe Val Leu Leu Thr Val Thr
             45                  50                  55

GCT GTC ATT GTG GGT ACA ATC CTT GGA TTT ACC CTC CGA CCA TAC AGA     246
Ala Val Ile Val Gly Thr Ile Leu Gly Phe Thr Leu Arg Pro Tyr Arg
                 60                  65                  70

ATG AGC TAC CGG GAA GTC AAG TAC TTC TCC TTT CCT GGG GAA CTT CTG     294
Met Ser Tyr Arg Glu Val Lys Tyr Phe Ser Phe Pro Gly Glu Leu Leu
             75                  80                  85

ATG AGG ATG TTA CAG ATG CTG GTC TTA CCA CTT ATC ATC TCC AGT CTT     342
Met Arg Met Leu Gln Met Leu Val Leu Pro Leu Ile Ile Ser Ser Leu
 90                  95                 100

GTC ACA GGA ATG GCG GCG CTA GAT AGT AAG GCA TCA GGG AAG TGG GAA     390
Val Thr Gly Met Ala Ala Leu Asp Ser Lys Ala Ser Gly Lys Trp Glu
105             110                 115                 120

TGC GGA GCT GTA GTC TAT TAT ATG ACT ACC ACC ATC ATT GCT GTG GTG     438
Cys Gly Ala Val Val Tyr Tyr Met Thr Thr Thr Ile Ile Ala Val Val
                125                 130                 135

ATT GGC ATA ATC ATT GTC ATC ATC ATC CAT CCT GGG AAG GGC ACA AAG     486
Ile Gly Ile Ile Ile Val Ile Ile Ile His Pro Gly Lys Gly Thr Lys
                140                 145                 150

GAA AAC ATG CAC AGA GAA GGC AAA ATT GTA CGA GTG ACA GCT GCA GAT     534
Glu Asn Met His Arg Glu Gly Lys Ile Val Arg Val Thr Ala Ala Asp
            155                 160                 165

GCC TTC CTG GAC TTG ATC AGG AAC ATG TTA AAT CCA AAT CTG GTA GAA     582
Ala Phe Leu Asp Leu Ile Arg Asn Met Leu Asn Pro Asn Leu Val Glu
170                 175                 180

GCC TGC TTT AAA CAG TTT AAA ACC AAC TAT GAG AAG AGA AGC TTT AAA     630
Ala Cys Phe Lys Gln Phe Lys Thr Asn Tyr Glu Lys Arg Ser Phe Lys
185                 190                 195                 200

GTG CCC ATC CAG GCC AAC GAA ACG CTT GTG GGT GCT GTG ATA AAC AAT     678
Val Pro Ile Gln Ala Asn Glu Thr Leu Val Gly Ala Val Ile Asn Asn
                205                 210                 215

GTG TCT GAG GCC ATG GAG ACT CTT ACC CGA ATC ACA GAG GAG CTG GTC     726
Val Ser Glu Ala Met Glu Thr Leu Thr Arg Ile Thr Glu Glu Leu Val
                220                 225                 230

CCA GTT CCA GGA TCT GTG AAT GGA GTC AAT GCC CTG GGT CTA GTT GTC     774
Pro Val Pro Gly Ser Val Asn Gly Val Asn Ala Leu Gly Leu Val Val
                235                 240                 245

TTC TCC ATG TGC TTC GGT TTT GTG ATT GGA AAC ATG AAG GAA CAG GGG     822
Phe Ser Met Cys Phe Gly Phe Val Ile Gly Asn Met Lys Glu Gln Gly
250                 255                 260

CAG GCC CTG AGA GAG TTC TTT GAT TCT CTT AAC GAA GCC ATC ATG AGA     870
Gln Ala Leu Arg Glu Phe Phe Asp Ser Leu Asn Glu Ala Ile Met Arg
265                 270                 275                 280

CTG GTA GCA GTA ATA ATG TGG TAT GCC CCC GTG GGT ATT CTC TTC CTG     918
Leu Val Ala Val Ile Met Trp Tyr Ala Pro Val Gly Ile Leu Phe Leu
```

-continued

```
                    285                 290                 295
ATT GCT GGG AAG ATT GTG GAG ATG GAA GAC ATG GGT GTG ATT GGG GGG     966
Ile Ala Gly Lys Ile Val Glu Met Glu Asp Met Gly Val Ile Gly Gly
            300                 305                 310

CAG CTT GCC ATG TAC ACC GTG ACT GTC ATT GTT GGC TTA CTC ATT CAC    1014
Gln Leu Ala Met Tyr Thr Val Thr Val Ile Val Gly Leu Leu Ile His
            315                 320             325

GCA GTC ATC GTC TTG CCA CTC CTC TAC TTC TTG GTA ACA CGG AAA AAC    1062
Ala Val Ile Val Leu Pro Leu Leu Tyr Phe Leu Val Thr Arg Lys Asn
            330             335                 340

CCT TGG GTT TTT ATT GGA GGG TTG CTG CAA GCA CTC ATC ACC GCT CTG    1110
Pro Trp Val Phe Ile Gly Gly Leu Leu Gln Ala Leu Ile Thr Ala Leu
345             350                 355                 360

GGG ACC TCT TCA AGT TCT GCC ACC CTA CCC ATC ACC TTC AAG TGC CTG    1158
Gly Thr Ser Ser Ser Ser Ala Thr Leu Pro Ile Thr Phe Lys Cys Leu
                365                 370                 375

GAA GAG AAC AAT GGC GTG GAC AAG CGC GTC ACC AGA TTC GTG CTC CCC    1206
Glu Glu Asn Asn Gly Val Asp Lys Arg Val Thr Arg Phe Val Leu Pro
            380                 385                 390

GTA GGA GCC ACC ATT AAC ATG GAT GGG ACT GCC CTC TAT GAG GCT TTG    1254
Val Gly Ala Thr Ile Asn Met Asp Gly Thr Ala Leu Tyr Glu Ala Leu
            395                 400                 405

GCT GCC ATT TTC ATT GCT CAA GTT AAC AAC TTT GAA CTG AAC TTC GGA    1302
Ala Ala Ile Phe Ile Ala Gln Val Asn Asn Phe Glu Leu Asn Phe Gly
            410                 415                 420

CAA ATT ATT ACA ATC AGC ATC ACA GCC ACA GCT GCC AGT ATT GGG GCA    1350
Gln Ile Ile Thr Ile Ser Ile Thr Ala Thr Ala Ala Ser Ile Gly Ala
425             430                 435                 440

GCT GGA ATT CCT CAG GCG GGC CTG GTC ACT ATG GTC ATT GTG CTG ACA    1398
Ala Gly Ile Pro Gln Ala Gly Leu Val Thr Met Val Ile Val Leu Thr
                445                 450                 455

TCT GTC GGC CTG CCC ACT GAC GAC ATC ACG CTC ATC ATC GCG GTG GAC    1446
Ser Val Gly Leu Pro Thr Asp Asp Ile Thr Leu Ile Ile Ala Val Asp
                460                 465                 470

TGG TTC TTG GAT CGC CTC CGG ACC ACC ACC AAC GTA CTG GGA GAC TCC    1494
Trp Phe Leu Asp Arg Leu Arg Thr Thr Thr Asn Val Leu Gly Asp Ser
            475                 480                 485

CTG GGA GCT GGG ATT GTG GAG CAC TTG TCA CGA CAT GAA CTG AAG AAC    1542
Leu Gly Ala Gly Ile Val Glu His Leu Ser Arg His Glu Leu Lys Asn
            490                 495             500

AGA GAT GTT GAA ATG GGT AAC TCA GTG ATT GAA GAG AAT GAA ATG AAG    1590
Arg Asp Val Glu Met Gly Asn Ser Val Ile Glu Glu Asn Glu Met Lys
505             510                 515                 520

AAA CCA TAT CAA CTG ATT GCA CAG GAC AAT GAA ACT GAG AAA CCC ATC    1638
Lys Pro Tyr Gln Leu Ile Ala Gln Asp Asn Glu Thr Glu Lys Pro Ile
                525                 530                 535

GAC AGT GAA ACC AAG ATG TAGACTAACA TAAAGAAACA CTTT                 1680
Asp Ser Glu Thr Lys Met
                540
```

(2) INFORMATION FOR SEQ ID NO:5:

(i) SEQUENCE CHARACTERISTICS:
        (A) LENGTH: 542 amino acids
        (B) TYPE: amino acid
        (D) TOPOLOGY: linear (ii) MOLECULE TYPE: protein (xi) SEQUENCE DESCRIPTION: SEQ ID NO:5:

```
Met Thr Lys Ser Asn Gly Glu Glu Pro Lys Met Gly Gly Arg Met Glu
1               5                   10                  15
```

```
Arg Phe Gln Gln Gly Val Arg Lys Arg Thr Leu Leu Ala Lys Lys
            20                  25                  30
Val Gln Asn Ile Thr Lys Glu Val Lys Ser Tyr Leu Phe Arg Asn
        35                  40                  45
Ala Phe Val Leu Thr Val Thr Ala Val Ile Val Gly Thr Ile Leu
    50                  55                  60
Gly Phe Thr Leu Arg Pro Tyr Arg Met Ser Tyr Arg Glu Val Lys Tyr
65                  70                  75                  80
Phe Ser Phe Pro Gly Glu Leu Leu Met Arg Met Leu Gln Met Leu Val
                85                  90                  95
Leu Pro Leu Ile Ile Ser Ser Leu Val Thr Gly Met Ala Ala Leu Asp
                100                 105                 110
Ser Lys Ala Ser Gly Lys Trp Glu Cys Gly Ala Val Val Tyr Tyr Met
            115                 120                 125
Thr Thr Thr Ile Ile Ala Val Val Ile Gly Ile Ile Val Ile Ile
            130                 135                 140
Ile His Pro Gly Lys Gly Thr Lys Glu Asn Met His Arg Glu Gly Lys
145                 150                 155                 160
Ile Val Arg Val Thr Ala Ala Asp Ala Phe Leu Asp Leu Ile Arg Asn
                165                 170                 175
Met Leu Asn Pro Asn Leu Val Glu Ala Cys Phe Lys Gln Phe Lys Thr
                180                 185                 190
Asn Tyr Glu Lys Arg Ser Phe Lys Val Pro Ile Gln Ala Asn Glu Thr
            195                 200                 205
Leu Val Gly Ala Val Ile Asn Asn Val Ser Glu Ala Met Glu Thr Leu
            210                 215                 220
Thr Arg Ile Thr Glu Glu Leu Val Pro Val Pro Gly Ser Val Asn Gly
225                 230                 235                 240
Val Asn Ala Leu Gly Leu Val Val Phe Ser Met Cys Phe Gly Phe Val
                245                 250                 255
Ile Gly Asn Met Lys Glu Gln Gly Gln Ala Leu Arg Glu Phe Phe Asp
                260                 265                 270
Ser Leu Asn Glu Ala Ile Met Arg Leu Val Ala Val Ile Met Trp Tyr
            275                 280                 285
Ala Pro Val Gly Ile Leu Phe Leu Ile Ala Gly Lys Ile Val Glu Met
290                 295                 300
Glu Asp Met Gly Val Ile Gly Gly Gln Leu Ala Met Tyr Thr Val Thr
305                 310                 315                 320
Val Ile Val Gly Leu Leu Ile His Ala Val Ile Val Leu Pro Leu Leu
                325                 330                 335
Tyr Phe Leu Val Thr Arg Lys Asn Pro Trp Val Phe Ile Gly Gly Leu
            340                 345                 350
Leu Gln Ala Leu Ile Thr Ala Leu Gly Thr Ser Ser Ser Ser Ala Thr
            355                 360                 365
Leu Pro Ile Thr Phe Lys Cys Leu Glu Glu Asn Asn Gly Val Asp Lys
            370                 375                 380
Arg Val Thr Arg Phe Val Leu Pro Val Gly Ala Thr Ile Asn Met Asp
385                 390                 395                 400
Gly Thr Ala Leu Tyr Glu Ala Leu Ala Ala Ile Phe Ile Ala Gln Val
                405                 410                 415
Asn Asn Phe Glu Leu Asn Phe Gly Gln Ile Ile Thr Ile Ser Ile Thr
            420                 425                 430
Ala Thr Ala Ala Ser Ile Gly Ala Ala Gly Ile Pro Gln Ala Gly Leu
```

```
                    435                  440                  445
Val Thr Met Val Ile Val Leu Thr Ser Val Gly Leu Pro Thr Asp Asp
            450                  455                  460

Ile Thr Leu Ile Ile Ala Val Asp Trp Phe Leu Asp Arg Leu Arg Thr
465                  470                  475                  480

Thr Thr Asn Val Leu Gly Asp Ser Leu Gly Ala Gly Ile Val Glu His
                485                  490                  495

Leu Ser Arg His Glu Leu Lys Asn Arg Asp Val Glu Met Gly Asn Ser
            500                  505                  510

Val Ile Glu Glu Asn Glu Met Lys Lys Pro Tyr Gln Leu Ile Ala Gln
            515                  520                  525

Asp Asn Glu Thr Glu Lys Pro Ile Asp Ser Glu Thr Lys Met
            530                  535                  540

(2) INFORMATION FOR SEQ ID NO:6:

(i) SEQUENCE CHARACTERISTICS:
        (A) LENGTH: 1800 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: 5'UTR
        (B) LOCATION: 1..33

(ix) FEATURE:
        (A) NAME/KEY: CDS
        (B) LOCATION: 34..1755

(ix) FEATURE:
        (A) NAME/KEY: 3'UTR
        (B) LOCATION: 1756..1800

(xi) SEQUENCE DESCRIPTION: SEQ ID NO:6:

GATAGTGCTG AAGAGGAGGG GCGTTCCCAG ACC ATG GCA TCT ACG GAA GGT GCC        54
                                    Met Ala Ser Thr Glu Gly Ala
                                      1               5

AAC AAT ATG CCC AAG CAG GTG GAA GTG CGA ATG CCA GAC AGT CAT CTT       102
Asn Asn Met Pro Lys Gln Val Glu Val Arg Met Pro Asp Ser His Leu
         10                  15                  20

GGC TCA GAG GAA CCC AAG CAC CGG CAC CTG GGC CTG CGC CTG TGT GAC       150
Gly Ser Glu Glu Pro Lys His Arg His Leu Gly Leu Arg Leu Cys Asp
 25                  30                  35

AAG CTG GGG AAG AAT CTG CTG CTC ACC CTG ACG GTG TTT GGT GTC ATC       198
Lys Leu Gly Lys Asn Leu Leu Leu Thr Leu Thr Val Phe Gly Val Ile
 40                  45                  50                  55

CTG GGA GCA GTG TGT GGA GGG CTT CTT CGC TTG GCA TCT CCC ATC CAC       246
Leu Gly Ala Val Cys Gly Gly Leu Leu Arg Leu Ala Ser Pro Ile His
                 60                  65                  70

CCT GAT GTG GTT ATG TTA ATA GCC TTC CCA GGG GAT ATA CTC ATG AGG       294
Pro Asp Val Val Met Leu Ile Ala Phe Pro Gly Asp Ile Leu Met Arg
             75                  80                  85

ATG CTA AAA ATG CTC ATT CTG GGT CTA ATC ATC TCC AGC TTA ATC ACA       342
Met Leu Lys Met Leu Ile Leu Gly Leu Ile Ile Ser Ser Leu Ile Thr
         90                  95                 100

GGG TTG TCA GGC CTG GAT GCT AAG GCT AGT GGC CGC TTG GGC ACG AGA       390
Gly Leu Ser Gly Leu Asp Ala Lys Ala Ser Gly Arg Leu Gly Thr Arg
    105                 110                 115

GCC ATG GTG TAT TAC ATG TCC ACG ACC ATC ATT GCT GCA GTA CTG GGG       438
Ala Met Val Tyr Tyr Met Ser Thr Thr Ile Ile Ala Ala Val Leu Gly
120                 125                 130                 135
```

```
GTC ATT CTG GTC TTG GCT ATC CAT CCA GGC AAT CCC AAG CTC AAG AAG        486
Val Ile Leu Val Leu Ala Ile His Pro Gly Asn Pro Lys Leu Lys Lys
            140                 145                 150

CAG CTG GGG CCT GGG AAG AAG AAT GAT GAA GTG TCC AGC CTG GAT GCC        534
Gln Leu Gly Pro Gly Lys Lys Asn Asp Glu Val Ser Ser Leu Asp Ala
            155                 160                 165

TTC CTG GAC CTT ATT CGA AAT CTC TTC CCT GAA AAC CTT GTC CAA GCC        582
Phe Leu Asp Leu Ile Arg Asn Leu Phe Pro Glu Asn Leu Val Gln Ala
            170                 175                 180

TGC TTT CAA CAG ATT CAA ACA GTG ACG AAG AAA GTC CTG GTT GCA CCA        630
Cys Phe Gln Gln Ile Gln Thr Val Thr Lys Lys Val Leu Val Ala Pro
            185                 190                 195

CCG CCA GAC GAG GAG GCC AAC GCA ACC AGC GCT GAA GTC TCT CTG TTG        678
Pro Pro Asp Glu Glu Ala Asn Ala Thr Ser Ala Glu Val Ser Leu Leu
200             205                 210                 215

AAC GAG ACT GTG ACT GAG GTG CCG GAG GAG ACT AAG ATG GTT ATC AAG        726
Asn Glu Thr Val Thr Glu Val Pro Glu Glu Thr Lys Met Val Ile Lys
            220                 225                 230

AAG GGC CTG GAG TTC AAG GAT GGG ATG AAC GTC TTA GGT CTG ATA GGG        774
Lys Gly Leu Glu Phe Lys Asp Gly Met Asn Val Leu Gly Leu Ile Gly
            235                 240                 245

TTT TTC ATT GCT TTT GGC ATC GCT ATG GGG AAG ATG GGA GAT CAG GCC        822
Phe Phe Ile Ala Phe Gly Ile Ala Met Gly Lys Met Gly Asp Gln Ala
            250                 255                 260

AAG CTG ATG GTG GAT TTC TTC AAC ATT TTG AAT GAG ATT GTA ATG AAG        870
Lys Leu Met Val Asp Phe Phe Asn Ile Leu Asn Glu Ile Val Met Lys
            265                 270                 275

TTA GTG ATC ATG ATC ATG TGG TAC TCT CCC CTG GGT ATC GCC TGC CTG        918
Leu Val Ile Met Ile Met Trp Tyr Ser Pro Leu Gly Ile Ala Cys Leu
280             285                 290                 295

ATC TGT GGA AAG ATC ATT GCA ATC AAG GAC TTA GAA GTG GTT GCT AGG        966
Ile Cys Gly Lys Ile Ile Ala Ile Lys Asp Leu Glu Val Val Ala Arg
            300                 305                 310

CAA CTG GGG ATG TAC ATG GTA ACA GTG ATC ATA GGC CTC ATC ATC CAC       1014
Gln Leu Gly Met Tyr Met Val Thr Val Ile Ile Gly Leu Ile Ile His
            315                 320                 325

GGG GGC ATC TTT CTC CCC TTG ATT TAC TTT GTA GTG ACC AGG AAA AAC       1062
Gly Gly Ile Phe Leu Pro Leu Ile Tyr Phe Val Val Thr Arg Lys Asn
            330                 335                 340

CCC TTC TCC CTT TTT GCT GGC ATT TTC CAA GCT TGG ATC ACT GCC CTG       1110
Pro Phe Ser Leu Phe Ala Gly Ile Phe Gln Ala Trp Ile Thr Ala Leu
            345                 350                 355

GGC ACC GCT TCC AGT GCT GGA ACT TTG CCT GTC ACC TTT CGT TGC CTG       1158
Gly Thr Ala Ser Ser Ala Gly Thr Leu Pro Val Thr Phe Arg Cys Leu
360             365                 370                 375

GAA GAA AAT CTG GGG ATT GAT AAG CGT GTG ACT AGA TTC GTC CTT CCT       1206
Glu Glu Asn Leu Gly Ile Asp Lys Arg Val Thr Arg Phe Val Leu Pro
            380                 385                 390

GTT GGA GCA ACC ATT AAC ATG GAT GGT ACA GCC CTT TAT GAA GCG GTG       1254
Val Gly Ala Thr Ile Asn Met Asp Gly Thr Ala Leu Tyr Glu Ala Val
            395                 400                 405

GCC GCC ATC TTT ATA GCC CAA ATG AAT GGT GTT GTC CTG GAT GGA GGA       1302
Ala Ala Ile Phe Ile Ala Gln Met Asn Gly Val Val Leu Asp Gly Gly
            410                 415                 420

CAG ATT GTG ACT GTA AGC CTC ACA GCC ACC CTG GCA AGC GTC GGC GCG       1350
Gln Ile Val Thr Val Ser Leu Thr Ala Thr Leu Ala Ser Val Gly Ala
            425                 430                 435

GCC AGT ATC CCC AGT GCC GGG CTG GTC ACC ATG CTC CTC ATT CTG ACA       1398
Ala Ser Ile Pro Ser Ala Gly Leu Val Thr Met Leu Leu Ile Leu Thr
440             445                 450                 455
```

```
GCC GTG GGC CTG CCA ACA GAG GAC ATC AGC TTG CTG GTG GCT GTG GAC      1446
Ala Val Gly Leu Pro Thr Glu Asp Ile Ser Leu Leu Val Ala Val Asp
            460                 465                 470

TGG CTG CTG GAC AGG ATG AGA ACT TCA GTC AAT GTT GTG GGT GAC TCT      1494
Trp Leu Leu Asp Arg Met Arg Thr Ser Val Asn Val Val Gly Asp Ser
            475                 480                 485

TTT GGG GCT GGG ATA GTC TAT CAC CTC TCC AAG TCT GAG CTG GAT ACC      1542
Phe Gly Ala Gly Ile Val Tyr His Leu Ser Lys Ser Glu Leu Asp Thr
            490                 495                 500

ATT GAC TCC CAG CAT CGA GTG CAT GAA GAT ATT GAA ATG ACC AAG ACT      1590
Ile Asp Ser Gln His Arg Val His Glu Asp Ile Glu Met Thr Lys Thr
            505                 510                 515

CAA TCC ATT TAT GAT GAC ATG AAG AAC CAC AGG GAA AGC AAC TCT AAT      1638
Gln Ser Ile Tyr Asp Asp Met Lys Asn His Arg Glu Ser Asn Ser Asn
520                 525                 530                 535

CAA TGT GTC TAT GCT GCA CAC AAC TCT GTC ATA GTA GAT GAA TGC AAG      1686
Gln Cys Val Tyr Ala Ala His Asn Ser Val Ile Val Asp Glu Cys Lys
            540                 545                 550

GTA ACT CTG GCA GCC AAT GGA AAG TCA GCC GAC TGC AGT GTT GAG GAA      1734
Val Thr Leu Ala Ala Asn Gly Lys Ser Ala Asp Cys Ser Val Glu Glu
            555                 560                 565

GAA CCT TGG AAA CGT GAG AAA TAAGGATATG AGTCTCAGCA AATTCTTGAA         1785
Glu Pro Trp Lys Arg Glu Lys
            570

TAAACTCCCC AGCGT                                                     1800

(2) INFORMATION FOR SEQ ID NO:7:

(i) SEQUENCE CHARACTERISTICS:
        (A) LENGTH: 574 amino acids
        (B) TYPE: amino acid
        (D) TOPOLOGY: linear (ii) MOLECULE TYPE: protein (xi) SEQUENCE DESCRIPTION: SEQ ID NO:7:

Met Ala Ser Thr Glu Gly Ala Asn Asn Met Pro Lys Gln Val Glu Val
 1               5                  10                  15

Arg Met Pro Asp Ser His Leu Gly Ser Glu Glu Pro Lys His Arg His
                20                  25                  30

Leu Gly Leu Arg Leu Cys Asp Lys Leu Gly Lys Asn Leu Leu Leu Thr
            35                  40                  45

Leu Thr Val Phe Gly Val Ile Leu Gly Ala Val Cys Gly Gly Leu Leu
        50                  55                  60

Arg Leu Ala Ser Pro Ile His Pro Asp Val Val Met Leu Ile Ala Phe
65                  70                  75                  80

Pro Gly Asp Ile Leu Met Arg Met Leu Lys Met Leu Ile Leu Gly Leu
                85                  90                  95

Ile Ile Ser Ser Leu Ile Thr Gly Leu Ser Gly Leu Asp Ala Lys Ala
            100                 105                 110

Ser Gly Arg Leu Gly Thr Arg Ala Met Val Tyr Tyr Met Ser Thr Thr
        115                 120                 125

Ile Ile Ala Ala Val Leu Gly Val Ile Leu Val Leu Ala Ile His Pro
    130                 135                 140

Gly Asn Pro Lys Leu Lys Lys Gln Leu Gly Pro Gly Lys Lys Asn Asp
145                 150                 155                 160

Glu Val Ser Ser Leu Asp Ala Phe Leu Asp Leu Ile Arg Asn Leu Phe
                165                 170                 175
```

Pro Glu Asn Leu Val Gln Ala Cys Phe Gln Gln Ile Gln Thr Val Thr
            180                 185                 190

Lys Lys Val Leu Val Ala Pro Pro Asp Glu Glu Ala Asn Ala Thr
            195                 200                 205

Ser Ala Glu Val Ser Leu Leu Asn Glu Thr Val Thr Glu Val Pro Glu
210                 215                 220

Glu Thr Lys Met Val Ile Lys Lys Gly Leu Glu Phe Lys Asp Gly Met
225                 230                 235                 240

Asn Val Leu Gly Leu Ile Gly Phe Phe Ile Ala Phe Gly Ile Ala Met
            245                 250                 255

Gly Lys Met Gly Asp Gln Ala Lys Leu Met Val Asp Phe Phe Asn Ile
            260                 265                 270

Leu Asn Glu Ile Val Met Lys Leu Val Ile Met Ile Met Trp Tyr Ser
            275                 280                 285

Pro Leu Gly Ile Ala Cys Leu Ile Cys Gly Lys Ile Ile Ala Ile Lys
            290                 295                 300

Asp Leu Glu Val Val Ala Arg Gln Leu Gly Met Tyr Met Val Thr Val
305                 310                 315                 320

Ile Ile Gly Leu Ile Ile His Gly Gly Ile Phe Leu Pro Leu Ile Tyr
            325                 330                 335

Phe Val Val Thr Arg Lys Asn Pro Phe Ser Leu Phe Ala Gly Ile Phe
            340                 345                 350

Gln Ala Trp Ile Thr Ala Leu Gly Thr Ala Ser Ser Ala Gly Thr Leu
            355                 360                 365

Pro Val Thr Phe Arg Cys Leu Glu Glu Asn Leu Gly Ile Asp Lys Arg
            370                 375                 380

Val Thr Arg Phe Val Leu Pro Val Gly Ala Thr Ile Asn Met Asp Gly
385                 390                 395                 400

Thr Ala Leu Tyr Glu Ala Val Ala Ala Ile Phe Ile Ala Gln Met Asn
            405                 410                 415

Gly Val Val Leu Asp Gly Gly Gln Ile Val Thr Val Ser Leu Thr Ala
            420                 425                 430

Thr Leu Ala Ser Val Gly Ala Ala Ser Ile Pro Ser Ala Gly Leu Val
            435                 440                 445

Thr Met Leu Leu Ile Leu Thr Ala Val Gly Leu Pro Thr Glu Asp Ile
            450                 455                 460

Ser Leu Leu Val Ala Val Asp Trp Leu Leu Asp Arg Met Arg Thr Ser
465                 470                 475                 480

Val Asn Val Val Gly Asp Ser Phe Gly Ala Gly Ile Val Tyr His Leu
            485                 490                 495

Ser Lys Ser Glu Leu Asp Thr Ile Asp Ser Gln His Arg Val His Glu
            500                 505                 510

Asp Ile Glu Met Thr Lys Thr Gln Ser Ile Tyr Asp Asp Met Lys Asn
            515                 520                 525

His Arg Glu Ser Asn Ser Asn Gln Cys Val Tyr Ala Ala His Asn Ser
            530                 535                 540

Val Ile Val Asp Glu Cys Lys Val Thr Leu Ala Ala Asn Gly Lys Ser
545                 550                 555                 560

Ala Asp Cys Ser Val Glu Glu Glu Pro Trp Lys Arg Glu Lys
            565                 570

(2) INFORMATION FOR SEQ ID NO:8:

(i) SEQUENCE CHARACTERISTICS:
        (A) LENGTH: 1674 base pairs (B) TYPE: nucleic acid
(C) STRANDEDNESS: single
(D) TOPOLOGY: linear (ii) MOLECULE TYPE: cDNA (ix) FEATURE:
(A) NAME/KEY: 5'UTR
(B) LOCATION: 1..15

(ix) FEATURE:
(A) NAME/KEY: CDS
(B) LOCATION: 16..1590

(ix) FEATURE:
(A) NAME/KEY: 3'UTR
(B) LOCATION: 1591..1674

(xi) SEQUENCE DESCRIPTION: SEQ ID NO:8:

```
ATAGCGGCGA CAGCC ATG GGG AAA CCG GCG AGG AAA GGA TGC CCG AGT TGG        51
                Met Gly Lys Pro Ala Arg Lys Gly Cys Pro Ser Trp
                 1               5                  10

AAG CGC TTC CTG AAG AAT AAC TGG GTG TTG CTG TCC ACC GTG GCC GCG        99
Lys Arg Phe Leu Lys Asn Asn Trp Val Leu Leu Ser Thr Val Ala Ala
         15                  20                  25

GTG GTA CTA GGC ATT ACC ACA GGA GTC TTG GTT CGA GAA CAC AGC AAC       147
Val Val Leu Gly Ile Thr Thr Gly Val Leu Val Arg Glu His Ser Asn
     30                  35                  40

CTC TCA ACT CTA GAG AAA TTC TAC TTT GCT TTT CCT GGA GAA ATT CTA       195
Leu Ser Thr Leu Glu Lys Phe Tyr Phe Ala Phe Pro Gly Glu Ile Leu
 45                  50                  55                  60

ATG CGG ATG CTG AAA CTC ATC ATT TTG CCA TTA ATT ATA TCC AGC ATG       243
Met Arg Met Leu Lys Leu Ile Ile Leu Pro Leu Ile Ile Ser Ser Met
                 65                  70                  75

ATT ACA GGT GTT GCT GCA CTG GAT TCC AAC GTA TCC GGA AAA ATT GGT       291
Ile Thr Gly Val Ala Ala Leu Asp Ser Asn Val Ser Gly Lys Ile Gly
         80                  85                  90

CTG CGC GCT GTC GTG TAT TAT TTC TGT ACC ACT CTC ATT GCT GTT ATT       339
Leu Arg Ala Val Val Tyr Tyr Phe Cys Thr Thr Leu Ile Ala Val Ile
     95                 100                 105

CTA GGT ATT GTG CTG GTG GTG AGC ATC AAG CCT GGT GTC ACC CAG AAA       387
Leu Gly Ile Val Leu Val Val Ser Ile Lys Pro Gly Val Thr Gln Lys
110                 115                 120

GTG GGT GAA ATT GCG AGG ACA GGC AGC ACC CCT GAA GTC AGT ACG GTG       435
Val Gly Glu Ile Ala Arg Thr Gly Ser Thr Pro Glu Val Ser Thr Val
125                 130                 135                 140

GAT GCC ATG TTA GAT CTC ATC AGG AAT ATG TTC CCT GAG AAT CTT GTC       483
Asp Ala Met Leu Asp Leu Ile Arg Asn Met Phe Pro Glu Asn Leu Val
             145                 150                 155

CAG GCC TGT TTT CAG CAG TAC AAA ACT AAG CGT GAA GAA GTG AAG CCT       531
Gln Ala Cys Phe Gln Gln Tyr Lys Thr Lys Arg Glu Glu Val Lys Pro
         160                 165                 170

CCC AGC GAT CCA GAG ATG AAC ATG ACA GAA GAG TCC TTC ACA GCT GTC       579
Pro Ser Asp Pro Glu Met Asn Met Thr Glu Glu Ser Phe Thr Ala Val
     175                 180                 185

ATG ACA ACT GCA ATT TCC AAG AAC AAA ACA AAG GAA TAC AAA ATT GTT       627
Met Thr Thr Ala Ile Ser Lys Asn Lys Thr Lys Glu Tyr Lys Ile Val
190                 195                 200

GGC ATG TAT TCA GAT GGC ATA AAC GTC CTG GGC TTG ATT GTC TTT TGC       675
Gly Met Tyr Ser Asp Gly Ile Asn Val Leu Gly Leu Ile Val Phe Cys
205                 210                 215                 220

CTT GTC TTT GGA CTT GTC ATT GGA AAA ATG GGA GAA AAG GGA CAA ATT       723
Leu Val Phe Gly Leu Val Ile Gly Lys Met Gly Glu Lys Gly Gln Ile
             225                 230                 235
```

| | |
|---|---|
| CTG GTG GAT TTC TTC AAT GCT TTG AGT GAT GCA ACC ATG AAA ATC GTT<br>Leu Val Asp Phe Phe Asn Ala Leu Ser Asp Ala Thr Met Lys Ile Val<br>240                         245                       250 | 771 |
| CAG ATC ATC ATG TGT TAT ATG CCA CTA GGT ATT TTG TTC CTG ATT GCT<br>Gln Ile Ile Met Cys Tyr Met Pro Leu Gly Ile Leu Phe Leu Ile Ala<br>        255                     260                     265 | 819 |
| GGG AAG ATC ATA GAA GTT GAA GAC TGG GAA ATA TTC CGC AAG CTG GGC<br>Gly Lys Ile Ile Glu Val Glu Asp Trp Glu Ile Phe Arg Lys Leu Gly<br>270                       275                     280 | 867 |
| CTT TAC ATG GCC ACA GTC CTG ACT GGG CTT GCA ATC CAC TCC ATT GTA<br>Leu Tyr Met Ala Thr Val Leu Thr Gly Leu Ala Ile His Ser Ile Val<br>285                       290                     295               300 | 915 |
| ATT CTC CCG CTG ATA TAT TTC ATA GTC GTA CGA AAG AAC CCT TTC CGA<br>Ile Leu Pro Leu Ile Tyr Phe Ile Val Val Arg Lys Asn Pro Phe Arg<br>               305                     310                     315 | 963 |
| TTT GCC ATG GGA ATG GCC CAG GCT CTC CTG ACA GCT CTC ATG ATC TCT<br>Phe Ala Met Gly Met Ala Gln Ala Leu Leu Thr Ala Leu Met Ile Ser<br>               320                     325                     330 | 1011 |
| TCC AGT TCA GCA ACA CTG CCT GTC ACC TTC CGC TGT GCT GAA GAA AAT<br>Ser Ser Ser Ala Thr Leu Pro Val Thr Phe Arg Cys Ala Glu Glu Asn<br>               335                     340                     345 | 1059 |
| AAC CAG GTG GAC AAG AGG ATC ACT CGA TTC GTG TTA CCC GTT GGT GCA<br>Asn Gln Val Asp Lys Arg Ile Thr Arg Phe Val Leu Pro Val Gly Ala<br>350                       355                     360 | 1107 |
| ACA ATC AAC ATG GAT GGG ACC GCG CTC TAT GAA GCA GTG GCA GCG GTG<br>Thr Ile Asn Met Asp Gly Thr Ala Leu Tyr Glu Ala Val Ala Ala Val<br>365                       370                     375               380 | 1155 |
| TTT ATT GCA CAG TTG AAT GAC CTG GAC TTG GGC ATT GGG CAG ATC ATC<br>Phe Ile Ala Gln Leu Asn Asp Leu Asp Leu Gly Ile Gly Gln Ile Ile<br>               385                     390                     395 | 1203 |
| ACC ATC AGT ATC ACG GCC ACA TCT GCC AGC ATC GGA GCT GCT GGC GTG<br>Thr Ile Ser Ile Thr Ala Thr Ser Ala Ser Ile Gly Ala Ala Gly Val<br>               400                     405                     410 | 1251 |
| CCC CAG GCT GGC CTG GTG ACC ATG GTG ATT GTG CTG AGT GCC GTG GGC<br>Pro Gln Ala Gly Leu Val Thr Met Val Ile Val Leu Ser Ala Val Gly<br>               415                     420                     425 | 1299 |
| CTG CCC GCC GAG GAT GTC ACC CTG ATC ATT GCT GTC GAC TGG CTC CTG<br>Leu Pro Ala Glu Asp Val Thr Leu Ile Ile Ala Val Asp Trp Leu Leu<br>430                       435                     440 | 1347 |
| GAC CGG TTC AGG ACC ATG GTC AAC GTC CTT GGT GAT GCT TTT GGG ACG<br>Asp Arg Phe Arg Thr Met Val Asn Val Leu Gly Asp Ala Phe Gly Thr<br>445                       450                     455               460 | 1395 |
| GGC ATT GTG GAA AAG CTC TCC AAG AAG GAG CTG GAG CAG ATG GAT GTT<br>Gly Ile Val Glu Lys Leu Ser Lys Lys Glu Leu Glu Gln Met Asp Val<br>               465                     470                     475 | 1443 |
| TCA TCT GAA GTC AAC ATT GTG AAT CCC TTT GCC TTG GAA TCC ACA ATC<br>Ser Ser Glu Val Asn Ile Val Asn Pro Phe Ala Leu Glu Ser Thr Ile<br>               480                     485                     490 | 1491 |
| CTT GAC AAC GAA GAC TCA GAC ACC AAG AAG TCT TAT GTC AAT GGA GGC<br>Leu Asp Asn Glu Asp Ser Asp Thr Lys Lys Ser Tyr Val Asn Gly Gly<br>               495                     500                     505 | 1539 |
| TTT GCA GTA GAC AAG TCT GAC ACC ATC TCA TTC ACC CAG ACC TCA CAG<br>Phe Ala Val Asp Lys Ser Asp Thr Ile Ser Phe Thr Gln Thr Ser Gln<br>510                       515                     520 | 1587 |
| TTC TAGGGCCCCT GGCTGCAGAT GACTGGAAAC AAGGAAGGAC ATTTCGTGAG<br>Phe<br><br>525 | 1640 |
| AGTCATCTCA AACACGGCTT AAGGAAAAGA GAAA | 1674 |

(2) INFORMATION FOR SEQ ID NO:9:

(i) SEQUENCE CHARACTERISTICS:
        (A) LENGTH: 525 amino acids
        (B) TYPE: amino acid
        (D) TOPOLOGY: linear (ii) MOLECULE TYPE: protein (xi) SEQUENCE DESCRIPTION: SEQ ID NO:9:

```
Met Gly Lys Pro Ala Arg Lys Gly Cys Pro Ser Trp Lys Arg Phe Leu
 1               5                  10                  15

Lys Asn Asn Trp Val Leu Leu Ser Thr Val Ala Val Val Leu Gly
            20                  25                  30

Ile Thr Thr Gly Val Leu Val Arg Glu His Ser Asn Leu Ser Thr Leu
            35                  40                  45

Glu Lys Phe Tyr Phe Ala Phe Pro Gly Glu Ile Leu Met Arg Met Leu
        50                  55                  60

Lys Leu Ile Ile Leu Pro Leu Ile Ile Ser Ser Met Ile Thr Gly Val
65                  70                  75                  80

Ala Ala Leu Asp Ser Asn Val Ser Gly Lys Ile Gly Leu Arg Ala Val
                85                  90                  95

Val Tyr Tyr Phe Cys Thr Thr Leu Ile Ala Val Ile Leu Gly Ile Val
                100                 105                 110

Leu Val Val Ser Ile Lys Pro Gly Val Thr Gln Lys Val Gly Glu Ile
            115                 120                 125

Ala Arg Thr Gly Ser Thr Pro Glu Val Ser Thr Val Asp Ala Met Leu
        130                 135                 140

Asp Leu Ile Arg Asn Met Phe Pro Glu Asn Leu Val Gln Ala Cys Phe
145                 150                 155                 160

Gln Gln Tyr Lys Thr Lys Arg Glu Glu Val Lys Pro Pro Ser Asp Pro
                165                 170                 175

Glu Met Asn Met Thr Glu Glu Ser Phe Thr Ala Val Met Thr Thr Ala
                180                 185                 190

Ile Ser Lys Asn Lys Thr Lys Glu Tyr Lys Ile Val Gly Met Tyr Ser
            195                 200                 205

Asp Gly Ile Asn Val Leu Gly Leu Ile Val Phe Cys Leu Val Phe Gly
        210                 215                 220

Leu Val Ile Gly Lys Met Gly Glu Lys Gly Gln Ile Leu Val Asp Phe
225                 230                 235                 240

Phe Asn Ala Leu Ser Asp Ala Thr Met Lys Ile Val Gln Ile Ile Met
                245                 250                 255

Cys Tyr Met Pro Leu Gly Ile Leu Phe Leu Ile Ala Gly Lys Ile Ile
                260                 265                 270

Glu Val Glu Asp Trp Glu Ile Phe Arg Lys Leu Gly Leu Tyr Met Ala
            275                 280                 285

Thr Val Leu Thr Gly Leu Ala Ile His Ser Ile Val Ile Leu Pro Leu
        290                 295                 300

Ile Tyr Phe Ile Val Val Arg Lys Asn Pro Phe Arg Phe Ala Met Gly
305                 310                 315                 320

Met Ala Gln Ala Leu Leu Thr Ala Leu Met Ile Ser Ser Ser Ala
                325                 330                 335

Thr Leu Pro Val Thr Phe Arg Cys Ala Glu Glu Asn Asn Gln Val Asp
            340                 345                 350

Lys Arg Ile Thr Arg Phe Val Leu Pro Val Gly Ala Thr Ile Asn Met
        355                 360                 365
```

```
Asp Gly Thr Ala Leu Tyr Glu Ala Val Ala Val Phe Ile Ala Gln
    370                 375                 380

Leu Asn Asp Leu Asp Leu Gly Ile Gly Gln Ile Thr Ile Ser Ile
385                 390                 395                 400

Thr Ala Thr Ser Ala Ser Ile Gly Ala Ala Gly Val Pro Gln Ala Gly
                405                 410                 415

Leu Val Thr Met Val Ile Val Leu Ser Ala Val Gly Leu Pro Ala Glu
            420                 425                 430

Asp Val Thr Leu Ile Ile Ala Val Asp Trp Leu Leu Asp Arg Phe Arg
            435                 440                 445

Thr Met Val Asn Val Leu Gly Asp Ala Phe Gly Thr Gly Ile Val Glu
        450                 455                 460

Lys Leu Ser Lys Lys Glu Leu Glu Gln Met Asp Val Ser Ser Glu Val
465                 470                 475                 480

Asn Ile Val Asn Pro Phe Ala Leu Glu Ser Thr Ile Leu Asp Asn Glu
                485                 490                 495

Asp Ser Asp Thr Lys Lys Ser Tyr Val Asn Gly Gly Phe Ala Val Asp
                500                 505                 510

Lys Ser Asp Thr Ile Ser Phe Thr Gln Thr Ser Gln Phe
            515                 520                 525
```

(2) INFORMATION FOR SEQ ID NO:10:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

CGCGGGTACC GCCATGGAGA AGAGCAAC                                    28

(2) INFORMATION FOR SEQ ID NO:11:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

CGCGTCTAGA TCACAGAACC GACTCCTTG                                29

(2) INFORMATION FOR SEQ ID NO:12:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

CGCGGGTACC AATATGACTA AAAGCAATG                                29

(2) INFORMATION FOR SEQ ID NO:13:

(i) SEQUENCE CHARACTERISTICS:
        (A) LENGTH: 29 base pairs (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

CGCGTCTAGA CTACATCTTG GTTTCACTG                                         29

(2) INFORMATION FOR SEQ ID NO:14:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

CGCGGGTACC ACCATGGCAT CTACGGAAG                                         29

(2) INFORMATION FOR SEQ ID NO:15:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

CGCGTCTAGA TTATTTCTCA CGTTTCCAAG                                        30

(2) INFORMATION FOR SEQ ID NO:16:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

CGCGGGTACC GCCATGGGGA AACCGGCG                                          28

(2) INFORMATION FOR SEQ ID NO:17:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

CGCGGGATCC CTAGAACTGT GAGGTCTG                                          28